US011016090B2

(12) United States Patent
O'Farrell et al.

(10) Patent No.: US 11,016,090 B2
(45) Date of Patent: *May 25, 2021

(54) LATERAL FLOW ASSAYS USING TWO DIMENSIONAL FEATURES

(71) Applicant: Symbolics, LLC, Irvine, CA (US)

(72) Inventors: Brendan O'Farrell, Santa Ana, CA (US); Thomas C. Tisone, Orange, CA (US)

(73) Assignee: SYMBOLICS, LLC, Irvine, CA (US)

( * ) Notice: Subject to any disclaimer, the term of this patent is extended or adjusted under 35 U.S.C. 154(b) by 511 days.

This patent is subject to a terminal disclaimer.

(21) Appl. No.: 15/861,623

(22) Filed: Jan. 3, 2018

(65) Prior Publication Data

US 2018/0224469 A1 Aug. 9, 2018

Related U.S. Application Data

(60) Continuation of application No. 13/862,313, filed on Apr. 12, 2013, now Pat. No. 9,874,576, which is a division of application No. 13/343,681, filed on Jan. 4, 2012, now Pat. No. 8,486,717.

(60) Provisional application No. 61/461,499, filed on Jan. 18, 2011.

(51) Int. Cl.
*G01N 33/558* (2006.01)
*G01N 33/76* (2006.01)
*G01N 33/543* (2006.01)

(52) U.S. Cl.
CPC ..... *G01N 33/558* (2013.01); *G01N 33/54386* (2013.01); *G01N 33/76* (2013.01)

(58) Field of Classification Search
CPC ............ G01N 33/76; G01N 33/54386; G01N 33/558; B01L 2300/0821
USPC ................................................. 427/2.11, 2.13
See application file for complete search history.

(56) References Cited

U.S. PATENT DOCUMENTS

| | | |
|---|---|---|
| 872,357 A | 12/1907 | Lerch et al. |
| 3,641,235 A | 2/1972 | Weiss |
| 3,959,078 A | 5/1976 | Guire |
| 3,966,897 A | 6/1976 | Renn et al. |
| 4,094,647 A | 6/1978 | Deutsch et al. |
| 4,168,146 A | 9/1979 | Grubb et al. |
| 4,299,916 A | 11/1981 | Litman et al. |
| 4,332,788 A | 6/1982 | Mochida et al. |
| 4,347,312 A | 8/1982 | Brown et al. |

(Continued)

FOREIGN PATENT DOCUMENTS

| | | |
|---|---|---|
| CA | 2 216 214 | 5/1999 |
| CN | 1800831 | 7/2006 |

(Continued)

OTHER PUBLICATIONS

International Search Report and Written Opinion for PCT/US2012/021586, dated Apr. 19, 2012, 8 pages.

(Continued)

*Primary Examiner* — Christopher L Chin
(74) *Attorney, Agent, or Firm* — Rimon P.C.

(57) ABSTRACT

The present invention relates to novel lateral flow devices using two dimensional features, preferably, uniform two dimensional test and control features, and the methods for detecting an analyte using the lateral flow devices, and processes for making the lateral flow devices.

22 Claims, 12 Drawing Sheets
(12 of 12 Drawing Sheet(s) Filed in Color)

(56) References Cited

U.S. PATENT DOCUMENTS

| | | | |
|---|---|---|---|
| 4,366,241 A | 12/1982 | Tom et al. |
| 4,373,932 A | 2/1983 | Gribnau et al. |
| 4,391,904 A | 7/1983 | Litman et al. |
| 4,425,438 A | 1/1984 | Bauman et al. |
| 4,517,288 A | 5/1985 | Giegel et al. |
| 4,695,554 A | 9/1987 | O'Connell et al. |
| 4,703,017 A | 10/1987 | Campbell et al. |
| 4,740,468 A | 4/1988 | Weng et al. |
| 4,743,560 A | 5/1988 | Campbell et al. |
| 4,778,751 A | 10/1988 | El Shami |
| 4,857,453 A | 8/1989 | Ullman et al. |
| 4,861,711 A | 8/1989 | Friesen et al. |
| 4,955,302 A | 9/1990 | Gordon et al. |
| 4,956,302 A | 9/1990 | Gordon et al. |
| 4,960,691 A | 10/1990 | Gordon et al. |
| 5,073,484 A | 12/1991 | Swanson et al. |
| 5,075,078 A | 12/1991 | Osikowicz |
| 5,079,142 A | 1/1992 | Coleman et al. |
| 5,120,643 A | 6/1992 | Ching et al. |
| 5,132,085 A | 7/1992 | Pelanek |
| 5,141,875 A | 8/1992 | Kelton et al. |
| 5,160,701 A | 11/1992 | Brown |
| 5,200,312 A * | 4/1993 | Oprandy ............... G01N 33/545 422/527 |
| 5,236,826 A | 8/1993 | Marshall |
| 5,252,459 A | 10/1993 | Tarcha et al. |
| 5,252,496 A | 10/1993 | Kang et al. |
| 5,275,785 A | 1/1994 | May et al. |
| 5,378,638 A | 1/1995 | Deeg et al. |
| 5,401,667 A | 3/1995 | Koike |
| 5,422,726 A | 6/1995 | Tyler |
| 5,501,949 A | 3/1996 | Marshall |
| 5,504,013 A | 4/1996 | Senior |
| 5,514,602 A | 5/1996 | Brooks, Jr. et al. |
| 5,559,041 A | 9/1996 | Kang et al. |
| 5,571,726 A | 11/1996 | Brooks, Jr. et al. |
| 5,578,577 A | 11/1996 | Ching et al. |
| 5,591,645 A | 1/1997 | Rosenstein |
| 5,596,414 A | 1/1997 | Tyler |
| 5,602,040 A | 2/1997 | May et al. |
| 5,622,871 A | 4/1997 | May et al. |
| 5,654,162 A | 8/1997 | Guire et al. |
| 5,656,448 A | 8/1997 | Kang et al. |
| 5,656,503 A | 8/1997 | May et al. |
| 5,710,005 A | 1/1998 | Rittenburg |
| 5,712,170 A | 1/1998 | Kouvonen et al. |
| 5,714,389 A | 2/1998 | Charlton et al. |
| 5,716,778 A | 2/1998 | Weng et al. |
| 5,718,778 A | 2/1998 | Weng et al. |
| 5,728,587 A | 3/1998 | Kang et al. |
| 5,747,273 A | 5/1998 | Khosravi et al. |
| 5,753,517 A | 5/1998 | Brooks et al. |
| 5,798,273 A | 8/1998 | Shuler et al. |
| 5,837,546 A | 11/1998 | Allen et al. |
| 5,869,252 A | 2/1999 | Bouma et al. |
| 5,915,386 A | 6/1999 | Lloyd et al. |
| 5,957,867 A | 9/1999 | Lloyd et al. |
| 5,965,458 A | 10/1999 | Kouvonen et al. |
| 5,968,839 A | 10/1999 | Blatt et al. |
| 5,989,921 A | 11/1999 | Charlton et al. |
| 6,017,767 A | 1/2000 | Chandler |
| 6,020,147 A | 2/2000 | Guire et al. |
| 6,027,943 A | 2/2000 | Kang et al. |
| 6,077,222 A | 6/2000 | Lloyd et al. |
| 6,080,106 A | 6/2000 | Lloyd et al. |
| 6,100,099 A | 8/2000 | Gordon et al. |
| 6,103,536 A | 8/2000 | Geisberg |
| 6,121,008 A | 9/2000 | Fitzpatrick et al. |
| 6,140,048 A | 10/2000 | Muller et al. |
| 6,140,134 A | 10/2000 | Rittenburg |
| 6,156,271 A | 12/2000 | May |
| 6,186,962 B1 | 2/2001 | Lloyd et al. |
| 6,187,269 B1 | 2/2001 | Lancesseur et al. |
| 6,187,598 B1 | 2/2001 | May et al. |
| 6,194,222 B1 | 2/2001 | Buechler et al. |
| 6,210,898 B1 | 4/2001 | Bouma et al. |
| D441,298 S | 5/2001 | Gundlach et al. |
| 6,228,660 B1 | 5/2001 | May et al. |
| 6,241,862 B1 | 6/2001 | McAleer et al. |
| 6,267,722 B1 | 7/2001 | Anderson et al. |
| 6,287,875 B1 | 9/2001 | Geisberg |
| 6,319,665 B1 | 11/2001 | Zwanziger et al. |
| 6,319,666 B1 | 11/2001 | Zwanziger et al. |
| 6,319,676 B1 | 11/2001 | Nazareth et al. |
| 6,352,862 B1 | 3/2002 | Davis et al. |
| 6,368,875 B1 | 4/2002 | Geisberg |
| 6,379,620 B1 | 4/2002 | Tydings et al. |
| 6,394,952 B1 | 5/2002 | Anderson et al. |
| 6,399,398 B1 | 6/2002 | Cunningham et al. |
| 6,403,380 B1 | 6/2002 | Catt et al. |
| 6,406,920 B1 | 6/2002 | Davis et al. |
| 6,409,662 B1 | 6/2002 | Lloyd et al. |
| 6,451,619 B1 | 9/2002 | Catt et al. |
| 6,454,726 B1 | 9/2002 | Catt et al. |
| 6,485,982 B1 | 11/2002 | Charlton |
| 6,506,612 B2 | 1/2003 | Kang et al. |
| 6,534,320 B2 | 3/2003 | Ching et al. |
| 6,541,277 B1 | 4/2003 | Kang et al. |
| 6,544,797 B1 | 4/2003 | Buechler et al. |
| 6,551,495 B1 | 4/2003 | Porter et al. |
| 6,585,663 B1 | 7/2003 | Coley et al. |
| 6,649,418 B1 | 11/2003 | Geisberg |
| D484,600 S | 12/2003 | Kaar et al. |
| RE38,430 E | 2/2004 | Rosenstein |
| 6,706,049 B2 | 3/2004 | Moerman |
| 6,707,554 B1 | 3/2004 | Miltner et al. |
| 6,719,923 B2 | 4/2004 | Stiene et al. |
| 6,737,277 B1 | 5/2004 | Kang et al. |
| 6,759,202 B2 | 7/2004 | Grossman et al. |
| 6,764,827 B1 | 7/2004 | Aoki et al. |
| 6,766,817 B2 | 7/2004 | da Silva |
| 6,767,709 B1 | 7/2004 | Suzuki et al. |
| 6,770,487 B2 | 8/2004 | Crosby |
| 6,777,198 B2 | 8/2004 | Mendel-Hartvig et al. |
| D497,673 S | 10/2004 | Long |
| 6,805,837 B2 | 10/2004 | Tydings |
| 6,805,838 B2 | 10/2004 | Tydings |
| D497,999 S | 11/2004 | Long |
| 6,812,038 B1 | 11/2004 | Mendel-Hartvig et al. |
| 6,818,455 B2 | 11/2004 | May et al. |
| 6,830,731 B1 | 12/2004 | Buechler et al. |
| 6,849,450 B2 | 2/2005 | Langley et al. |
| 6,861,214 B1 | 3/2005 | Rampal et al. |
| 6,867,051 B1 | 3/2005 | Anderson et al. |
| 6,916,666 B1 | 7/2005 | Mendel-Hartvig et al. |
| 6,927,064 B1 | 8/2005 | Catt et al. |
| 6,936,476 B1 | 8/2005 | Anderson et al. |
| D509,901 S | 9/2005 | Phelan et al. |
| D510,711 S | 10/2005 | Syme et al. |
| 6,951,631 B1 | 10/2005 | Catt et al. |
| 7,049,150 B2 | 5/2006 | Bachand |
| D523,964 S | 6/2006 | Phelan et al. |
| 7,081,348 B2 | 7/2006 | Suzuki et al. |
| 7,096,877 B2 | 8/2006 | Larsen et al. |
| 7,109,042 B2 | 9/2006 | May et al. |
| D530,825 S | 10/2006 | Lee et al. |
| D531,735 S | 11/2006 | Lee et al. |
| 7,138,269 B2 | 11/2006 | Blankenstein |
| 7,141,212 B2 | 11/2006 | Catt et al. |
| 7,153,651 B1 | 12/2006 | Drewes et al. |
| 7,153,681 B1 | 12/2006 | Penfold et al. |
| D536,798 S | 2/2007 | Lee et al. |
| 7,175,992 B2 | 2/2007 | Fond |
| 7,178,416 B2 | 2/2007 | Whelan et al. |
| 7,205,553 B2 | 4/2007 | Dorsel et al. |
| RE39,664 E | 5/2007 | Gordon et al. |
| RE39,864 E | 5/2007 | Gordon et al. |
| 7,226,752 B1 | 6/2007 | Roitman |
| 7,238,537 B2 | 7/2007 | Davis et al. |
| 7,238,538 B2 | 7/2007 | Freitag et al. |
| 7,239,394 B2 | 7/2007 | Sharrock et al. |
| 7,244,392 B1 | 7/2007 | Konecke |
| 7,247,500 B2 | 7/2007 | Wei et al. |
| 7,256,053 B2 | 8/2007 | Hu |

(56) References Cited

U.S. PATENT DOCUMENTS

| | | |
|---|---|---|
| 7,270,970 B2 | 9/2007 | Anderson et al. |
| 7,280,201 B2 | 10/2007 | Helbing |
| 7,297,502 B2 | 11/2007 | Gao |
| D557,815 S | 12/2007 | Lee et al. |
| 7,305,896 B2 | 12/2007 | Howell et al. |
| 7,312,027 B2 | 12/2007 | Bachand |
| 7,315,378 B2 | 1/2008 | Phelan et al. |
| 7,317,532 B2 | 1/2008 | Sharrock et al. |
| 7,323,139 B2 | 1/2008 | LaBorde et al. |
| 7,371,582 B2 | 5/2008 | Nahm et al. |
| D570,490 S | 6/2008 | Laverack |
| D571,019 S | 6/2008 | Laverack |
| D571,020 S | 6/2008 | Laverack |
| 7,384,796 B2 | 6/2008 | Davis et al. |
| 7,391,512 B2 | 6/2008 | Fouquet et al. |
| D574,966 S | 8/2008 | Laverack |
| D575,876 S | 8/2008 | Laverack |
| D575,877 S | 8/2008 | Laverack |
| 7,407,813 B2 | 8/2008 | Davis et al. |
| 7,410,768 B2 | 8/2008 | Butlin et al. |
| 7,416,700 B2 | 8/2008 | Buechler et al. |
| D576,737 S | 9/2008 | Lee et al. |
| 7,437,913 B2 | 10/2008 | Djennati et al. |
| 7,438,852 B2 | 10/2008 | Tung et al. |
| 7,459,314 B2 | 12/2008 | Guo et al. |
| 7,459,317 B2 | 12/2008 | Roitman |
| 7,476,549 B2 | 1/2009 | Nahm et al. |
| 7,510,881 B2 | 3/2009 | Ramael et al. |
| 7,516,845 B2 | 4/2009 | Land et al. |
| 7,517,495 B2 | 4/2009 | Wu et al. |
| 7,521,259 B2 | 4/2009 | Petruno et al. |
| 7,521,260 B2 | 4/2009 | Petruno et al. |
| 7,521,560 B2 | 4/2009 | Petruno et al. |
| 7,522,762 B2 | 4/2009 | Rea et al. |
| 7,526,485 B2 | 4/2009 | Hagan et al. |
| D592,759 S | 5/2009 | Laverack |
| 7,532,128 B2 | 5/2009 | Petrilla |
| 7,534,393 B2 | 5/2009 | Catt et al. |
| 7,553,630 B2 | 6/2009 | Langley et al. |
| D597,216 S | 7/2009 | McGuigan et al. |
| 7,588,908 B2 | 9/2009 | Buechler et al. |
| 7,591,791 B2 | 9/2009 | Keren |
| 7,588,9037 | 9/2009 | Buechler et al. |
| D602,599 S | 10/2009 | Xiaowei |
| 7,516,315 B2 | 11/2009 | Sharrock et al. |
| 7,616,315 B2 | 11/2009 | Sharrock et al. |
| 7,625,763 B2 | 12/2009 | Panotopoulos |
| 7,629,178 B2 | 12/2009 | Davis et al. |
| 7,632,460 B2 | 12/2009 | Catt et al. |
| 7,633,620 B2 | 12/2009 | Nahm et al. |
| 7,662,643 B2 | 2/2010 | Wei et al. |
| 7,679,745 B2 | 3/2010 | Claps et al. |
| 7,691,595 B2 | 4/2010 | Fong |
| 7,704,702 B2 | 4/2010 | Keren et al. |
| 7,704,753 B2 | 4/2010 | Tang et al. |
| 7,705,976 B2 | 4/2010 | Robrish |
| 7,713,703 B1 | 5/2010 | Buechler et al. |
| 7,718,443 B2 | 5/2010 | Beesley et al. |
| D617,468 S | 6/2010 | Marquordt et al. |
| 7,741,103 B2 | 6/2010 | Guirguis |
| 7,745,228 B2 | 6/2010 | Schwind et al. |
| 7,763,454 B2 | 7/2010 | Nazareth et al. |
| 7,763,475 B2 | 7/2010 | Klenerman et al. |
| D621,059 S | 8/2010 | Marquordt et al. |
| 7,775,976 B2 | 8/2010 | Fuller et al. |
| 7,784,678 B2 | 8/2010 | Kuo |
| 7,785,899 B2 | 8/2010 | Saul et al. |
| 7,796,266 B2 | 9/2010 | Cohen et al. |
| 7,799,554 B2 | 9/2010 | Mazumdar et al. |
| 7,803,636 B2 | 9/2010 | Gao et al. |
| 7,815,853 B2 | 10/2010 | Nahm et al. |
| 7,815,854 B2 | 10/2010 | Cohen et al. |
| 7,819,822 B2 | 10/2010 | Calasso et al. |
| 7,838,258 B2 | 11/2010 | Yang et al. |
| 7,842,472 B2 | 11/2010 | Valkirs et al. |
| 7,858,396 B2 | 12/2010 | Corstjens et al. |
| 7,863,268 B2 | 1/2011 | Makarov et al. |
| 7,873,939 B2 | 1/2011 | Tian et al. |
| 7,879,624 B2 | 2/2011 | Sharrock |
| 7,879,979 B2 | 2/2011 | Buechler et al. |
| D634,023 S | 3/2011 | We |
| D634,620 S | 3/2011 | Edwards |
| D634,621 S | 3/2011 | Edwards |
| 7,901,949 B2 | 3/2011 | Raj |
| 7,910,309 B2 | 3/2011 | Cary et al. |
| 7,925,445 B2 | 4/2011 | Petrilla et al. |
| 7,939,342 B2 | 5/2011 | Song et al. |
| D639,976 S | 6/2011 | Francis et al. |
| D639,977 S | 6/2011 | Francis et al. |
| D640,389 S | 6/2011 | Francis et al. |
| 7,980,149 B2 | 7/2011 | Godfrey et al. |
| 7,985,560 B2 | 7/2011 | Valkirs et al. |
| 8,017,339 B2 | 9/2011 | Piepenburg et al. |
| 8,022,194 B2 | 9/2011 | Piepenburg et al. |
| 8,024,148 B2 | 9/2011 | Petruno et al. |
| 8,029,982 B2 | 10/2011 | Kingsmore et al. |
| 8,030,000 B2 | 10/2011 | Piepenburg et al. |
| 8,038,965 B2 | 10/2011 | Keren |
| 8,039,783 B2 | 10/2011 | Lai |
| 8,043,867 B2 | 10/2011 | Petruno et al. |
| 8,062,850 B2 | 11/2011 | Piepenburg et al. |
| 8,062,901 B2 | 11/2011 | Dai et al. |
| 8,071,308 B2 | 12/2011 | Piepenburg et al. |
| 8,071,394 B2 | 12/2011 | Wu et al. |
| 8,084,224 B2 | 12/2011 | Buechler et al. |
| 8,114,612 B2 | 2/2012 | Buechler et al. |
| 8,128,871 B2 | 3/2012 | Petruno et al. |
| 8,129,191 B2 | 3/2012 | Sheard et al. |
| 8,153,381 B2 | 4/2012 | Palin et al. |
| D659,847 S | 5/2012 | Li |
| 8,486,717 B2 * | 7/2013 | O'Farrell ............ G01N 33/558 436/514 |
| 9,599,615 B2 * | 3/2017 | O'Farrell ............ B01L 3/5023 |
| 9,851,366 B2 * | 12/2017 | O'Farrell ............ G01N 33/558 |
| 9,874,556 B2 * | 1/2018 | O'Farrell ............ B01L 3/5023 |
| 9,874,576 B2 * | 1/2018 | O'Farrell ............ G01N 33/558 |
| 2003/0028261 A1 | 2/2003 | Petruno et al. |
| 2003/0073121 A1 | 4/2003 | Mendel-Hartvig et al. |
| 2003/0119202 A1 | 6/2003 | Kaylor et al. |
| 2004/0161365 A1 | 8/2004 | Yeung |
| 2005/0221504 A1 | 10/2005 | Petruno et al. |
| 2005/0221505 A1 | 10/2005 | Petruno et al. |
| 2005/0244953 A1 | 11/2005 | Cohen |
| 2006/0019265 A1 | 1/2006 | Song et al. |
| 2006/0040408 A1 | 2/2006 | Jones et al. |
| 2006/0172438 A1 | 8/2006 | Milunic et al. |
| 2006/0199278 A1 | 9/2006 | Leclipteux et al. |
| 2006/0223193 A1 | 10/2006 | Song et al. |
| 2006/0240541 A1 | 10/2006 | Petruno et al. |
| 2007/0048807 A1 | 3/2007 | Song |
| 2007/0141696 A1 | 6/2007 | Baugh et al. |
| 2007/0143035 A1 | 6/2007 | Petruno |
| 2007/0185679 A1 | 8/2007 | Petruno et al. |
| 2007/0211965 A1 | 9/2007 | Helbing et al. |
| 2008/0026281 A1 | 1/2008 | Petruno et al. |
| 2008/0028261 A1 | 1/2008 | Petruno et al. |
| 2008/0069732 A1 | 3/2008 | Yi et al. |
| 2009/0047673 A1 | 2/2009 | Carey |
| 2009/0117006 A1 | 5/2009 | Fernandez |
| 2009/0157023 A1 | 6/2009 | Song et al. |
| 2009/0180925 A1 | 7/2009 | Petruno et al. |
| 2009/0180926 A1 | 7/2009 | Petruno et al. |
| 2009/0180927 A1 | 7/2009 | Petruno et al. |
| 2009/0180928 A1 | 7/2009 | Petruno et al. |
| 2009/0180929 A1 | 7/2009 | Petruno et al. |
| 2009/0214383 A1 | 8/2009 | Petruno et al. |
| 2009/0269858 A1 | 10/2009 | Punyadeera et al. |
| 2009/0311724 A1 | 12/2009 | Levison et al. |
| 2009/0325201 A1 | 12/2009 | Franzmann et al. |
| 2010/0015611 A1 | 1/2010 | Webster et al. |
| 2010/0081148 A1 | 4/2010 | Singbartl et al. |
| 2010/0094564 A1 | 4/2010 | Kuo et al. |
| 2010/0136585 A1 | 6/2010 | Schwind et al. |
| 2010/0143941 A1 | 6/2010 | Wu et al. |

(56) References Cited

U.S. PATENT DOCUMENTS

| | | |
|---|---|---|
| 2010/0165338 A1 | 7/2010 | Claps |
| 2010/0173423 A1 | 7/2010 | Zuaretz et al. |
| 2010/5173423 | 7/2010 | Zuaretz et al. |
| 2010/0239460 A1 | 9/2010 | Nazareth et al. |
| 2010/0240149 A1 | 9/2010 | Nazareth et al. |
| 2010/0255510 A1 | 10/2010 | Wang et al. |
| 2010/0279301 A1 | 11/2010 | Chinnaiyan et al. |
| 2010/0311181 A1 | 12/2010 | Abraham et al. |
| 2011/0003398 A1 | 1/2011 | Mendel-Hartvig et al. |
| 2011/0011959 A1 | 1/2011 | Greenwood et al. |
| 2011/0065136 A1 | 3/2011 | Labrie et al. |
| 2011/0065137 A1 | 3/2011 | Labrie et al. |
| 2011/0065593 A1 | 3/2011 | Labrie et al. |
| 2011/0065598 A1 | 3/2011 | Labrie et al. |
| 2011/0065599 A1 | 3/2011 | Labrie et al. |
| 2011/0065608 A1 | 3/2011 | Labrie et al. |
| 2011/0117540 A1 | 5/2011 | Cary |
| 2011/0124519 A1 | 5/2011 | Falkenberg et al. |
| 2011/0171754 A1 | 7/2011 | Redmond et al. |
| 2011/0244597 A1* | 10/2011 | Tsukada ............... G01N 33/558 436/518 |
| 2012/0142023 A1 | 6/2012 | Ascoli et al. |
| 2012/0184462 A1 | 7/2012 | O'Farrell et al. |
| 2013/0225448 A1 | 8/2013 | O'Farrell et al. |
| 2013/0225449 A1 | 8/2013 | O'Farrell et al. |

FOREIGN PATENT DOCUMENTS

| | | |
|---|---|---|
| CN | 101151531 | 3/2008 |
| CN | 105765384 B | 2/2018 |
| DE | 10 2006 060 066 | 6/2007 |
| DE | 10 2007 010 757 | 9/2007 |
| DE | 10 2007 044 889 | 4/2008 |
| EP | 0 149 168 | 7/1985 |
| EP | 0149168 | 7/1985 |
| EP | 0 250 137 | 12/1987 |
| EP | 0250137 | 12/1987 |
| EP | 0 323 605 | 7/1989 |
| EP | 0323605 | 7/1989 |
| EP | 1 459 068 | 9/2004 |
| EP | 1 582 598 | 10/2005 |
| EP | 1 666 879 | 6/2006 |
| EP | 1459068 B1 | 8/2010 |
| EP | 2 666 018 | 11/2013 |
| EP | 2666018 B1 | 4/2017 |
| GB | 1 526 708 | 9/1978 |
| GB | 1526708 | 9/1978 |
| WO | WO-99/40438 | 8/1999 |
| WO | 9960402 A1 | 11/1999 |
| WO | WO-03/058242 | 7/2003 |
| WO | WO-2005/073733 | 8/2005 |
| WO | WO-2005/090987 | 9/2005 |
| WO | WO-2008/084331 | 7/2008 |
| WO | WO-2012/099897 | 7/2012 |
| WO | WO-2015/038978 | 3/2015 |

OTHER PUBLICATIONS

Email from Elson Silva dated Jul. 19, 2012, 7 pages.
International Search Report and Written Opinion of the International Searching Authority issued for International Patent Application No. PCT/US2012/047493 dated Oct. 1, 2012, 16 pages.
International Search Report and Written Opinion of the International Searching Authority issued for International Patent Application No. PCT/US2012/047497 dated Oct. 15, 2012, 12 pages.
Notification of Granting Patent Right (translation) for CN 201280005790.1, dated Nov. 3, 2015, 2 pages.
Communication pursuant to Rule 114(2) EPC for Application No. 12 709 406.8 dated Dec. 1, 2015.
Response to Office Action for CN 201800467648, filed Feb. 25, 2016, 11 pages.
Communication pursuant to Article 94(3) EPC for EP 12 709 406.8, dated Apr. 18, 2016, 3 pages.
Second Office Action (translation) for CN 201380046764.8, dated May 26, 2016, 3 pages.
Response pursuant to the Communication pursuant to Article 94(3) EPC for EP 12 709 406.8, filed Jun. 27, 2016, 71 pages.
Non-final Rejection for U.S. Appl. No. 13/802,036, dated Jun. 27, 2016, 25 pages.
Response to Non-final Rejection for U.S. Appl. No. 13/802,036, dated Sep. 27, 2016, 16 pages.
Notice of Allowance for U.S. Appl. No. 14/485,283, dated Jul. 8, 2016, 9 pages.
Response to Second Office Action for CN 201380046764.8, filed Sep. 9, 2016, 9 pages.
Request for Continued Examination for U.S. Appl. No. 14/485,283, filed Oct. 7, 2016, 3 pages.
Communication under Rule 71(3) EPC for EP 12 709 406.8, dated Oct. 11, 2016, 95 pages.
Decision to grant for EP 12 709 406.8, dated Mar. 9, 2017, 2 pages.
Final Rejection for U.S. Appl. No. 13/802,036, dated Dec. 23, 2016, 13 pages.
Third Office Action for CN 201380846764.8, dated Jan. 10, 2017, 10 pages.
Notice of Allowance for U.S. Appl. No. 14/485,283, dated Nov. 3, 2016, 9 pages.
Response to Notice of Allowance for U.S. Appl. No. 14/485,283, dated Feb. 3, 2017, 14 pages.
Extended European Search Report for EP 17157319.9, dated Apr. 7, 2017, 9 pages.
Notice of Allowance for U.S. Appl. No. 13/862,301, dated Apr. 7, 2017, 13 pages.
Request for Continued Examination for U.S. Appl. No. 13/862,301, dated Jul. 6, 2017, 3 pages.
Response to Final Office Action for U.S. Appl. No. 13/802,036, dated Mar. 13, 2013, 16 pages.
Notice of Allowance for U.S. Appl. No. 13/802,036, dated Apr. 12, 2017, 7 pages.
Notice of Granting Patent Right for CN 201380046764.8, dated Jun. 2, 2017, 3 pages (includin English translation).
Notice of the First Office Action for CN 201480058016.6, dated Mar. 15, 2017, 9 pages (Including English translation).
Request for Continued Examination for U.S. Appl. No. 13/802,036, dated Jul. 12, 2017, 3 pages.
Notice of Allowance for U.S. Appl. No. 13/802,036, dated Sep. 20, 2017, 7 pages.
Response to First Office Action for CN 201480058016.6, dated Jul. 31, 2017, 72 pages.
Notice of Allowance for CN 201480058016.6, dated Nov. 6, 2017, 5 pages.
International Preliminary Report on Patentability in PCT/US2013/050952, dated Aug. 28, 2014, 10 pages.
Response to Written Opinion with Chapter II Demand and Article 34 Amendments in PCT/US2013/050952, dated May 19, 2014, 17 pages.
Carter et al., "Lateral flow microarrays: a novel platform for rapid nucleic acid detection based on miniaturized lateral flow chromatography," Nucleic Acids Research (2007) 35(10):e74.
Communication pursuant to Article 94(3) EPC for EP 12709406.8, dated Apr. 20, 2015, 5 pages.
Examination Report in European Patent Application No. EP12709406. 8, dated Jul. 16, 2014, 5 pages.
First Office Action in Chinese Patent Application No. 201280005790. 1, dated Oct. 15, 2014, 18 pages (English language summary included).
Gantelius et al., "A lateral flow protein microarray for rapid determination of contagious bovine pleuropneumonia status in bovine serum," J Microbiol Methods (2010) 82(1):11-8.
International Preliminary Report on Patentability for PCT/US14/55520, dated Sep. 30, 2015.
International Preliminary Report on patentability for PCT/US2014/055520, dated Dec. 1, 2014.
Invitation Pursuant to Rule 137(4) EPC in European Patent Application No. EP12709406.8, dated May 21, 2014, 2 pages.
Notice of First Office Action for CN 201380046764.8, dated Oct. 10, 2015.

(56) References Cited

OTHER PUBLICATIONS

Response to Communication pursuant to Art. 94(3) EPC dated Oct. 30, 2015, 10 pages.
Response to Office Action in European Patent Application No. EP12709406.8, dated Mar. 14, 2014, 7 pages.
Response to Rule 137(4) EPC in European Patent Application No. EP12709406.8, dated Jun. 30, 2014, 3 pages.
Response to the First Office Action for CN 201280005790.1, filed Mar. 30, 2015, 27 pages.
Response to Office Action in U.S. Appl. No. 13/343,681, dated Apr. 12, 2013, 8 pages.
Second Office Action (translation) for CN 201280005790.1, dated May 27, 2015, 3 pages.
Summons to attend oral proceedings pursuant to rule 115(1) EPC for Application No. 12 709 406.8, dated Dec. 10, 2015.
Taranova et al., "Integration of lateral flow and microarray technologies for multiplex immunoassay: application to the determination of drugs of abuse," Microchim Acta (2013) 180:1165-1172.
Response to Notice of First Office Action for CN 201380046764.8, filed Feb. 25, 2016, 11 pages.
Notification of Second Office Action for CN 201380046764.8, dated May 26, 2016, 6 pages.
Response to Notification of Second Office Action for CN 201380046764.8, filed Sep. 9, 2016, 9 pages.
Notification of Third Office Action for CN 201380046764.8, dated Jan. 10, 2017, 10 pages.
Response to Notification of Third Office Action for CN 201380046764.8, filed Mar. 27, 2017, 10 pages.
Non-final Rejection for U.S. Appl. No. 13/862,301, dated Jun. 30, 2016, 13 pages.
Response to Non-final Rejection for U.S. Appl. No. 13/862,301, filed Dec. 30, 2016, 17 pages.
Response to Communication pursuant to Article 94(3) EPC for EP 12 709 406.8, filed Jun. 27, 2016, 71 pages.
Non-final Rejection for U.S. Appl. No. 13/862,313, dated Jul. 1, 2016, 13 pages.
Response to Non-final Rejection for U.S. Appl. No. 13/862,313, filed Dec. 30, 2016, 15 pages.
Notice of Allowance for U.S. Appl. No. 13/862,313, dated Apr. 11, 2017, 11 pages.
Notice of Granting Patent Right for CN 201380046764.8, dated Jun. 2, 2017, 3 pages (including English translation).
Request for Continued Examination for U.S. Appl. No. 13/862,313, dated Jul. 7, 2017, 3 pages.
Notice of Allowance for U.S. Appl. No. 13/862,313, dated Sep. 21, 2017, 7 pages.
Broach et al., "High Throughput Screening for Drug Discovery," Nature (1996) 384:14-16.
Burbaum et al., "New Technologies for High-Throughput Screening," Curr. Opin. Chem. Biol. (1997) 1:72-78.
Dictionary definition of "adjacent", Merriam-Webster Online Dictionary (www.m-w.com/dictionary/adjacent), dated Nov. 22, 2005.
"Immunoglobulin D", Wikipedia, the free encyclopedia (en.wikipedia.org/wiki/IgD), dated Feb. 6, 2011.
"Immunoglobulin G", Wikipedia, the free encyclopedia (en.wikipedia.org/wiki/IgG), dated Feb. 6, 2011.
Fernandes, "Letter from the Society President," J. Biomol. Screening (1997) 2:1.
Harlow et al., "Using Antibodies: A Laboratory Manual," p. 8 (Cold Spring Harbor Laboratory Press, Cold Springs Harbor, New York, 1999).
Ilustration from Weiss Patent (U.S. Pat. No. 3,6431,235).
Janzen et al., "High throughput Screening as a Discovery Tool in the Pharmaceutical Industry," Lab Robotics Automation (1996) (8):261-265.
Leuvering et al., "Sole Particle Immunoassay, (SPIA)," J. Immunoassay (1980) 1(1):77-91.
Lexsee 365 F.2D 834, In re Griswold and Pearce, 365 F.2d 834 (1966).
Lexsee 417 F.3E 1369, *Pharmacia Corp. v. PAR Pharmaceutical, Inc.*, 417 F.3d 1369 (2005).
Request for Reexamination and Exhibits 1-5 for U.S. Pat. No. 6,805,837, dated Nov. 23, 2005.
Request for Reexamination and Exhibits 1-5 for U.S. Pat. No. 6,805,838, dated Nov. 23, 2005.
Request for Reexamination and Exhibits 1-3 for U.S. Pat. No. 5,073,484 dated Sep. 26, 2003.
Request for Reexamination and Exhibits 1-8 for U.S. Pat. No. 6,485,982 dated Sep. 15, 2005.
Requester's Reply to Patent Owner's Statement and Exhibits 1-2 for U.S. Pat. No. 6,805,837, dated Feb. 22, 2006.
Requester's Reply to Patent Owner's Statement and Exhibits 1-2 for U.S. Pat. No. 6,805,838, dated Feb. 22, 2006.
Statement by Patent Owner and Exhibits A-D for U.S. Pat. No. 6,805,837, dated Dec. 23, 2005.
Statement by Patent Owner and Exhibits A-D for U.S. Pat. No. 6,805,838, dated Dec. 23, 2005.
Takeda et al., "Experience in Use of Urotrace for Urine of Patients," Rinsho Kensa (Clinical Test) (1974) (original article in Japanese followed by English translation).
ThermoFisher Scientific information sheet entitled "Color-Rich™ Fluoro-Max™ Dyed Microparticles," dated Mar. 2008.
Thermo Scientific instructions sheet entitled DyLight™ Microscale Antibody Labeling Kits,: copyrighted 2010.
Van Hell et al., in *Alternative Immunoassays* (W.P. Collins ed., John Wiley & Sons, 1985), Ch. 4 "Particle Immunoassays," pp. 39-59.
Wood et al., "Base Composition-Independent Hybridization in Tetramethylammonium Chloride: A Method for Oligonucleoticie Screening of Highly Complex Gene Libraries," Proc. Natl. Acad. Sci. USA (1985) 82:1585-1588.
Requirement for Restriction/Election for U.S. Appl. No. 13/343,681, dated Apr. 9, 2012, 6 pages.
Amendment and Response to Restriction Requirement for U.S. Appl. No. 13/343,681, dated Apr. 27, 2012, 9 pages.
Office Action for U.S. Appl. No. 13/343,681, dated Aug. 20, 2012, 12 pages.
Applicant Initiated Interview Request Form for U.S. Appl. No. 13/343,681, dated Nov. 26, 2012, 2 pages.
Office Action for U.S. Appl. No. 13/343,681, dated Dec. 3, 2012, 3 pages.
Statement of Substance of Interview for U.S. Appl. No. 13/343,681, dated Dec. 19, 2012, 2 pages.
Notice of Allowance for U.S. Appl. No. 13/343,681, dated Jan. 14, 2013, 11 pages.
Amendment after Allowance under 37 C.F.R. 1.312 for U.S. Appl. No. 13/343,681, dated Apr. 12, 2013, 8 pages.
Response to Amendment under Rule 312 Communication for U.S. Appl. No. 13/343,681, dated Apr. 25, 2013, 2 pages.
Request for Certificate of Correction, Petition for Correction of Inventorship Pursuant to 37.C.F.R. 1.324(a) and related documents for U.S. Appl. No. 13/343,681, dated Jun. 19, 2015, 30 pages.
Part (A) Response for Certificates of Correction and Part (B) Petition under 37 CFR 1.324 or 37 CFR 1.48 for U.S. Appl. No. 13/343,681, dated Jul. 13, 2015, 1 page.
Certificate of Correction—Post Issue Communication for U.S. Appl. No. 13/343,681, dated Sep. 29, 2015, 1 page.
Office Action for U.S. Appl. No. 13/802,036, dated Jun. 27, 2016, 26 pages.
Amendment in Response to Non-Final Action under 37 C.F.R. 1.111 for U.S. Appl. No. 13/802,036, dated Sep. 27, 2016, 16 pages.
Terminal Disclaimer-Filed(Electronic) for U.S. Appl. No. 13/802,036, dated Sep. 27, 2016, 3 pages.
Terminal Disclaimer-Electronic-Approved for U.S. Appl. No. 13/802,036, dated Sep. 27, 2016, 1 page.
Amendment in Response to Final Office Action under 37 C.F.R. 1.116 for U.S. Appl. No. 13/802,036, dated Mar. 23, 2017, 16 pages.
Terminal Disclaimer-Filed (Electronic) for U.S. Appl. No. 13/802,036, dated Mar. 30, 2017, 2 pages.
Terminal Disclaimer-Electronic-Approved for U.S. Appl. No. 13/802,036, dated Mar. 30, 2017, 1 page.
Notice of Allowance for U.S. Appl. No. 13/802,036, dated Apr. 12, 2017, 9 pages.

(56) References Cited

OTHER PUBLICATIONS

Notice of Allowance for U.S. Appl. No. 13/802,036, dated Sep. 20, 2017, 10 pages.
Notice of Non-Compliant Information Disclosure Statemtn for U.S. Appl. No. 13/802,036, dated Dec. 22, 2017, 1 page.
Non-Final Rejection for U.S. Appl. No. 13/862,301, dated Jun. 30, 2016, 14 pages.
Amendment in Response to Non-Final Office Action under 37 C.F.R. 1.111 for U.S. Appl. No. 13/862,301, dated Dec. 30, 2016, 59 pages.
Notice of Allowance for U.S. Appl. No. 13/862,301, dated Apr. 7, 2017, 15 pages.
Notice of Allowance for U.S. Appl. No. 13/862,301, dated Aug. 24, 2017, 7 pages.
Non-Final Rejection for U.S. Appl. No. 13/862,313, dated Jul. 1, 2016, 14 pages.
Amendment in Response to Non-Final Office Action under 37 C.F.R. 1.111 for U.S. Appl. No. 13/862,313, dated Dec. 30, 2016, 15 pages.
Notice of Allowance for U.S. Appl. No. 13/862,313, dated Apr. 11, 2017, 13 pages.
Notice of Non-Compliant Information Disclosure Statement for U.S. Appl. No. 13/862,313, dated Dec. 26, 2017, 2 pages.
Notice of Allowance for U.S. Appl. No. 14/485,283, dated Jul. 8, 2016, 10 pages.
Amendment under 37 C.F.R. 1.312 for U.S. Appl. No. 14/485,283, dated Feb. 3, 2017, 14 pages.
Response to Amendment under Rule 312 Communication for U.S. Appl. No. 14/485,283, dated Feb. 16, 2017, 2 pages.
Communication pursuant to Rules 16191) and 162 EPC for European patent application EP13 744 903.9, dated Feb. 27, 2015, 2 pages.
Response to the Communication pursuant to Rules 161(1) and 162 EPC for European patent application EP13 744 903.9, dated Sep. 7, 2015, 19 pages.
Communication pursuant to Article 94(3) EPC for European patent application EP13 744 903.9, dated Mar. 9, 2018, 11 pages.
Responsive to the communication pursuant to Article 94(3) EPC for European patent application EP13 744 903.9, dated Sep. 14, 2018, 20 pages.
Communication pursuant to Article 94(3) EPC for European patent application EP13 744 9019, dated Feb. 4, 2020, 7 pages.
Response to the Communication pursuant to Article 94(3) EPC for European patent application EP13 744 9019, dated Aug. 7, 2020, 10 pages.
Claims (mark-up version) for European patent application EP13 744 903.9, dated Aug. 7, 2020, 4 pages.
Communication under Rule 71(3) EPC for European patent application EP14 776 963.2, dated Feb. 7, 2019, 45 pages.
Decision to grant a European patent pursuant to Article 97(1) EPC for European patent application EP14 776 963.2, dated Jun. 24, 2019, 2 pages.
Communication regarding the expiry of the time limit for European patent application EP14 776 963.2, dated Jul. 10, 2020, 1 page.
Extended European Search Report for European patent application EP17 157 319.9, dated Apr. 7, 2017, 9 pages.
Response to the Communication pursuant to Rule 69 EPC and the invitation pursuant to Rule 70a(1) EPC for European patent application EP17 157 319.9, dated Jan. 2, 2018, 25 pages.
Communication pursuant to Article 94(3) EPC for European patent application EP17 157 319.9, dated Mar. 15, 2018, 5 pages.
Response to the Communication pursuant to Art. 94(3) EPC for European patent application EP17 157 319.9, dated Sep. 21, 2018, 18 pages.
Communication pursuant to Article 94(3) EPC for European patent application EP17 157 319.9, dated Dec. 19, 2018, 4 pages.
Response to the Communication pursuant to Article 94(3) EPC for European patent application EP17 157 319.9, dated Jun. 24, 2019, 16 pages.
Communication pursuant to Article 94(3) EPC for European patent application EP17 157 319.9, dated Aug. 12, 2019, 3 pages.
Response to the Communication pursuant to Article 94(3) EPC for European patent application EP17 157 319.9, dated Dec. 16, 2019, 4 pages.
Communication pursuant to Article 94(3) EPC for European patent application EP17 157 319.9, dated Jan. 17, 2020, 4 pages.
Response to the Communication pursuant to Article 94(3) EPC for European patent application EP17 157 319.9, dated May 20, 2020, 15 pages.
Communication pursuant to Article 94(3) EPC for European patent application EP17 157 319.9, dated Oct. 5, 2020, 4 pages.
Amendment under Article 19(1) Response to International Search Report for international patent application PCT/US2012/0021586 (WO2012099897), dated Jun. 19, 2012, 13 pages.
Response Sheet (Claims) for international patent application PCT/US2012/0021586 (WO2012099897), dated Jun. 19, 2012, 10 pages.
International Search Report for international patent application PCT/US2012/0021586 (WO2012099897), dated Apr. 19, 2012, 3 pages.
Written Opinion of the International Searching Authority for international patent application PCT/US2012/0021586 (WO2012099897), dated Jul. 18, 2013, 5 pages.
International Preliminary Report on Patentability for international patent application PCT/US2012/0021586 (WO2012099897), dated Oct. 20, 2014, 29 pages.
International Search Report for international patent application PCT/US2013/050952 (WO2014015076), dated Oct. 17, 2013, 4 pages.
International Preliminary Report on Patentability for international patent application PCT/US2013/050952 (WO2014015076), dated Aug. 23, 2014, 26 pages.
Written Opinion of the International Searching Authority for international patent application PCT/US2013/050952 (WO2014015076), dated Jan. 18, 2015, 7 pages.
International Search Report for international patent application PCT/US2014/055520 (WO2015038978), dated Jan. 12, 2014, 4 pages.
Written opinion of the International Searching Authority for international patent application PCT/US2014/055520 (WO2015038978), dated Mar. 19, 2015, 6 pages.
International Preliminary Report on Patentability for international patent application PCT/US2014/055520 (WO2015038978), dated Sep. 17, 2015, 38 pages.
Fernandes et al,. "Letter from the society president," J. Biomol. Screening (1997) 2:1.
Illustration from Weiss Patent (U.S. Pat. No. 3,6431,235).
International Preliminary Report on Patentability for PCT/US12/21586, dated Mar. 29, 2013.
International Search Report and Written Opinion for PCT/US2012047493, dated Oct. 1, 2012, 16 pages.
International Search Report and Written Opinion for PCT/US2012/047497, dated Oct. 15, 2012, 12 pages.
International Search Report and Written Opinion for PCT/US2013/050952, dated Oct. 17, 2013, 12 pages.
Office Action issued in U.S. Appl. No. 13/343,681, dated Aug. 20, 2012, 11 pages.
Requestor's Reply to Patent Owner's Statement and Exhibits 1-2 for U.S. Pat. No. 6,805,837, dated Feb. 22, 2006.
Requestor's Reply to Patent Owner's Statement and Exhibits 1-2 for U.S. Pat. No. 6,805,838, dated Feb. 22, 2006.
Restriction Requirement issued in U.S. Appl. No. 13/343,681, dated Apr. 9, 2012, 6 pages.
Response to Restriction Requirement in U.S. Appl. No. 13/343,681, dated Apr. 27, 2012, 9 pages.
Wood at al., "Base composition-independent hybridization in tetramethylammonium chloride: a method for oligonucleotide screening of highly complex gene libraries," Proc Natl Acad Sci USA (1985) 82(6):1585-1588.
Wood et al., "Base composition-independent hybridization in tetramethylammonium chloride: a method for oligonucleotide screening of highly complex gene libraries," Proc Natl Acad Sci USA (1985) 82(6):1585-1588.

(56) References Cited

OTHER PUBLICATIONS

Certificate of Invention Patent for Chinese patent application CN201480058016.6, dated Feb. 9, 2018, 2 pages with extra 1 page of English language equivalent or summary.
2nd Office Action for Chinese patent application CN201710694875. X, dated Feb. 5, 2020, 4 pages with extra 3 pages of English language equivalent or summary.
Response to 2nd Office Action for Chinese patent application CN201710694875.X, dated Jul. 9, 2020, 9 pages.
Pending Claims for Chinese patent application CN201710694875. X, dated Jul. 9, 2020, 4 pages.
3rd Office Action for Chinese patent application CN201710694875. X, dated Oct. 19, 2020, 3 pages with extra 3 pages of English language equivalent or summary.
Response to 3rd Office Action for Chinese patent application CN201710694875.X, dated Dec. 22, 2020, 2 pages.
1st Office Action for Chinese patent application CN201810030625. 0, dated Sep. 9, 2019, 7 pages with extra 3 pages of English language equivalent or summary.
Response filed for Chinese patent application CN201810030625.0, dated Mar. 19, 2020, 2 pages.
Amended Claims (clean version) for Chinese patent application CN201810030625.0, dated Mar. 19, 2020, 3 pages.
Amended Claims (mark-up version) for Chinese patent application CN201810030625.0, dated Mar. 19, 2020, 5 pages.
2nd Office Action for Chinese patent application CN201810030625. 0, dated Jul. 29, 2020, 3 pages with extra 3 pages of English language equivalent or summary.
Statement for Chinese patent application CN201810030625.0, dated Aug. 20, 2020, 2 pages.
Claims for Chinese patent application CN201810030625.0, dated Aug. 20, 2020, 3 pages.
Claims (mark-up) for Chinese patent application CN201810030625. 0, dated Aug. 20, 2020, 3 pages.
Pending Claims (mark-up) for Chinese patent application CN201810030625.0, dated Aug. 20, 2020, 3 pages with extra 4 pages of English language equivalent or summary.
Notification of Going through the Formalities of Registration for Chinese patent application CN201810030625.0, dated Sep. 4, 2020, 1 pages.
Notification of Granting Invention Patent Right for Chinese patent application CN201810030625.0, dated Sep. 4, 2020, 2 pages.
Pending Claims (clean) for Chinese patent application CN201810030625.0, dated Sep. 4, 2020, 3 pages.
Pending Claims (mark-up) for Chinese patent application CN201810030625.0, dated Sep. 4, 2020, 4 pages.
Certificate of Invention patent for Chinese patent application CN201810030625.0, dated Dec. 11, 2020, 2 pages with extra 1 page of English language equivalent or summary.
Carter et al., "Lateral flow microarrays: a novel platform for rapid nucleic acid detection based on miniaturized lateral flow chromatography," Nucleic Acids Research, 2007, vol. 35, No. 10, e74, 11 pages doi:10.1093/nar/gkm269.

Burbaum et al., "New technolboies for high-throughput screening," Curr Opin Chem Biol. (1997) 1:72-78.
Illustration from Webs Patent (U.S. Pat. No. 3,6431 ,235).
International Preliminary Report on Patentability for PCT/US14/55520, dated Sep. 30, 2015, 5 pages.
International Search Report and Written Opinion for PCT/US2014/055520, dated Dec. 1, 2014, 11 pages.
Notice of First Office Action for CN 1608207A for Application No. 201380046764.8, dated Oct. 10, 2015.
Office Action in European Patent Application No. EP12709406.8, dated Sep. 6, 2013, 2 pages.
Office Action for U.S. Appl. No. 13/802,036, dated Jun. 27, 2016, 25 pages.
Office Action for U.S. Appl. No. 13/862,301, dated Jun. 30, 2016, 13 pages.
Office Action for U.S. Appl. No. 13/862,313, dated Jul. 1, 2016, 13 pages.
Requestor's Reply to Patent Owner's Statement and Exhibits 1-2 for U.S. Pat. No. 5,605,838, dated Feb. 22, 2006.
Response to Communication pursuant to Art. 94(3) EPC for EP 12 709 406.8, filed Oct. 30, 2015, 10 pages.
Response to Written Opinion for PCT/US2014/055520, filed Jul. 13, 2015, 26 pages.
Response to Office Action for CN 2013800467648, filed Feb. 25, 2016, 11 pages.
ThermoFisher Scientific information sheet entitled "Color-Rich™ Pluoro-Max™ Dyed Microparticles," dated Mar. 2008.
Taranova et al., "Integration of lateral flow and mioroarray technologies for multiplex immunoassay: application to the determination of drugs of abuse," Microchim Acta (2013) 180:1165-1172.
Response to Office Action in European Patent Application No. EP12709406.3, dated Mar. 14, 2014, 7 pages.
Invitation Purusant to Rule 137(4) EPC in European Patent Application No. EP12709406.8, dated May 21, 2014, 2 pages.
Response to Written Opinion with Chapter II Demand and Article 34 Amendments in PCT/US2012/050952, dated May 19, 2014, 17 pages.
International Preliminary Report on Patentability for PCT/US2014/055520, dated Sep. 30, 2015, 5 pages.
Non-final Rejection for U.S. Appl. No. 13/802,036, dated Jun. 27, 2013, 25 pages.
Response to Non-final Rejection for U.S. Appl. No. 13/862,313, dated Dec. 30, 2016, 15 pages.
Third Office Action for CN 201380046764.8, dated Jan. 10, 2017, 10 pages.
Response to Notice of First Office Action for CN 201420058016.6, dated Jul. 31, 2017, 72 pages.
Notification of Granting Invention Patent Right for CN 201420058016. 6, dated Nov. 6, 2017.
International Preliminary Report On Patentability In PCT/US2012/021586, dated Mar. 29, 2013, 29 pages.

* cited by examiner

Direction of Flow

Concentration of binding reagent increases

Direction of Flow

Different binding reagent in each "channel" allows for multiplexing of analyte detection Direction of Flow Direction of Flow FIG. 10A
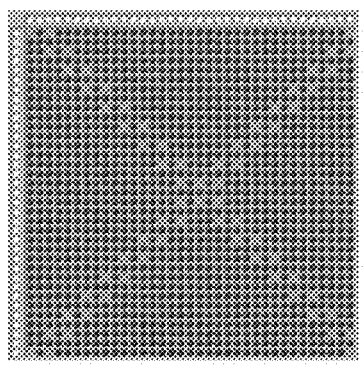
Spots are placed
400um CC.
1 drop = 700pl
FIG. 10B
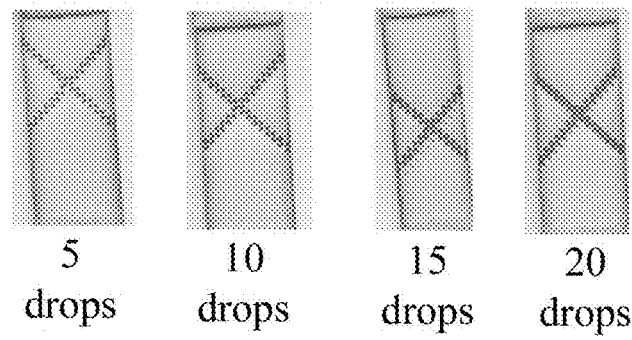
| 5 drops | 10 drops | 15 drops | 20 drops |
FIG. 11A
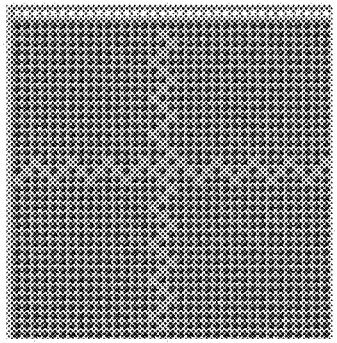
20 drops
200um cc
1 drop + 700pl
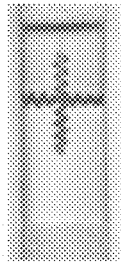
FIG. 11B 20 drops
200um cc
1 drop = 700pl 20 drops
400um cc
1 drop = 700pl Spots are placed
200um CC
1 drop 700pl 5 drops   10 drops   15 drops   20 drops 20 drops
200um CC
1pl = 700pl 20 spots
400um cc
1 spot = 700pl 40ul gold conjugate   60ul gold conjugate   80ul gold conjugate   100ul gold conjugate

FIG. 16A
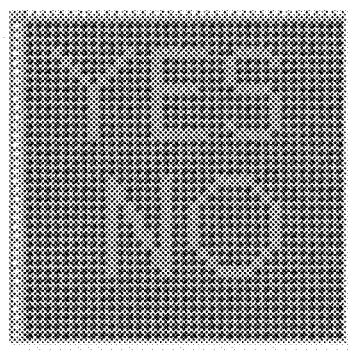
20 drops
200um cc
1 drop = 700pl
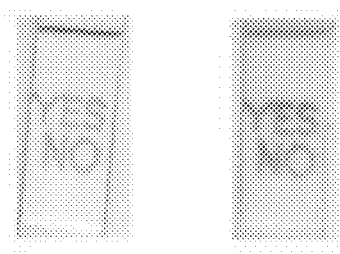
FIG. 16B
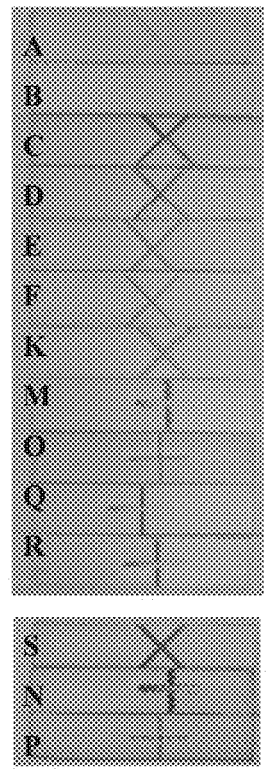
FIG. 17

Direction of Flow

1mm Spacing 0.5mm Spacing 0.35mm Spacing 0.35mm Spacing 0.5mm Zig-Zag Spacing

1mm Zig-Zag Spacing

Direction of Sample Flow anti-Mouse anti-hCG

Running Buffer: 0.1% Tween-20 in PBS

Positive: 0.02IU/mL hCG

Positive: 0.1IU/mL hCG

Positive: 0.5IU/mL hCG

FIG. 20B  anti-Mouse

Running Buffer: 500mM Tris, 0.2% 10G, 0.35% Tween-20, 0.25% PVP-40, pH 8.5 anti-hCG anti-Myoglobin

Positive: 1IU/mL hCG

Positive: 8ug/mL Myoglobin

Positive: 1IU/mL hCG and 8ug/mL Myoglobin

Direction of Sample Flow
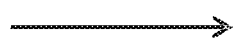
   Negative Result
Positive Result
   Negative Result
Positive Result

LATERAL FLOW ASSAYS USING TWO DIMENSIONAL FEATURES

I. CROSS-REFERENCE TO RELATED APPLICATIONS

This Application is a continuation of application Ser. No. 13/862,313, filed on Apr. 12, 2013, now allowed, which is a divisional of application Ser. No. 13/343,681 filed on Jan. 4, 2012, now U.S. Pat. No. 8,486,717 B2, which claims the priority benefit of U.S. provisional application Ser. No. 61/461,499, filed Jan. 18, 2011. The contents of the above-listed applications are incorporated herein by this reference in their entireties.

II. TECHNICAL FIELD

The present invention relates to novel lateral flow devices using two dimensional features, preferably, uniform two dimensional test and control features, and the methods for detecting an analyte using the lateral flow devices, and processes for making the lateral flow devices.

III. BACKGROUND OF THE INVENTION

Lateral flow assays dominate the non-glucose rapid testing market in humans, and also other areas of application that require rapid generation of a test result, including veterinary diagnostics, agricultural testing, bio-warfare testing and food safety testing, as examples.

The advantages of the lateral flow assay system (LFIA) are well known (see Table 1). Critical among these advantages, is that they represent an appropriate point of care and field use technology that can be brought to market quickly and for a relatively small investment, and be applied over a very broad range of applications.

TABLE 1

Benefits of Lateral Flow Assays in Point of Need Applications

Known and mature technology
Relative ease of manufacture - equipment and processes already developed and available
Easily scalable to high volume production
Stable - shelf lives of 12-24 months often without refrigeration
Ease of use: Minimal operator dependent steps and interpretation
Can handle small volumes of multiple sample types
Can be integrated with onboard electronics, reader systems and information systems Can have high sensitivity, specificity, good stability
Relatively low cost and short timeline for development and approval
Market presence and acceptance - minimal education required for users and regulators Traditionally designed lateral flow assays suffer from performance limitations, most notably low sensitivity and poor reproducibility. Additionally, standard format lateral flow assays produce results in the form of the presence or absence of lines at test and control regions, which have to be interpreted by eye. This subjective interpretation can often be difficult and can lead to incorrect results. These limitations have been exacerbated by the continuing use of traditional development and manufacturing practices, materials, labels, and visual detection systems. The reliance on the generation of linear features such as continuous lines to indicate the presence or absence of analyte in the system is a function of a variety of mechanical factors that can inhibit the reproducible formation of other features on the same substrate. In many instances it is desirable to test for multiple reactions in a single sample (multiplexing). The use of linear features makes multiplexing difficult, makes interpretation of competitive assay results counter-intuitive, and adds to result variability through user error.

Further, quantification and objective read/record technology, often linked to laboratory information systems (LIS) are being implemented at an increasing rate. Demand for multiplexed systems, where detection of more than one analyte is necessary in the same test system is also developing. Current Lateral Flow test systems are generally incompatible with these needs.

The limitations of the current lateral flow assay devices and methods have substantially restricted their application to relatively low specification testing. For more demanding systems requiring high sensitivity, quantification and multiplexing, and for numerous market segments such as military, consumer, environmental or veterinary testing where intuitive, fast, easily interpreted results are required, the current Lateral Flow system is inadequate.

Therefore, there is a need for devices and methods that overcome the limitations of the current technologies and methodologies, that are less subject to interpretation errors, that can produce quantitative results, that are reproducible, that can be multiplexed and that can be applied in numerous market segments. The present invention addresses these and other related needs.

The invention disclosed herein provides for such a device, and discloses methods including but not limited to, methods for manufacturing rapid assays that can produce easily interpreted results in the form of unique indicia, which indicia being representative of the results of the test. The indicia may be standardized symbols visible to the eye or a reader or may be encrypted indicia interpretable by a specialized reader device. The indicia can be developed in any orientation relative to the direction of flow of the assay. The indicia may also indicate qualitative outcomes (positive or negative), semi-quantitative or quantitative outcomes depending upon the assay and reagent design.

Lateral Flow Assay Formats

FIG. 1 shows a typical configuration for such a lateral flow assay. Traditionally designed assays are composed of a variety of materials, each serving one or more purposes, overlapping onto one another, mounted on a backing card using a pressure sensitive adhesive.

The test device consists of several zones, typically constituted by individual segments of different materials, each of which will be briefly explained here. When a test is run, a sample of the material to be tested (sample) is added to the proximal end of the strip, onto a Sample Application Pad. Here, the sample is treated by means of added predetermined reagents to make it compatible with the rest of the test. Liquid phase elements of the treated sample (which may be dissolved, suspended, emulsified or any other liquidized formats) migrate to a next segment of the test device, the Conjugate Pad. Here, a detector reagent has been immobilized, typically consisting of a protein linked passively or covalently to a signal molecule or particle, typically a colloidal gold, or a colored, fluorescent or paramagnetic monodisperse latex particle. The signal reagent can also be another reagent, including non-particulates (e.g., soluble, directly labeled fluorophores gels). This label has been conjugated to one of the specific biological components of the assay, either an antigen or an antibody, depending on the assay format of the specific test device. The liquid phase sample re-mobilizes the dried conjugate material causing it to incorporate into the liquid phase sample material, and analyte in the sample interacts with the conjugate as both migrate into the next section of the test strip, the Reaction Matrix. The reaction matrix is typically a porous membrane with a hydrophilic, open structure for the purposes of transporting liquids to the reagent and control, onto which the other specific biological components of the assay have been immobilized. These are typically proteins, either antibody or antigen, which have been laid down in bands or stripes in specific areas of the membrane where they serve to capture the components of the liquid phase sample, the analyte and conjugate, as they migrate past, through or over the capture lines. Excess liquid phase materials (sample and reagents) continue to migrate across the strip, past the capture lines and are entrapped in a Wick or absorbent pad. Test results are developed on the reaction matrix and are represented as the presence of absence of indicia (typically continuous lines) of captured conjugate which are read either by eye or using a reader device.

Assay formats are often either sandwich (direct) or competitive (competitive inhibition) in nature, and can accommodate qualitative, semi-quantitative, or in certain specific cases, fully quantitative assays.

Direct assay formats are typically used when testing for larger analytes with multiple antigenic sites, such as hCG, Dengue antibody or antigen, or HIV. In this case, a positive result is indicated by the presence of a test line. Some of the conjugated particles will not be captured at the capture line, and will continue to flow toward the second line of immobilized antibodies, the control line. This control line typically comprises a species-specific anti-immunoglobulin antibody, specific for the conjugate antibody on the conjugate.

Competitive assay formats are typically used when performing a test for small molecules with single antigenic determinants, which cannot bind to two antibodies simultaneously. In this format, a positive result is indicated by the absence of a test line on the reaction matrix. A control line should still form, irrespective of the result on the test line. The two formats are illustrated schematically in FIGS. 2a and 2b.

Fluid Transport and Signal Development in Lateral Flow Systems

The function of the current lateral flow test device is based on capillary flow of liquids along the length of the test strip, flowing from the sample introduction pad to the absorbent pad as shown in FIG. 1. Hence the flow geometry and capillary driving force is essentially one dimensional through the reaction matrix, and through the test and control lines. Nitrocellulose membranes are the predominantly used reaction matrix in lateral flow tests. In a lateral flow device the test and control lines are typically made up of proteins but can be other types of biomarker that are bound to the Reaction Matrix in line formats, generally oriented perpendicular to the direction of flow.

An example describing the processing and use of nitrocellulose as the reaction matrix will illustrate the issues with this line format.

Purpose:

The purpose of the reaction matrix in a lateral flow assay is to bind proteins or other capture reagents at the test and control areas, and to maintain their stability and activity over the shelf life of the product. When the test is run, this matrix must accept the conjugate and sample from the conjugate pad, flow them consistently to the reaction area, allow the reaction at the test and control lines to happen and allow excess fluids, label and reactants to exit without binding.

Material:

The material of choice in the vast majority of lateral flow assay systems has historically been nitrocellulose. Several attempts have been made to introduce other material types into the market, including nylon and PVDF membranes, however those attempts have had limited success, apparently due to factors including cost, limited utility, the need for education regarding new chemistry and processing requirements, and inertia due to the large bank of existing experience in the use of nitrocellulose. Other matrices are in development, including plastic materials with controlled contact angles that allow the flow of reactants to occur on the surface of the matrix in a controlled manner.

Nitrocellulose, while extremely functional, may not always be an ideal matrix for an analytical membrane in LFIA's. It does have certain characteristics that make it useful, and it remains the only material that has been successfully and widely applied in this way to date. These characteristics include relatively low cost, true capillary flow characteristics, high protein binding capacity, relative ease of handling (with direct cast, or backed membranes) and a variety of available products with varying wicking rates and surfactant contents. However, the material also possesses a variety of characteristics that make it imperfect for this application. These include imperfect reproducibility of performance within and between lots, shelf life issues, flammability (primarily in unbacked membranes), variable characteristics due to environmental conditions, such as relative humidity, and being subject to breakage (if unbacked), compression and scoring during processing.

As a result of these issues with the material, developers and manufacturers spend a considerable amount of time and effort in optimizing chemistries that overcome some of the inherent material issues, and in developing manufacturing processes that guarantee adequate performance over the entire shelf life of the product. Careful control of the key processes of dispensing, dipping and drying, and attention to chemical and biological treatment of the membrane in order to prevent the introduction of additional variation into the finished product are critical to success.

Flow Characteristics:

In order to function as the reaction matrix in a lateral flow system, the material is typically hydrophilic and has consistent flow characteristics. Nitrocellulose as a base material is hydrophobic, and is made hydrophilic by the addition of rewetting agents during the membrane production process. These rewetting agents are surfactants, and the amount and type of surfactant, and the surfactant addition methods differ from manufacturer to manufacturer and also from brand to brand within a manufacturer. The amount and type of surfactant in the membrane can affect the performance of the assay initially and over time. Not every protein will be compatible with every surfactant. This is one reason for the requirement for screening of multiple membrane types during development. Nitrocellulose membranes' flow characteristics change over time, primarily due to desiccation of the membranes upon storage. Nitrocellulose membranes can be envisaged as a sponge, with the pores of the sponge being held open by water. If that water is removed, the pores collapse, disrupting the ability of the membrane to wick fluids through it. This results in changes and inconsistencies in flowrate over time. As a result, assays based on nitrocellulose can change their performance characteristics over time, as speed directly affects assay sensitivity, and extended run times can result in false positive issues. This is a major contributor to the variability in lateral flow assays.

Critical to the appropriate performance of a lateral flow system is the requirement that the system bind reactants only at the desired locations, namely the test and control lines. The protein binding capacity of a membrane, its interactions with proteins, and the kinetics of the protein binding process are parameters which will determine how one can apply a given set of proteins onto the membrane and how sensitive the resulting diagnostic test will be. Proteins bind to nitrocellulose through a combination of electrostatic, hydrogen and hydrophobic binding. Consistent and reproducible immobilization of immunologically active proteins to test and control lines in lateral flow or flow through assays is one of the key elements to the production of sensitive, reproducible assays.

Membrane Processing:

Nitrocellulose must undergo several processes before integration into the final device, those typically being deposition of test and control line proteins using quantitative dispensers, drying, typically using forced air ovens at elevated temperature, and immersion processes for blocking. To lay down the test and control line proteins, the membrane is striped with protein using either contact or non-contact dispensing systems, and is typically blocked thereafter to control and stabilize flowrates and hydration characteristics, and prevent non-specific binding. The dispensing method used for the test and control lines must be as quantitative as possible, and should not be subject to variation due to variations in the material hydration or absorption characteristics. Non-contact dispensing methods provide the best solution for quantitatively dispensing proteins onto nitrocellulose. The purpose of blocking a nitrocellulose membrane is to prevent binding of proteins and labeled conjugate to the membrane at areas other than the test and control lines, where it can be specifically bound. Blocking also serves other functions, including maintenance of hydration of membranes, modification of wicking rates and stabilization of test and control line proteins. Blocking is typically performed by immersion of the membranes in a solution containing proteins, surfactants and polymers, and is a relatively uncontrolled process. The blocking method must be carefully optimized and controlled to produce optimal performance in the final product over the entire shelf life of the product. Drying is subsequently performed typically by a combination of blocking to remove surface fluids and forced air at elevated temperatures. Again, this drying process must be carefully optimized and controlled to minimize variation in the final product.

This process results in the creation of one or more bound lines of capture reagent across the width of the reaction matrix. When the assay is run, the combination of the bound protein and subsequent formation of a sandwich when reacting with the flowing sample/conjugate increase the flow resistance within the test and control line regions. Resistance to flow can also be increased by the fact that the surfactant in the line has been to some degree driven away from that region by the dispensing process, resulting in a line across the membrane that is more hydrophobic than the areas before and after it, in terms of fluid flow through the matrix.

As a result, in a standard lateral flow configuration, the test and control features perturb the flow of fluid and analyte within the system. One of the primary reasons for the use of test and control lines that span the entire width of the device is to ensure that the perturbation is even across the width of the device and that flow in the longitudinal direction remains even and effectively one-dimensional. This prevents the formation of other more preferred test interpretation features, such as alpha-numeric symbols or quantitative indicia.

Current lateral Flow devices and their associated manufacturing processes impose various limitations on their use, accuracy and reproducibility.

1. Multiplexing is difficult.

a. There is a growing requirement in point of need diagnostics for the generation of assays that can detect more than one analyte in a single device. In a standard configuration, this means dispensing multiple lines perpendicular to the flow direction, separated by distances of 1 or more millimeters. A typical issue seen in multiplexed assays of this nature is "line bleed" where signal generated on one line can "bleed" into the next line, where the conjugate is physically restricted, resulting in the formation of background in the device, which lowers the sensitivity of the assay, and can result in false positives.

b. The dynamics of each assay in the system are different from each of the others. Lateral flow assays are extremely time sensitive assays. The reaction begins as soon as the sample and conjugate mix in the conjugate or sample pad, and continues during migration through the device to the test and control lines. The reaction at the test line occurs quickly, typically in less than 30 seconds. The flow rate of the reactants through the device can be extremely important to the performance of the assay. Flow rate through an analytical membrane, typically nitrocellulose, decreases in a non linear fashion with distance from the origin. As a result, the time taken for the first reaction to reach the first capture line in a multi line assay, and that taken for the reaction to reach the last line, can be significantly different. This has implications for the ability to generate quantitative assays in multiplexed formats.

2. Antibody selection must focus on antibodies with extremely high affinity and "on-rate" ($K_{on}$). This is due to the fact that the reaction at the test line must occur within only a few seconds. This makes antibody selection difficult, and means that laborious selection methods, such as dot blots or lateral flow formats must be used, as against more ergonomic methods such as ELISA, which may select for antibodies with different binding characteristics. This high affinity makes it impossible to evenly develop large diameter features in the direction of flow (including lines, which may show gradation of strength in the direction of flow). The use of smaller features ("pixels") combined appropriately into larger features overcomes this issue.

3. Only a single format of result is generated (a horizontal line). The formation of letters, symbols and lines in any orientation other than perpendicular to the direction of flow in a lateral flow assay is made difficult by the dynamics of flow and conjugate binding in the strip. Two simple examples of the difficulty of generating alternative shapes in a lateral flow system are illustrated in FIGS. 3 and 4 (dot and +).

a. Dot: If binding reagent is dotted onto a membrane, reagent flow and binding characteristics of the binding reagent will result typically in one of three outcomes as shown in FIG. 3: (a) formation of a half moon shape, indicating that conjugate is bound at the leading edge of the dot and the rest of the dot shape does not fill. This indicates a combination of high affinity binding at the leading edge which impedes further flow through the dot, with the remainder of the reagent finding the path of least resistance around the dot; (b) a filled out but generally inconsistent dot, indicating a low affinity binding reagent, which is non optimal for the lateral flow format; and (c) no binding, indicating non specificity of the binding reagent or a negative sample.

b. Plus/Minus: A typical embodiment of this format is one where the control line would show up as the minus and the combined test and control would show up as a plus as shown in FIG. 4. In FIG. 4 is shown the actual development of the plus with the test line dispensed parallel to the 1 dimensional flow. In this case the end of test line closest to the flow introduction shows the highest level of development by the conjugate while the other end shows development only along the edges of the test line. In this case the conjugate does not flow up to the interior of the line due to the high internal flow resistance. The same result would be expected if test and control line positions were swapped in the assay.

4. Interpretation of lines is difficult, particularly in systems that rely on the eye of the user for interpretation. Additionally, lateral flow assays are typically on the order of 2-8 mm wide. The typical analytical membrane is nitrocellulose, which is an inhomogeneous material that is inconsistent both within and between lots. As a result, flow effects are commonly seen that lead to the generation of inconsistent lines across the width of the device. This inhomogeneity in line development can also be created by process-related factors, including poor lamination or cutting. This uneven line development leads to further interpretation issues, and can be particularly difficult for reader systems.

The dominant effect of one dimensional flow is shown schematically in FIGS. 5(a), (b) and (c), where a flow resistance in the form of a spot of dispensed protein is placed in the flow path before the test and control lines using dispensed drops of different volumes in different positions relative to the line. Development of the test line is perturbed directly in line with the placement of the protein spot. Lateral diffusion does occur in the system but can result in even development of the feature that the fluid reaches after the spot only if the distance between the two features is sufficient. The required distance is dependent on the diameter of the spot and the pore size of the membrane, and is generally of a distance that makes the formation of interpretable alpha numeric or other symbols impossible within the working dimensions of a test.

IV. DISCLOSURE OF THE INVENTION

In one aspect, the present disclosure provides for a test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, each of said two reagent dots is neither a reagent line across the entire width of said matrix in a direction perpendicular to the direction of said liquid sample flow nor a complete circle of a reagent line, and after a liquid sample flows laterally along said test device and passes said at least two reagent dots, said at least two reagent dots form a predetermined pattern to indicate presence, absence and/or amount of said analyte in said liquid sample.

In another aspect, the present disclosure provides for a method for detecting an analyte using the above test device. In one exemplary embodiment, the present disclosure provides a method for detecting an analyte in a liquid sample, which method comprises a) contacting a liquid sample with the above test device, wherein the liquid sample is applied to a site of the test device upstream of the at least two of the reagent dots; b) transporting an analyte, if present in the liquid sample, to the at least two of the reagent dots; and c) assessing the presence, absence, amount and/or pattern of signal(s) generated at the at least two of the reagent dots to determining the presence, absence and/or amount of the analyte in the liquid sample. The signal(s) at the reagent dots can be generated by any suitable reactions, such as chemical, biochemical, electrochemical, and/or binding reactions involving the analyte, the reagents located at the reagent dots, reagents added to the liquid sample and/or other reagents dried on the test device before use and are transported by the liquid sample or other liquids to the reagent dots.

In another exemplary embodiment, the signal(s) at the reagent dots can be generated by binding reactions involving the analyte and the reagents located at the reagent dots, and a labeled reagent added to the liquid sample or dried on the test device before use and is transported by the liquid sample or other liquids to the reagent dots. For example, the method comprises a) contacting a liquid sample with the above test device, wherein the liquid sample is applied to a site of the test device upstream of the at least two of the reagent dots; b) transporting an analyte, if present in the liquid sample, and a labeled reagent to the at least two of the reagent dots; and c) assessing the presence, absence, amount and/or pattern of signal(s) generated at the at least two of the reagent dots to determining the presence, absence and/or amount of the analyte in the liquid sample.

In still another aspect, the present disclosure provides for a process for manufacturing a test device for detecting an analyte in a liquid sample, which process comprises forming a plurality of reagent dots on a matrix to make a test device comprising at least two of said reagent dots that do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, wherein each of said two reagent dots is neither a reagent line across the entire width of said matrix in a direction perpendicular to the direction of said liquid sample flow nor a complete circle of a reagent line, and after a liquid sample flows laterally along said test device and passes said at least two reagent dots, said at least two reagent dots form a predetermined pattern to indicate presence, absence and/or amount of said analyte in said liquid sample.

The principles of the present test devices and methods can be applied, or can be adapted to apply, to the lateral flow test devices and assays known in the art. For example, the principles of the present test devices and methods can be applied, or can be adapted to apply, to the lateral flow test devices and assays disclosed and/or claimed in the U.S. Pat. Nos. 3,641,235, 3,959,078, 3,966,897, 4,094,647, 4,168, 146, 4,299,916, 4,347,312, 4,366,241, 4,391,904, 4,425,438, 4,517,288, 4,960,691, 5,141,875, 4,857,453, 5,073,484, 4,695,554, 4,703,017, 4,743,560, 5,075,078, 5,591,645, 5,656,448, RE 38,430 E, U.S. Pat. Nos. 5,602,040, 6,017, 767, 6,319,676, 6,352,862, 6,485,982, 5,120,643, 4,956,302, RE 39,664 E, U.S. Pat. Nos. 5,252,496, 5,514,602, 7,238, 538 B2, 7,175,992 B2, 6,770,487 B2, 5,712,170, 5,275,785, 5,504,013, 6,156,271, 6,187,269, 6,399,398, 7,317,532, EP 0,149,168 A1, EP 0,323,605 A1, EP 0,250,137 A2, GB 1,526,708 and WO99/40438.

V. BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates schematic of a lateral flow test format.

Figure 1:
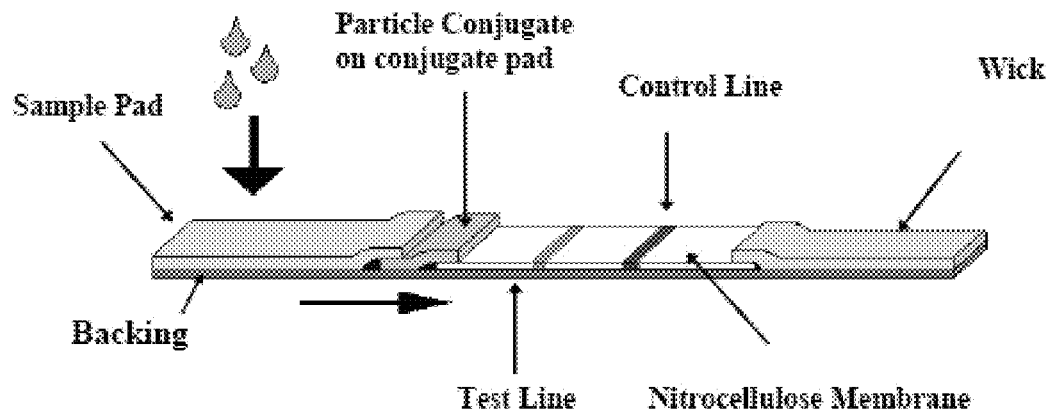
Figure 2A:
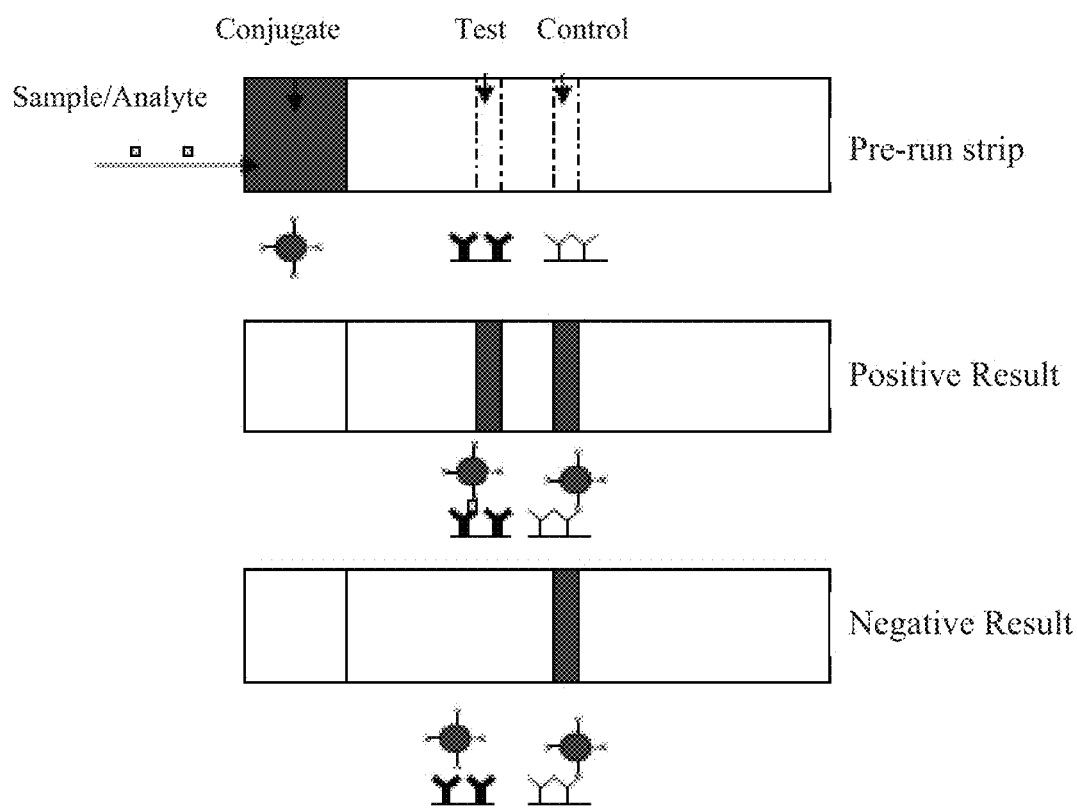
FIG. 2A illustrates schematic of test development in sandwich format.
Figure 2B:
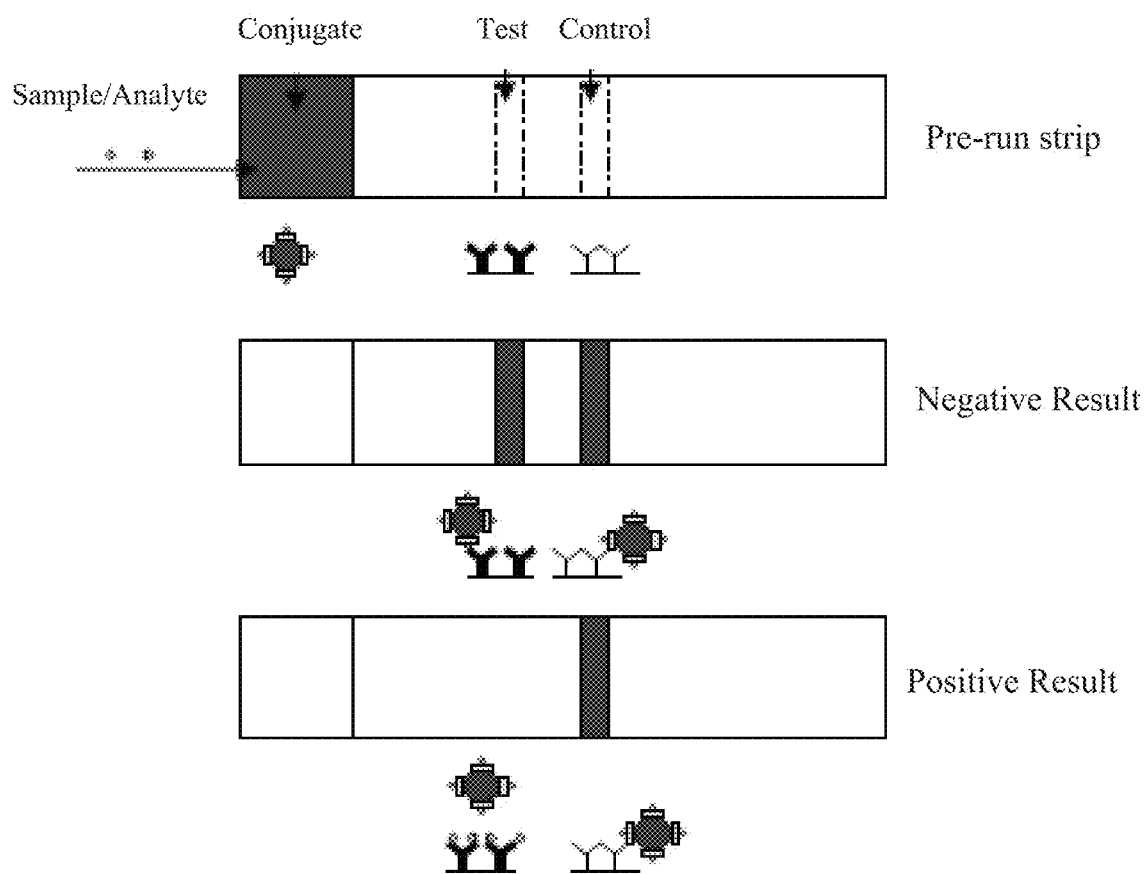
FIG. 2B illustrates schematic of test development in competitive format.
Figures 3A, 3B, 3C:
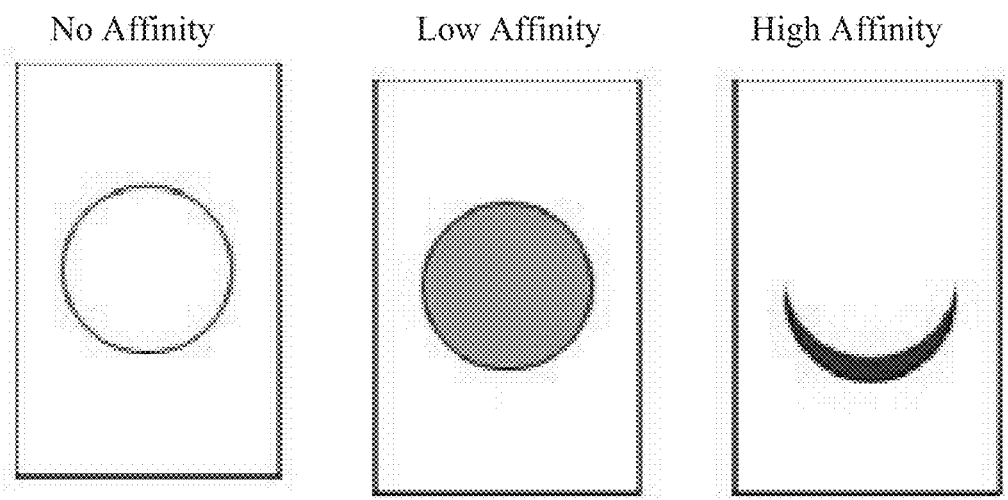

FIG. 3A illustrates schematic of dot development with no affinity capture reagent. FIG. 3B illustrates schematic of dot development with low affinity capture reagent. FIG. 3C illustrates schematic of dot development with capture reagent with high affinity for target.

Figure 4:
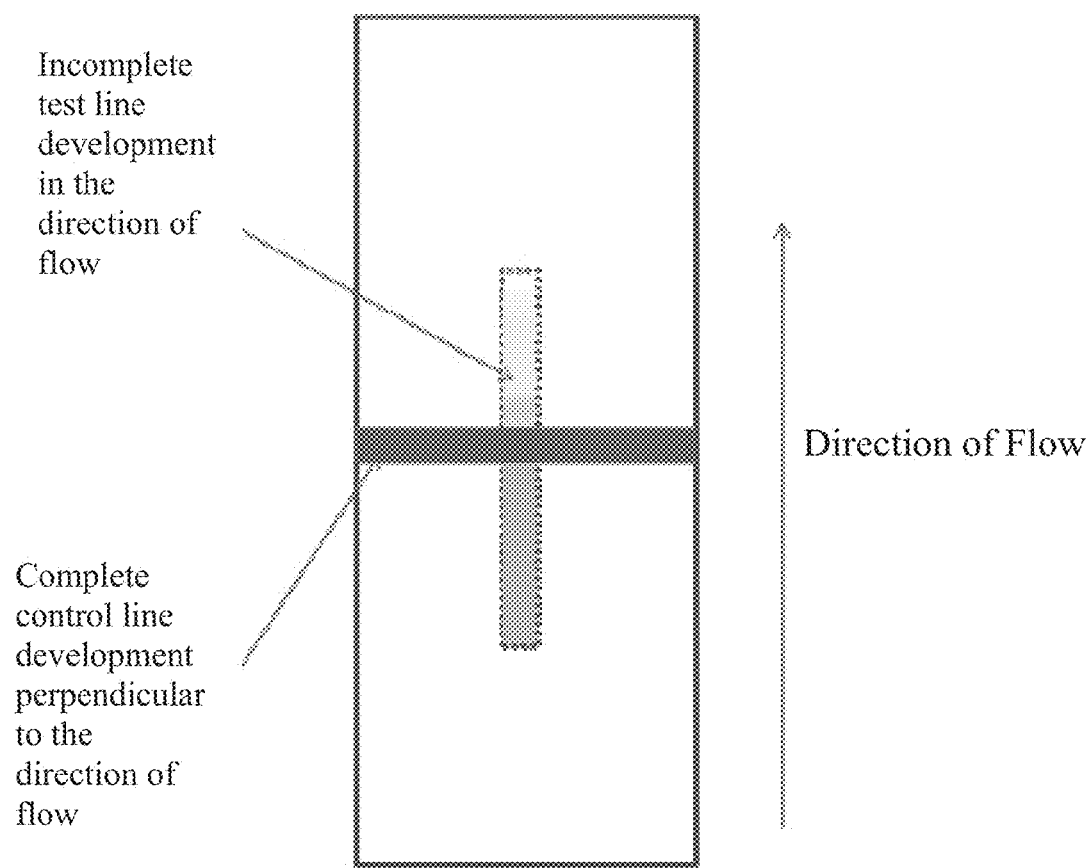

FIG. 4 illustrates schematic of "Plus" sign development with the capture line in the direction of flow with a standard dispensing method. Development of a plus configuration with the test (capture) line parallel to the direction of flow when a single continuous line of reagent is used. Development of the line is incomplete due to perturbation of flow through the binding reagent area.

Figure 5:
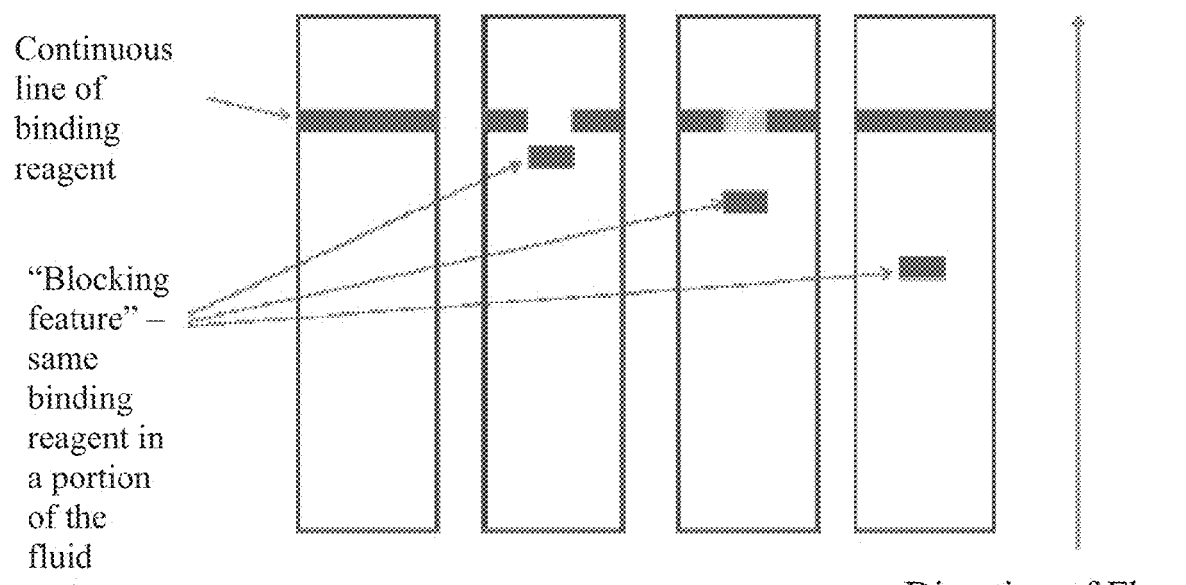

FIG. 5 illustrates schematic of the one dimensional nature of flow in a lateral flow system and the effect of perturbation of flow by placement of a resistance in the flow path. Positioning a binding reagent feature in front of a line of binding reagent demonstrates the linear nature of flow in a lateral flow system. Binding to the blocking feature perturbs fluid flow, forcing fluid around the blockage and preventing the generation of a binding signal in the line of binding reagent behind the blockage. After a certain distance diffusion perpendicular to the direction of flow occurs allowing for some development and finally complete development once the feature is positioned far enough away. The distance required for sufficient lateral diffusion to occur is dependent on the size of the blocking feature and the pore size of the porous material.

Figure 6:
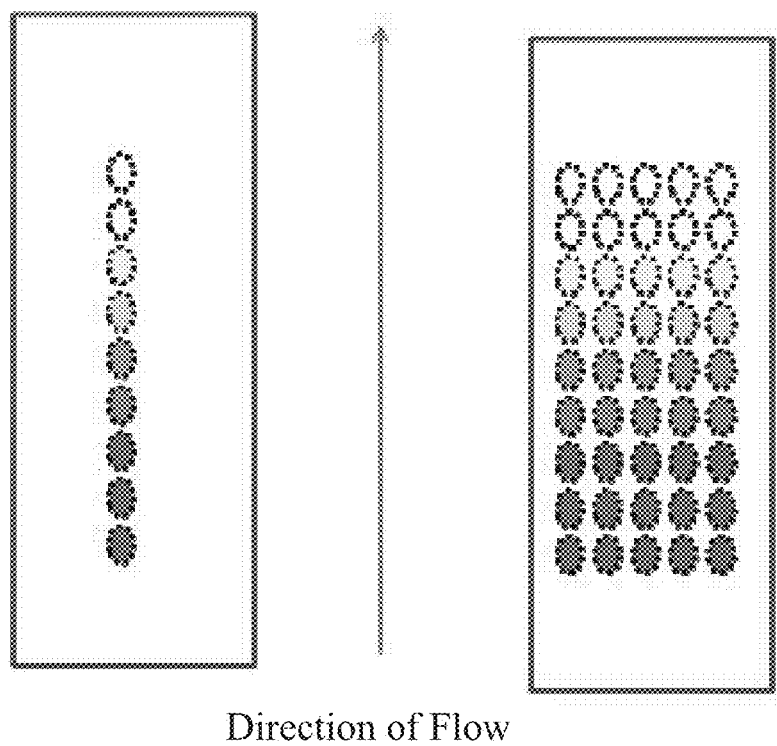

FIG. 6 illustrates schematic of quantification array, 1 dimensional. By placing features of an appropriate size and distance from one another the lateral flow of reagents is not perturbed between features so all features can be exposed evenly to the migrating analyte. This allows for the gradual binding of analyte and depletion of analyte concentration as it moves through the binding region. Changes in binding signal strength further along the flow path are therefore indicative of analyte concentration. This feature can be used to create quantitative thermometer-like results.

Figure 7:
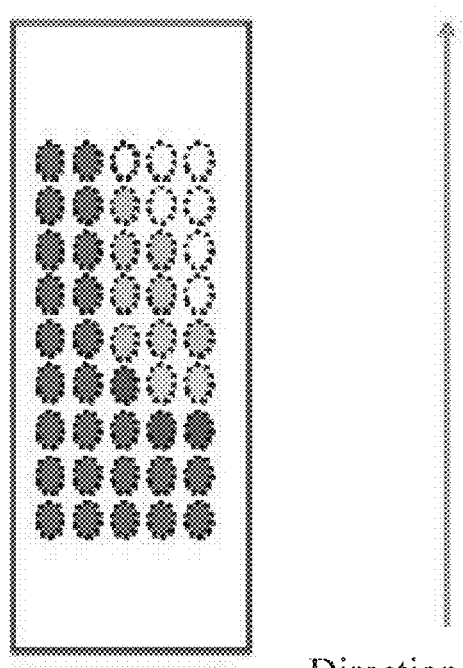
Figure 8:
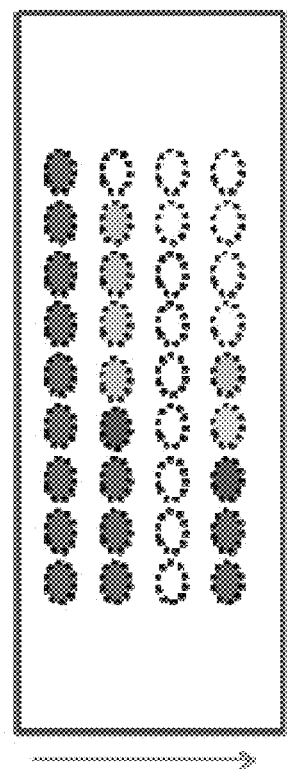

FIG. 7 illustrates schematic of 2-dimensional quantification array. Binding reagent is deposited in the flow path as pixels in two dimensions. The concentration of the binding reagent is the same in all pixels in the direction of flow, but the concentration changes in each row perpendicular to the direction of flow. The system acts to quantify in the same manner as in FIG. 6, however, the titration of the binding reagent in the second dimension allows for the generation of a greater dynamic range in the assay FIG. 8 illustrates schematic of multiplex array (4 analyte). Different binding reagents in each "channel" allows for multiplexing of analyte detection.

Figure 9:
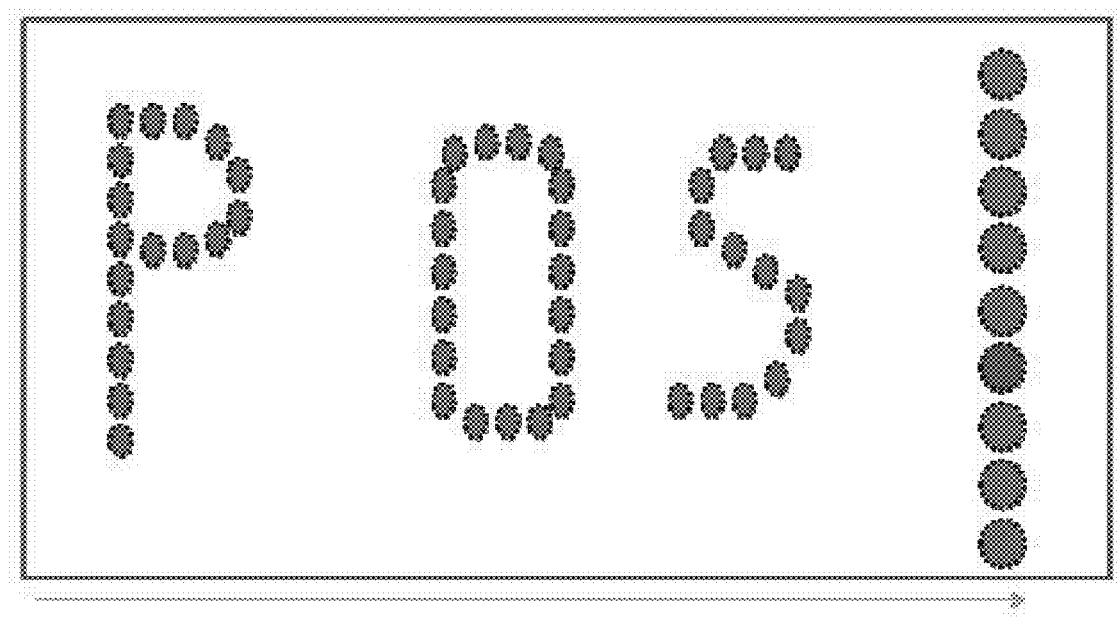

FIG. 9 illustrates an exemplary alpha numeric pixel array. Array can be printed in any orientation, allowing for the creation of alpha-numeric results.

FIGS. 10A and 10B illustrate programmed and actual images of an exemplary signal readout. FIG. 10A illustrates programmed "X" symbol. FIG. 10B illustrates "X" symbol obtained from an actual test.

FIGS. 11A and 11B illustrate programmed and actual images of an exemplary signal readout. FIG. 11A illustrates programmed "+" symbol. FIG. 11B illustrates "+" symbol obtained from an actual test.

Figure 12A:
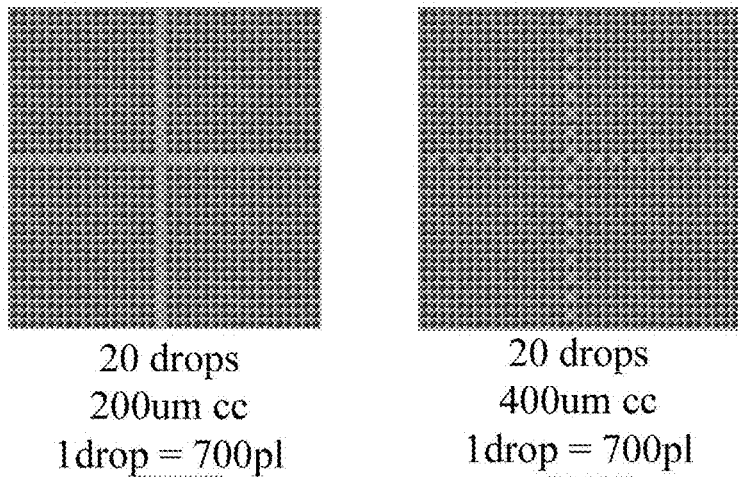
Figure 12B:

FIGS. 12A and 11B illustrate programmed and actual images of another exemplary signal readout. FIG. 12A illustrates programmed "+" symbol. FIG. 12B illustrates "+" symbol obtained from an actual test.

Figure 13A:
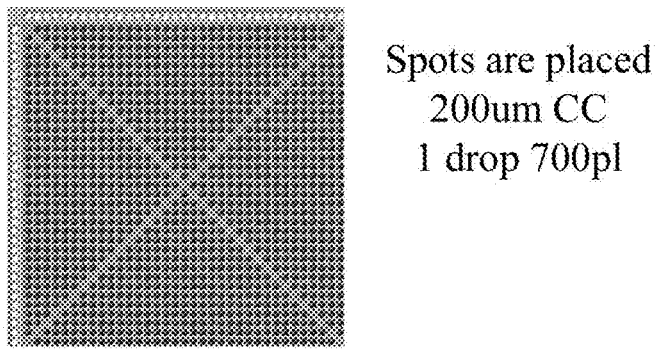
Figure 13B:
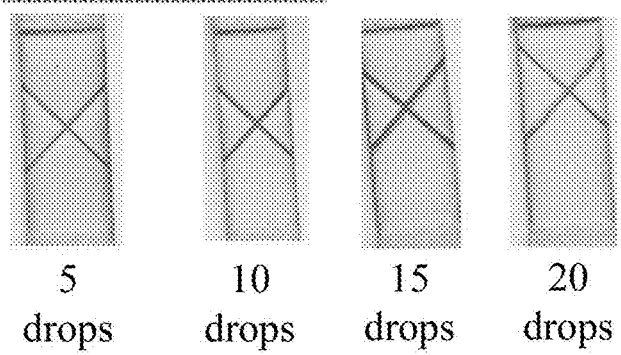

FIGS. 13A and 13B illustrate programmed and actual images of an exemplary signal readout. FIG. 13A illustrates programmed "X" symbol. FIG. 13B illustrates "X" symbol obtained from an actual test.

Figure 14A:
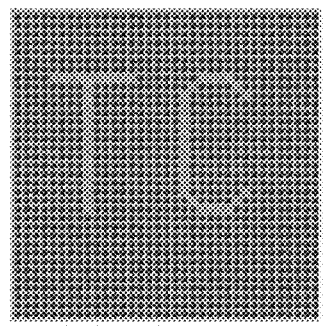
Figure 14B:
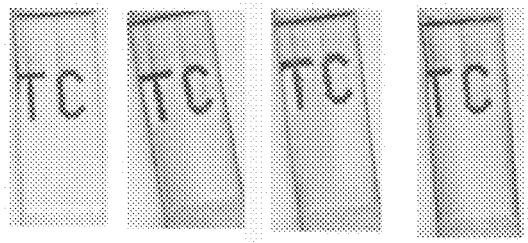

FIGS. 14A and 14B illustrate programmed and actual images of an exemplary signal readout. FIG. 14A illustrates programmed "TC" symbol. FIG. 14B illustrates "TC" symbol obtained from an actual test.

Figure 15A:
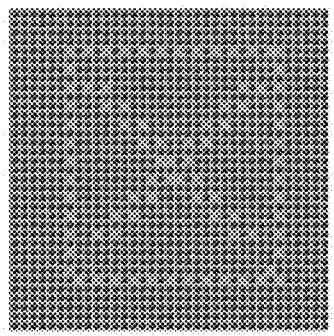
Figure 15B:
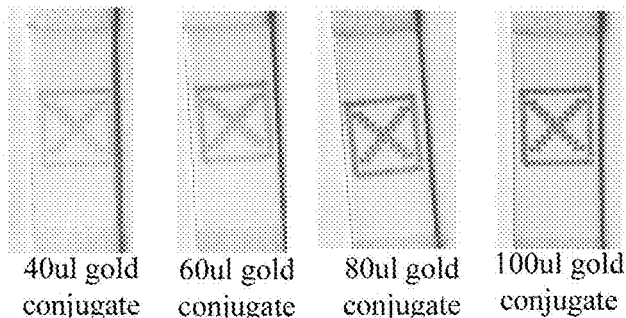

FIGS. 15A and 15B illustrate programmed and actual images of an exemplary signal readout. FIG. 15A illustrates another programmed "X" (within a box) symbol. FIG. 15B illustrates "X" (within a box) symbol obtained from an actual test.

FIGS. 16A and 16B illustrate programmed and actual images of an exemplary signal readout. FIG. 16A illustrates another programmed "YES" and "NO" symbol. FIG. 15B illustrates "YES" and "NO" symbol obtained from an actual test.

FIG. 17 illustrates various symbols obtained from actual tests for improving the clarity of signals.

Figure 18:
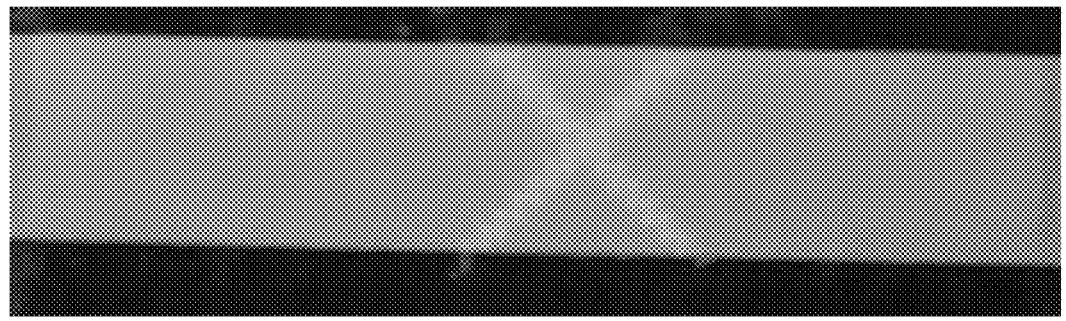
Figure 19A:
Figure 19B:
Figure 19C:
Figure 19D:
Figure 19E:
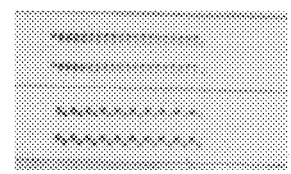
Figure 20A:
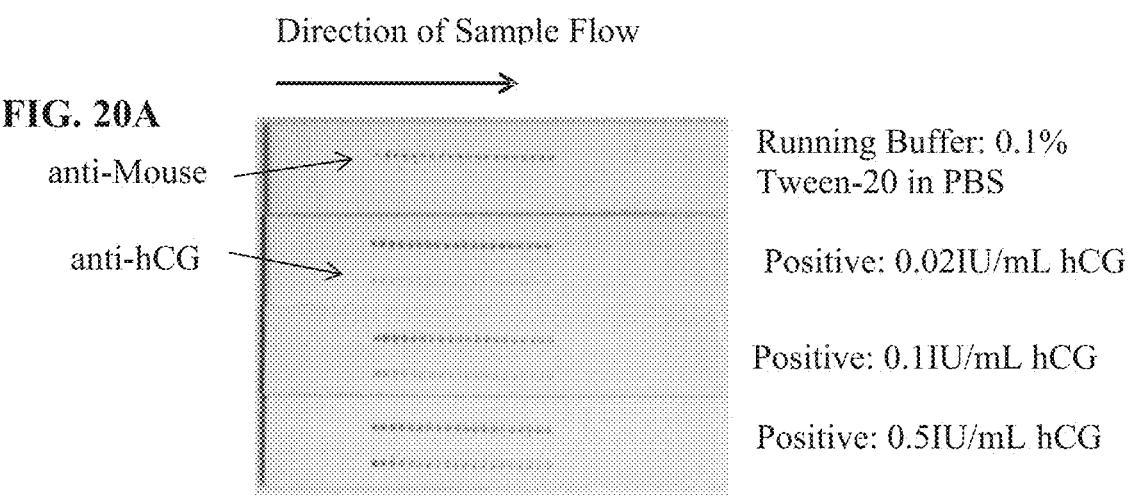
Figure 20A:
Figure 20C:
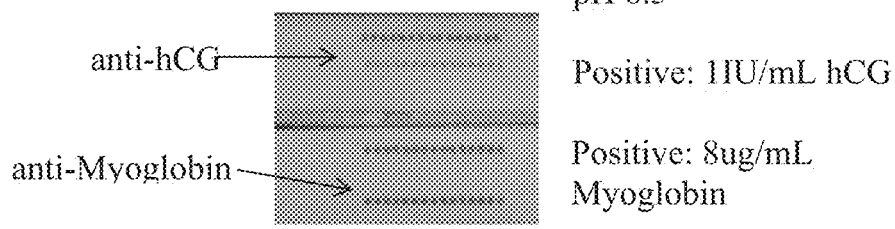
Figure 20D:
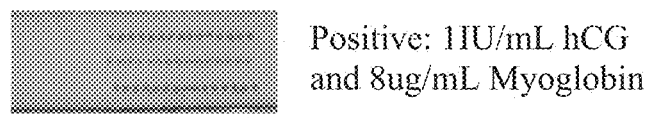
Figure 21A:
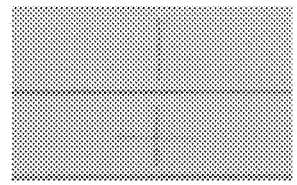
Figure 21B:
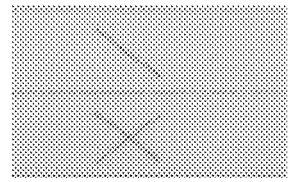
Figure 21C:
Figure 21D:
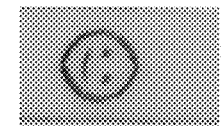

FIG. 18 illustrates "X" symbol obtained from actual tests using a fluorescent label (Europium).

FIGS. 19A-19E illustrate optimization of signal development using the "pixel" concept for lateral flow assays.

FIGS. 20A-20D illustrate applications of the "pixel" concept in multiplexed lateral flow assays.

FIGS. 21A-21D illustrate construction of various spot patterns using a smaller dispense volume.

VI. DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "the line is substantially parallel to the liquid sample flow direction" means that the angle between the line and the liquid sample flow direction is at least less than 45 degrees or more than 135 degrees. In some specific embodiments, the angle between the line and the liquid sample flow direction is at about 40, 35, 30, 25, 20, 15, 10, 5, 4, 3, 2, or 1 degree, or the line is completely parallel to the liquid sample flow direction. In other specific embodiments, the angle between the line and the liquid sample flow direction is at about 140, 145, 150, 155, 160, 165, 170, 175, 176, 177, 178, or 179 degrees, or the line is completely parallel to the liquid sample flow direction.

As used herein, "the line is substantially perpendicular to the liquid sample flow direction" means that the angle between the line and the liquid sample flow direction is at least more than 45 degrees or less than 135 degrees. In some specific embodiments, the angle between the line and the liquid sample flow direction is at about 50, 55, 60, 65, 70, 75, 80, 85, 86, 87 88 or 89 degrees, or the line is completely perpendicular to the liquid sample flow direction. In other specific embodiments, the angle between the line and the liquid sample flow direction is at about 130, 125, 120, 115, 110, 105, 100, 95, 94, 93, 92 or 91 degrees, or the line is completely perpendicular to the liquid sample flow direction.

As used herein, "reagent dots have substantially the same size or diameter" means that the difference in the size or diameter between the largest dot and smallest dot is not more than one fold or less than 50% of the average or median size or diameter of the reagent dots. In some specific embodiments, the difference in the size or diameter between the largest dot and smallest dot is within 45%, 40%, 30%, 20%, 10%, 5%, or 1% of the average or median size or diameter of the reagent dots. In other specific embodiments, reagent dots have the same size or diameter.

As used herein, "the distance between reagent dots is substantially the same" means that the distance between or among reagent dots, often adjacent reagent dots, is within 50% variation of the average or median distance between or among reagent dots or adjacent reagent dots. In some specific embodiments, the distance between or among reagent dots or adjacent reagent dots is within 45%, 40%, 30%, 20%, 10%, 5%, or 1% variation of the average or median distance between or among reagent dots or adjacent reagent dots. In other specific embodiments, the distance between or among reagent dots is the same. Such space or distance can be measured by any suitable means. In some specific embodiments, the space or distance between or among reagent dots is measured as the space or distance between or among the edges of the reagent dots or adjacent reagent dots. In other specific embodiments, the space or distance between or among reagent dots is measured as the space or distance between or among the centers or effective centers of the reagent dots or adjacent reagent dots.

As used herein, a "binding reagent" refers to any substance that binds to target or analyte with desired affinity and/or specificity. Non-limiting examples of the binding reagent include cells, cellular organelles, viruses, particles, microparticles, molecules, or an aggregate or complex thereof, or an aggregate or complex of molecules. Exemplary binding reagents can be an amino acid, a peptide, a protein, e.g., an antibody or receptor, a nucleoside, a nucleotide, an oligonucleotide, a nucleic acid, e.g., DNA or RNA, a vitamin, a monosaccharide, an oligosaccharide, a carbohydrate, a lipid, an aptamer and a complex thereof As used herein, "antibody" includes not only intact polyclonal or monoclonal antibodies, but also fragments thereof (such as Fab, Fab', F(ab')$_2$, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class As used herein, "monoclonal antibody" refers to an antibody obtained from a population of substantially homogeneous antibodies, i.e., the antibodies comprising the population are identical except for possible naturally occurring mutations that are present in minor amounts. As used herein, a "monoclonal antibody" further refers to functional fragments of monoclonal antibodies.

As used herein, the term "specifically binds" refers to the specificity of a binding reagent, e.g., an antibody, such that it preferentially binds to a defined analyte or target. Recognition by a binding reagent or an antibody of a particular analyte or target in the presence of other potential targets is one characteristic of such binding. In some embodiments, a binding reagent that specifically binds to an analyte avoids binding to other interfering moiety or moieties in the sample to be tested.

As used herein the term "avoids binding" refers to the specificity of particular binding reagents, e.g., antibodies or antibody fragments. Binding reagents, antibodies or antibody fragments that avoid binding to a particular moiety generally contain a specificity such that a large percentage of the particular moiety would not be bound by such binding reagents, antibodies or antibody fragments. This percentage generally lies within the acceptable cross reactivity percentage with interfering moieties of assays utilizing the binding reagents or antibodies directed to detecting a specific target. Frequently, the binding reagents, antibodies or antibody fragments of the present disclosure avoid binding greater than about 90% of an interfering moiety, although higher percentages are clearly contemplated and preferred. For example, binding reagents, antibodies or antibody fragments of the present disclosure avoid binding about 91%, about 92%, about 93%, about 94%, about 95%, about 96%, about 97%, about 98%, about 99%, and about 99% or more of an interfering moiety. Less occasionally, binding reagents, antibodies or antibody fragments of the present disclosure avoid binding greater than about 70%, or greater than about 75%, or greater than about 80%, or greater than about 85% of an interfering moiety.

As used herein, "mammal" refers to any of the mammalian class of species. Frequently, the term "mammal," as used herein, refers to humans, human subjects or human patients.

As used herein, the term "subject" is not limited to a specific species or sample type. For example, the term "subject" may refer to a patient, and frequently a human patient. However, this term is not limited to humans and thus encompasses a variety of mammalian species.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "stringency" of nucleic acid hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Current Protocols in Molecular Biology (Ausubel et al. eds., Wiley Interscience Publishers, 1995); Molecular Cloning: A Laboratory Manual (J. Sambrook, E. Fritsch, T. Maniatis eds., Cold Spring Harbor Laboratory Press, 2d ed. 1989); Wood et al., Proc. Natl. Acad. Sci. USA, 82:1585-1588 (1985).

As used herein the term "isolated" refers to material removed from its original environment, and is altered from its natural state. For example, an isolated polypeptide could be coupled to a carrier, and still be "isolated" because that polypeptide is not in its original environment.

As used herein, "test substance (or candidate compound)" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on a target is determined by the disclosed and/or claimed methods herein.

As used herein, high-throughput screening (HTS) refers to processes that test a large number of samples, such as samples of diverse chemical structures against disease targets to identify "hits" (see, e.g., Broach, et al., High throughput screening for drug discovery, Nature, 384:14-16 (1996); Janzen, et al., High throughput screening as a discovery tool in the pharmaceutical industry, Lab Robotics Automation: 8261-265 (1996); Fernandes, P. B., Letter from the society president, J. Biomol. Screening, 2:1 (1997); Burbaum, et al., New technologies for high-throughput screening, Curr. Opin. Chem. Biol., 1:72-78 (1997)). HTS operations are highly automated and computerized to handle sample preparation, assay procedures and the subsequent processing of large volumes of data.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

B. Lateral Flow Devices Using Two Dimensional Features

In one aspect, the present disclosure provides for a test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, each of said two reagent dots is neither a reagent line across the entire width of said matrix in a direction perpendicular to the direction of said liquid sample flow nor a complete circle of a reagent line, and after a liquid sample flows laterally along said test device and passes said at least two reagent dots, said at least two reagent dots form a predetermined pattern to indicate presence, absence and/or amount of said analyte in said liquid sample.

Numerous variables can be considered to make the test device to ensure that the reagent dots do not overlap and are sufficiently spaced apart from each other so that liquid sample flow to, through and/or around one reagent dot or set of reagent dots does not substantially affect flow of the liquid sample flow to, through and/or around other reagent dot or other sets of reagent dots. And at the same time, the test device should comprise sufficient number of the reagent dots that can be used in generating signal readout to indicate presence, absence and/or amount of said analyte in said liquid sample. Exemplary variables that can be considered and/or adjusted in making the test device include the number of reagent dots, the size and/or shape of the reagent dots, e.g., whether the absolute size or the size relative to the size of the matrix, the types and amounts of the reagents located at the reagent dots, the spacing between or among a portion or all reagent dots on the test device, e.g., whether the absolute size of the spacing or the size of the spacing relative to the size of the matrix and/or the number of the reagent dots on the matrix, the orientation or position of the reagent dots relative to the liquid sample flow direction, the uniformity or variations of the sizes and/or shape among the reagent dots and the properties of the matrix, e.g., the material and/or porosity of the matrix, and/or the properties or composition of the solution in which the reagent is spotted. Some or all of these variables can be tested, adjusted or determined to make a test device that meets the intended test performance, e.g., meeting the intended or desired assay sensitivity and/or specificity.

In some specific embodiments, it can be determined that the reagent dots do overlap and are not sufficiently spaced apart from each other so that liquid sample flow to, through and/or around one reagent dot or set of reagent dots blocks or prevents flow of the liquid sample flow to, through and/or around other reagent dot or other sets of reagent dots. Some or all of these variables can then be adjusted so that the liquid sample flow blocking effect be reduced by at least 10%, and preferably by at least 20%, 30%, 40%, 50%, 60%, 70%, 80%, 90%, 95%, 96%, 97%, 98%, 99%, or 100%. In other specific embodiments, given a particular configuration, the liquid sample flow to, through and/or around other reagent dot or other sets of reagent dots can be determined. Some or all of these variables can then be adjusted so that the liquid sample flow to, through and/or around other reagent dot or other sets of reagent dots be increased by at least 10%, and preferably by at least 20%, 30%, 40%, 50%, 60%, 70%, 80%, 90%, 95%, 96%, 97%, 98%, 99%, or 100%. In other embodiments, some or all of these variables can then be adjusted so that the liquid sample flow to, through and/or around other reagent dot or other sets of reagent dots be increased by 1 fold, 2 folds, 3 folds, 4 folds, 5 folds 6 folds, 7 folds, 8 folds, 9 folds, 10 folds, or more.

The test device can comprise any suitable number of reagent dots. In one example, the test device comprises two reagent dots. In another example, the test device comprises more than two reagent dots, such as at least 3, 4, 5, 6, 7, 8, 9, 10, 50, 100, 500, 1,000, 5,000, 10,000 or more reagent dots.

Any suitable number, portion or all of the reagent dots in the test device can be sufficiently spaced apart from each other. For example, at least a quarter, a third, half or all reagent dots do not overlap and are sufficiently spaced apart from each other so that when the liquid sample flows laterally along the matrix, flow of the liquid sample to, through and/or around one of the reagent dots does not substantially affect flow of the liquid sample to, through and/or around the other reagent dots.

The predetermined pattern formed at the reagent dots can take any form, shape and/or pattern. For example, the predetermined pattern can be a line, multiple lines, a symbol, a geometric shape and an alpha-numeric shape, a regular shape, or an irregular shape, or a combination thereof. The exemplary regular shape can be a line, a circle, a rod, a square, a triangle, and a rectangle. The exemplary alpha-numeric shape can be a letter, a word, a number or a combination thereof.

When the predetermined pattern is in the form of a line or multiple lines, the line(s) can be at any suitable orientation or position relative to the liquid sample flow direction. In one example, the line(s) is substantially parallel to the liquid sample flow direction. In another example, the line(s) is substantially perpendicular to the liquid sample flow direction. In still another example, the predetermined pattern is in the form of multiple lines. The multiple lines can comprise at least a line that is substantially parallel to the liquid sample flow direction and at least a line that is substantially perpendicular to the liquid sample flow direction. In some embodiments, at least a quarter, a third, half of the lines are substantially parallel to the liquid sample flow direction. In other embodiments, at least a quarter, a third, half of the lines are substantially perpendicular to the liquid sample flow direction.

The test device can be used to detect a single analyte or multiple analytes in a liquid sample. In one example, the plurality of reagent dots in the test device comprises different reagents and the test device is used to detect multiple analytes in the liquid sample. In another example, the plurality of reagent dots in the test device comprises the same reagent and the test device is used to detect the amount of a single analyte in the liquid sample.

The reagent dots in the test device can comprise any suitable amount of the reagent(s). In one example, the plurality of reagent dot comprises the same amount of the reagent(s). In another example, the plurality of reagent dots comprises the different amounts of the reagent(s).

The reagent dots in the test device can have any suitable size(s). In one example, at least one of the reagent dots has a diameter of about 0.1-1 um, 1-10 um, 10-50 um, 51-100 um, 101-200 um, 201-300 um, 301-400 um, 401-500 um and 501-1000 um. In another example, at least a quarter, a third, half or all reagent dots have a diameter of about 0.1-1 um, 1-10 um, 10-50 um, 51-100 um, 101-200 um, 201-300 um, 301-400 um, 401-500 um or 501-1000 um. In still another example, at least one of the reagent dots has a diameter or surface area that is about 10%, 5%, 1%, 0.5%, 0.1%, 0.05%, 0.01%, 0.001% or smaller diameter or surface area of the length, width or surface area of the matrix calculated by the width and length of the membrane. In yet another example, at least a quarter, a third, half or all reagent dots have a diameter or surface area that is about 10%, 5%, 1%, 0.5%, 0.1%, 0.05%, 0.01%, 0.001% or smaller diameter or surface area of the length, width or surface of the matrix.

Any suitable drop volumes can be used to make spots with any suitable or desirable sizes. In exemplary embodiments, the range of drop volumes used to create the range of spot sizes on the flow membrane can be in the range of about 30-200 pL, 201-500 pL, 501 pL-1.001 nL, 1.001 nL to 5.0 nL, 5.1-25 nL, 21.1-100 nL, or 100.1-500 nL. Shown in the below Table 1 is both spherical and hemispherical diameter of various drop sizes in the above drop range.

TABLE 1

| Drop Volume | Sphere Diameter (um) | Hemisphere Size (um) |
| --- | --- | --- |
| 1 pL | 12.4 | 15.3 |
| 10 | 26.7 | 33.8 |
| 100 | 58 | 72 |
| 500 | 98 | 124 |
| 1 nL | 124 | 156 |
| 2.08 | 158 | 199 |
| 5 | 212 | 268 |
| 10 | 266 | 337 |
| 20 | 336 | 423 |
| 50 | 457 | 577 |
| 100 | 575 | 725 |
| 500 | 982 | 1243 |

The actual developed spot size of a reagent drop on the membrane can be larger, e.g., about 10-25% larger, than the hemispherical drop diameter. The sphere and hemispherical size of different drop volumes with the range described above is shown in the above Table 1.

The meaning of a "diameter" is often determined by the shape of the dot. For example, if the dot is a circle, the diameter of a circle is any straight line segment that passes through the center of the circle and whose endpoints are on the circle. The length of a diameter is also called the diameter. For a convex shape in the plane, the diameter is defined to be the largest distance that can be formed between two opposite parallel lines tangent to its boundary. The use of "diameter" does not limit the dot shape to be a circle or other regular shape. In some specific embodiments, when a dot has an irregular shape, a "diameter" can be measured as a parameter that indicates the length or width of the dot, e.g., measured as the largest distance between two points on the dot.

The reagent dots in the test device can have the same or different size(s) or diameter(s). In one example, at least a quarter, a third, half or all reagent dots have substantially the same size or diameter. In another example, at least a quarter, a third, half or all reagent dots have substantially different sizes or diameters.

The reagent dots in the test device can have any suitable shapes, e.g., any suitable regular or irregular shape. In one example, at least one of the reagent dots has a shape that is a line, a circle, a rod, a square, a triangle, a rectangle or an irregular shape. In another example, at least a quarter, a third, half or all reagent dots have a shape that is a line, a circle, a rod, a square, a triangle, a rectangle or an irregular shape. The reagent dots in the test device can have the same or different shape(s). In one example, at least a quarter, a third, half or all reagent dots have the same shape. In another example, at least a quarter, a third, half or all reagent dots have different shapes.

The reagent dots can have any suitable space(s) or distance(s) between or among the dots. In one example, the distance between or among the reagent dots is about 1-10 um, 10-50 um, 51-100 um, 101-200 um, 201-300 um, 301-400, 401-500, or 501-600 um. The space(s) or distance(s) between or among the reagent dots can be the same or different. In one example, the space or distance between at least a quarter, a third, half or all reagent dots is substantially the same. In another example, the space or distances between at least a quarter, a third, half or all reagent dots are different. Such space or distance can be measured by any suitable means. In some specific embodiments, the space or distance between or among reagent dots is measured as the space or distance between or among the edges of the reagent dots or adjacent reagent dots, e.g., distance between or among the edges of dots which defines the low resistance flow path of reagents. In other specific embodiments, the space or distance between or among reagent dots is measured as the space or distance between or among the centers or effective centers of the reagent dots or adjacent reagent dots.

The reagent dots can be located on any suitable places or side(s) of the matrix. In one example, the test device comprises a single layer of the plurality of reagent dot. In another example, the test device comprises multiple layers, e.g., 2, 3, 4, 5, 6, 7, 8, 9, 10 or more layers, of the plurality of reagent dots. In still another example, the test device comprises at least a layer of the plurality of reagent dots on one side of the matrix. In yet another example, the test device comprises at least a layer of the plurality of reagent dots on both sides of the matrix.

The signal(s) at the reagent dots can be generated by any suitable reactions, such as chemical, biochemical, electro-chemical, and/or binding reactions involving the analyte, the reagents located at the reagent dots, reagents added to the liquid sample and/or other liquid(s), and/or other reagents dried on the test device before use and that are transported by the liquid sample or other liquids to the reagent dots.

In some embodiments, the signal(s) at the reagent dots are generated based on binding reactions involving the analyte, the reagents located at the reagent dots, reagents added to the liquid sample and/or other liquid(s), and/or other reagents dried on the test device before use and that are transported by the liquid sample or other liquids to the reagent dots. In one example, at least one of the reagent dots comprises a reagent that is capable of binding to an analyte or another binding reagent that is capable of binding to an analyte. Preferably, the reagent is capable of specifically binding to an analyte or another binding reagent that is capable of binding to an analyte. Also preferably, the reagent avoids binding to interfering moiety or moieties in the testing sample. In another example, at least a quarter, a third, half or all reagent dots comprise a reagent that is capable of binding to an analyte or another binding reagent that is capable of binding to an analyte. Preferably, the reagents are capable of specifically binding to an analyte or another binding reagent that is capable of binding to an analyte.

The reagents located at the reagent dots can be any suitable substances. For example, the reagents can be inorganic molecules, organic molecules or complexes thereof. Exemplary inorganic molecules can be ions such as sodium, potassium, magnesium, calcium, chlorine, iron, copper, zinc, manganese, cobalt, iodine, molybdenum, vanadium, nickel, chromium, fluorine, silicon, tin, boron or arsenic ions. Exemplary organic molecules can be an amino acid, a peptide, a protein, e.g., an antibody or receptor, a nucleoside, a nucleotide, an oligonucleotide, a nucleic acid, e.g., DNA or RNA, a vitamin, a monosaccharide, an oligosaccharide, a carbohydrate, a lipid and a complex thereof.

Exemplary amino acids can be a D- or a L-amino-acid. Exemplary amino acids can also be any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V).

Any suitable proteins or peptides can be used as the reagents on the test device. For example, enzymes, transport proteins such as ion channels and pumps, nutrient or storage proteins, contractile or motile proteins such as actins and myosins, structural proteins, defense protein or regulatory proteins such as antibodies, hormones and growth factors can be used. Proteineous or peptidic antigens can also be used.

Any suitable nucleic acids, including single-, double and triple-stranded nucleic acids, can be used as the reagents on the test device. Examples of such nucleic acids include DNA, such as A-, B- or Z-form DNA, and RNA such as mRNA, tRNA and rRNA.

Any suitable nucleosides can be can be used as the reagents on the test device. Examples of such nucleosides include adenosine, guanosine, cytidine, thymidine and uridine. Any nucleotides can be used as the reagents on the test device. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any suitable vitamins can be used as the reagents on the test device. For example, water-soluble vitamins such as thiamine, riboflavin, nicotinic acid, pantothenic acid, pyridoxine, biotin, folate, vitamin $B_{12}$ and ascorbic acid can be used. Similarly, fat-soluble vitamins such as vitamin A, vitamin D, vitamin E, and vitamin K can be used.

Any suitable monosaccharides, whether D- or L-monosaccharides and whether aldoses or ketoses, can be used as the reagents on the test device. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any suitable lipids can be used as the reagents on the test device. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

In one specific embodiment, the analyte to be detected comprises or is an antigen, the binding reagent on the test device comprises or is an antibody. Preferably, the antibody specifically binds to the analyte. In one example, the test device is used in a sandwich assay format, in which a binding reagent, e.g., an antibody, is used as a reagent at the reagent dots, and another binding reagent having a detectable label is also used to form a labeled binding reagent-analyte-binding reagent or antibody sandwich at the reagent dots to generate readout signals. Alternatively, a binding reagent is used as a reagent at the reagent dots, and an antibody have a detectable label is also used to form a labeled antibody-analyte-binding reagent sandwich at the reagent dots to generate readout signals. In one example, the sandwich assay uses two antibodies, one as the capture reagent and the other as the labeled reagent.

The test device can also be used in a competition assay format. In one example, a binding reagent, e.g., an antibody, is used as a capture reagent at the reagent dots. An analyte or analyte analog having a detectable label, either added in a liquid or previously dried on the test device and redissolved or resuspended by a liquid, will compete with an analyte in a sample to bind to the capture reagent at the reagent dots. In another example, an analyte or analyte analog is used as a capture reagent at the reagent dots. A binding reagent, e.g., an antibody, having a detectable label, is either added in a liquid or previously dried on the test device and redissolved or resuspended by a liquid. An analyte in a sample will compete with the analyte or analyte analog at the reagent dots for binding to the binding reagent, e.g., an antibody, having a detectable label.

The matrix can have any suitable structure. In one example, the matrix can have a porous structure. The matrix can comprise any suitable material(s). For example, porous plastics material, such as polypropylene, polyethylene (preferably of very high molecular weight), polyvinylidene fluoride, ethylene vinylacetate, acrylonitrile and polytetrafluoroethylene can be used. See e.g., U.S. Pat. No. 6,187,598. It can be advantageous to pre-treat the member with a surface-active agent during manufacture, as this can reduce any inherent hydrophobicity in the member and therefore enhance its ability to take up and deliver a moist sample rapidly and efficiently. The matrix can also be made from paper or other cellulosic materials. In some embodiments, the matrix comprises or is made of nitrocellulose or glass fiber.

In another example, the matrix can have a non-porous structure, e.g., plastic solid surface. In some embodiments, the matrix can have other structures such as channels or other guided fluid pathways. In another example, the matrix comprises a plastic, a film of a matrix having a hydrophilic surface, or a material with a controlled contact angle with the sample liquid.

The reagent dots can comprise any suitable reagents and can be arranged to form any suitable pattern. In one example, the plurality of reagent dots comprises the same binding reagent that is capable of binding to an analyte or another binding reagent that is capable of binding to the analyte. The plurality of reagent dots form a line that is substantially parallel to the liquid sample flow direction. As the liquid sample flows laterally along the test device, the analyte, if present in the liquid sample, becomes sequentially bound to the binding reagent at each of the reagent dots until the analyte is depleted by binding to the upstream reagent dot(s). The binding of the analyte to the reagent dot(s) generates a dateable signal at the reagent dot(s), and the intensity and/or the number of the dateable signal at the reagent dot(s) provides a quantitation or a semi-quantitation of the analyte in the liquid sample.

In another example, the plurality of reagent dots comprises different binding reagents that are capable of binding to different analytes or other binding reagents that are capable of binding to the analytes. The plurality of reagent dots forms a line that is substantially parallel to the liquid sample flow direction. As the liquid sample flows laterally along the test device, the analytes, if present in the liquid sample, become bound to the binding reagents at each of the reagent dots. The binding of the analytes to the reagent dots generates dateable signals at the reagent dots, and the presence and/or intensity of the dateable signals at the reagent dots indicates the presence and/or amount of the analytes in the liquid sample.

In still another example, the plurality of reagent dots comprises different groups of binding reagents, each group of the binding reagents is capable of binding to the same analyte or another binding reagent that is capable of binding to the same analyte, and the binding reagents in different groups are capable of binding to different analytes or other binding reagents that are capable of binding to different analytes. Each group of the reagent dots forms a line that is substantially parallel to the liquid sample flow direction, and the different lines formed by the different groups of the reagent dots are substantially parallel to each other. As the liquid sample flows laterally alone the test device, the analytes, if present in the liquid sample, become sequentially bound to the binding reagents at each of the reagent dots in each group of the reagent dots until the analytes are depleted by binding to the upstream reagent dots. The binding of the analytes to the reagent dots generates dateable signals at the reagent dots, and the intensity and/or the number of the dateable signals at the reagent dots provides a quantitation or a semi-quantitation of the different analytes in the liquid sample.

In yet another example, the plurality of reagent dots comprises the same binding reagent that is capable of binding to an analyte or another binding reagent that is capable of binding to the analyte. The plurality of reagent dots forms multiple lines that are substantially parallel to the liquid sample flow direction. The reagent dots in each line comprise the same amount of the binding reagent, but the reagent dots in different lines comprise the different amounts of the binding reagent. As the liquid sample flows laterally alone the test device, the analyte, if present in the liquid sample, becomes sequentially bound to the binding reagent at each of the reagent dots in each of the lines until the analyte is depleted by binding to the upstream reagent dot(s) in each of the lines. The binding of the analyte to the reagent dot(s) generates a dateable signal at the reagent dot(s), and the intensity and/or the number of the dateable signal at the reagent dot(s) provides a quantitation or a semi-quantitation of the analyte in the liquid sample. The reagent dots in different lines can comprise the same or different amounts of the binding reagent. In one embodiment, from one end to the other end of the test device, in the direction perpendicular to the direction of said liquid sample flow, the reagent dots in different lines comprise the sequentially different amounts of the binding reagent, e.g., sequentially increasing or decreasing amounts of the binding reagent.

In yet another example, the plurality of reagent dots comprises two different groups of binding reagents. One group of the reagent dots forms a line that is at a first angle relative to the liquid sample flow direction, and the other group of the reagent dots forms a line that is at a second, different angle relative to the liquid sample flow direction. After the liquid sample flows laterally along the test device, the reagent dots in one of the lines generate a signal indicating the presence and/or amount of an analyte in the liquid sample, and the reagent dots in the other line generate a control signal indicating the test is properly conducted. When the liquid sample comprises the analyte and the test is properly conducted, the two lines of the reagent dots generate a positive symbol, indicating the presence and/or amount of the analyte in the liquid sample. When the liquid sample does not comprise the analyte and the test is properly conducted, only one line of the reagent dots generates a negative symbol, indicating the absence of the analyte in the liquid sample.

The two different groups of binding reagents can form lines that are at any suitable angles relative to the liquid sample flow direction, and the reagent dots can form any suitable readout signals to indicate the presence, absence and/or amount of the analyte in the liquid sample. For example, one group of the reagent dots forms a line that is substantially parallel to the liquid sample flow direction, and the other group of the reagent dots forms a line that is substantially perpendicular to the liquid sample flow direction. When the liquid sample comprises the analyte and the test is properly conducted, the two lines of the reagent dots generate a "+" symbol, indicating the presence and/or amount of the analyte in the liquid sample, and when the liquid sample does not comprise the analyte and the test is properly conducted, only one line of the reagent dots generates a "−" symbol, indicating the absence of the analyte in the liquid sample.

In yet another example, the plurality of reagent dots comprises two different groups of binding reagents. After the liquid sample flows laterally along the test device, reagent dots in one group generate an alpha-numeric signal indicating the presence and/or amount of an analyte in the liquid sample, and the reagent dots in the other group generate a control symbol signal indicating the test is properly conducted. The alpha-numeric signal can take any suitable forms. For example, the alpha-numeric signal can be a word such as yes, Pos, Positive, Neg, Negative, No, or OK. The control symbol signal can also take any suitable forms. For example, the control symbol signal can be a "+" sign. The test device can be configured for any suitable form of test, e.g., a sandwich or competitive test.

In yet another example, the plurality of reagent dots comprises a reagent that binds to an intended binder and the binding pattern between the reagent and the binder formed on the reagent dots indicates a kinetic property of the binding between the reagent and the binder. The reagent and the intended binder can be any suitable or desired substances. For example, the reagent can be an antigen, the binder can be an antibody to the antigen, or vice versa. The binding pattern between the antigen and the antibody formed on the reagent dots can indicate a kinetic property of the binding between the antigen and the antibody. The present device can be used to indicate any suitable kinetic property of the binding between the antigen and the antibody. For example, the kinetic property can comprise the binding affinity of the binding between the antigen and the antibody. The binding affinity can be detected with any suitable signal readout. For example, the binding pattern of a leading edge on the dot(s) can indicate that the binding reagent or antibody has a high binding affinity for the antigen, a filled out but generally inconsistent dot indicating a low affinity binding reagent, and a blanking spot indicating no specific binding between the binding reagent or antibody and the antigen. See e.g., FIG. 3.

In yet another example, the test device can comprise at least one group of the reagent dots that generate an additional signal that is not related to the presence, absence and/or amount of the analyte in the liquid sample, or whether the test is properly conducted. Such additional reagent dots can be used for any suitable purposes. For example, the additional signal can be used to indicate the authenticity, quality and/or identification of the test device, or identification of the liquid sample. The additional signal can have any suitable form or pattern. For example, the additional signal can comprise an alpha-numeric signal.

In yet another example, the test device can comprise at least one group of the reagent dots that form a circle around the sample application location, and the liquid sample moves radially to pass the group of the reagent dots. In yet another example, the test device can further comprise a flow through device portion.

The matrix can have any suitable form or shape. For example, the matrix can be in the form of a strip or a circle. The matrix can also have suitable number of elements. For example, the matrix can be made of a single element or can comprise multiple elements.

The test device can further comprise a sample application element upstream from and in fluid communication with the matrix. The sample application element can be made of any suitable materials, such as nitrocellulose, glass fiber, polypropylene, polyethylene (preferably of very high molecular weight), polyvinylidene fluoride, ethylene vinylacetate, acrylonitrile or polytetrafluoro-ethylene. The matrix and the sample application element can comprise the same or different materials.

The test device can further comprise a liquid absorption element downstream from and in fluid communication with the matrix. The liquid absorption element can be made of any suitable materials, such as paper or cellulose materials.

The test device can further comprise a control location comprising means for indicating proper flow of the liquid sample and/or a valid test result. Any suitable means can be used. In one example, the means comprises a binding reagent that binds to a binding reagent with a detectable label that also binds to the analyte. In another example, the means comprises a binding reagent that binds to a binding reagent with a detectable label that does not bind to the analyte. In still another example, the means comprises a substance that will generate a detectable signal, e.g., color or electrical signal, once a liquid flow along or through the control location.

In some embodiments, at least a portion of the matrix is supported by a solid backing. In other embodiments, half, more than half or all portion of the matrix is supported by a solid backing. The solid backing can be made of any suitable material, e.g., solid plastics. If the test device comprises electrode or other electrical elements, the solid backing should generally comprise non-conductive materials.

In some embodiments, a labeled reagent can be dried on the test device and the dried labeled reagent can be redissolved or resuspended by a liquid, e.g., a sample liquid and/or additional liquid, and transported laterally through the test device to generate readout, control and/or other signals. For example, a portion of the matrix, upstream from the at least two of the reagent dots, can comprise a dried, labeled reagent, the labeled reagent capable of being moved by a liquid sample and/or a further liquid to the at least two of the reagent dots and/or a control location to generate a detectable signal. The dried, labeled reagent can be located at any suitable places on the test device. In one example, the dried, labeled reagent is located downstream from a sample application place on the test device. In another example, the dried, labeled reagent is located upstream from a sample application place on the test device. The type of the labeled reagent can be determined based on the intended assay formats. For example, if the test device is to be used in a sandwich assay, the labeled reagent should be capable of binding, and preferably capable of specifically binding, to the analyte or another substance that binds to the analyte. The same labeled reagent can also be used for certain competitive binding assays. For other types of the competitive binding assays, the labeled reagent should be an analyte or an analyte analog linked to a detectable label.

In some embodiments, the test device can further comprise, upstream from the at least two of the reagent dots, a conjugate element that comprises a dried, labeled reagent, the labeled reagent being capable of moved by a liquid sample and/or a further liquid to the at least two of the reagent dots and/or a control location to generate a detectable signal. The conjugate element can be located downstream from a sample application place on the test device. The conjugate element can also be located upstream from a sample application place on the test device. In some embodiments, the labeled reagent binds to an analyte in the liquid sample. In other embodiments, the labeled reagent competes with an analyte in the liquid sample for binding to a binding reagent for the analyte at the at least two of the reagent dots.

Any suitable label can be used. The label can be a soluble label, such as a colorimetric, radioactive, enzymatic, luminescent or fluorescent label. The label can also be a particle or particulate label, such as a particulate direct label, or a colored particle label. Exemplary particle or particulate labels include colloidal gold label, latex particle label, nanoparticle label and quantum dot label. Depending on the specific configurations, the labels such as colorimetric, radioactive, enzymatic, luminescent or fluorescent label, can be either a soluble label or a particle or particulate label.

In some embodiments, the labeled reagent is dried in the presence of a material that stabilizes the labeled reagent, facilitates solubilization or resuspension of the labeled reagent in a liquid, and/or facilitates mobility of the labeled reagent. Any suitable material can be used. For example, the material can be a protein, e.g., a meta-soluble protein, a peptide, a polysaccharide, a sugar, e.g., sucrose, a polymer, a gelatin or a detergent. See e.g., U.S. Pat. Nos. 5,120,643 and 6,187,598.

The present test devices can be used with any suitable sample liquid. In one example, a sample liquid alone is used to transport the analyte and/or the labeled reagent to the at least two of the reagent dots. In another example, a developing liquid is used to transport the analyte and/or the labeled reagent to the at least two of the reagent dots. In still another example, both sample liquid and a developing liquid is used to transport the analyte and/or the labeled reagent to the at least two of the reagent dots.

In some embodiments, the test device can further comprise a housing that covers at least a portion of the test device, wherein the housing comprises a sample application port to allow sample application upstream from or to the at least two of the reagent dots and an optic opening around the at least two of the reagent dots to allow signal detection at the two of the reagent dots. The optic opening can be achieved in any suitable way. For example, the optic opening can simply be an open space. Alternatively, the optic opening can be a transparent cover.

In other embodiments, the housing can cover the entire test device. In still other embodiments, at least a portion of the sample receiving portion of the matrix or the sample application element is not covered by the housing and a sample is applied to the portion of the sample receiving portion of the matrix or the sample application element outside the housing and then transported to the at least two of the reagent dots. The housing can comprise any suitable material. For example, the housing can comprise a plastic material, a biodegradable material or a cellulosic material. In another example, the housing, whether in part or in its entirety, can comprise an opaque, translucent and/or transparent material.

In some embodiments, the present invention provides for a test device wherein the liquid sample has moved laterally along the test device to generate detectable signal(s) at the at least two of the reagent dots.

C. Methods for Detecting an Analyte Using a Lateral Flow Device with Two Dimensional Features In another aspect, the present disclosure provides for a method for detecting an analyte using the above test device. In one exemplary embodiment, the present disclosure provides for a method for detecting an analyte in a liquid sample, which method comprises a) contacting a liquid sample with the above test device, wherein the liquid sample is applied to a site of the test device upstream of the at least two of the reagent dots; b) transporting an analyte, if present in the liquid sample, to the at least two of the reagent dots; and c) assessing the presence, absence, amount and/or pattern of signal(s) generated at the at least two of the reagent dots to determining the presence, absence and/or amount of the analyte in the liquid sample. The signal(s) at the reagent dots can be generated by any suitable reactions, such as chemical, biochemical, electrochemical, and/or binding reactions involving the analyte, the reagents located at the reagent dots, reagents added to the liquid sample and/or other reagents dried on the test device before use and are transported by the liquid sample or other liquids to the reagent dots.

In another exemplary embodiment, the signal(s) at the reagent dots can be generated by binding reactions involving the analyte and the reagents located at the reagent dots, and a labeled reagent added to the liquid sample or dried on the test device before use and is transported by the liquid sample or other liquids to the reagent dots. For example, the method comprises a) contacting a liquid sample with the above test device, wherein the liquid sample is applied to a site of the test device upstream of the at least two of the reagent dots; b) transporting an analyte, if present in the liquid sample, and a labeled reagent to the at least two of the reagent dots; and c) assessing the presence, absence, amount and/or pattern of signal(s) at the at least two of the reagent dots, e.g., signal(s) generated by the labeled reagent at the at least two of the reagent dots, to determining the presence, absence and/or amount of the analyte in the liquid sample.

In some embodiments, the liquid sample and the labeled reagent are premixed to form a mixture and the mixture is applied to the test device. For example, the labeled reagent can be provided or stored in a liquid and then can be premixed with a sample liquid to form a mixture and the mixture is applied to the test device. In another example, the labeled reagent can be dried in a location or container not in fluid communication with the test device, e.g., in a test tube or well such as a microtiter plate well. In use, the sample liquid can be added to the container, e.g., the test tube or well, to form the mixture and the mixture can then be applied to the test device.

In other embodiments, the test device comprises a dried labeled reagent before use and the dried labeled reagent is solubilized or resuspended, and transported to the at least two of the reagent dots by the liquid sample and/or other liquid. The dried labeled reagent can be located at any suitable location on the test device. For example, the dried labeled reagent can be located downstream from the sample application site, and the dried labeled reagent can be solubilized or resuspended, and transported to the at least two of the reagent dots by the liquid sample and/or other liquid. In another example, the dried labeled reagent can be located upstream from the sample application site, and the dried labeled reagent can be solubilized or resuspended, and transported to the at least two of the reagent dots by another liquid.

In some embodiments, the labeled reagent is solubilized or resuspended, and transported to the at least two of the reagent dots by the liquid sample alone. In other embodiments, the analyte and/or labeled reagent is solubilized or resuspended, and transported to the at least two of the reagent dots by another liquid. In still other embodiments, the analyte and/or labeled reagent is solubilized or resuspended, and transported to the at least two of the reagent dots by both the sample liquid and another liquid, e.g., a developing liquid.

The present test devices can be used to detect an analyte in any suitable sample liquid. In some embodiments, the liquid sample can be body fluid sample, such as a whole blood, a serum, a plasma, a urine sample or an oral fluid. Such body fluid sample can be sued directly or can be processed, e.g., enriched, purified, or diluted, before use. In other embodiments, the liquid sample can be a liquid extract, suspension or solution derived from a solid or semi-solid biological material such as a phage, a virus, a bacterial cell, an eukaryotic cell, a fugal cell, a mammalian cell, a cultured cell, a cellular or subcellular structure, cell aggregates, tissue or organs. In specific embodiments, the sample liquid is obtained or derived from a mammalian or human source. In still other embodiments, the liquid sample is a sample derived from a biological, a forensics, a food, a biowarfare, or an environmental source. In other embodiments, the sample liquid is a clinical sample, e.g., a human or animal clinical sample. In still other embodiments, the sample liquid is a man-made sample, e.g., a standard sample for quality control or calibration purposes.

The present test devices can be used to detect the presence, absence and/or amount of an analyte in any suitable sample liquid. In some embodiments, the present test devices are used to detect the presence or absence of an analyte in any suitable sample liquid, i.e., to provide a yes or no answer. In other embodiments, the present test devices are used to quantify or semi-quantify the amount of an analyte in a liquid sample.

The present test devices can be used to detect the presence, absence and/or amount of a single analyte in any suitable sample liquid. Alternatively, the present test devices can be used to detect the presence, absence and/or amount of multiple analytes in a liquid sample. In still other embodiments, the present test devices can be used to quantify or semi-quantify the amounts of the multiple analytes in the liquid sample.

The present test devices can be used to detect the presence, absence and/or amount of any suitable analyte in a sample liquid. Exemplary analytes include inorganic molecules, organic molecules or complexes thereof. Exemplary inorganic molecules can be ions such as sodium, potassium, magnesium, calcium, chlorine, iron, copper, zinc, manganese, cobalt, iodine, molybdenum, vanadium, nickel, chromium, fluorine, silicon, tin, boron or arsenic ions. Exemplary organic molecules can be an amino acid, a peptide, a protein, a nucleoside, a nucleotide, an oligonucleotide, a nucleic acid, e.g., a DNA or RNA molecule or a hybrid thereof, a vitamin, a monosaccharide, an oligosaccharide, a carbohydrate, a lipid and a complex thereof. In some embodiments, the analyte is a cell, a virus or a molecule. In other embodiments, the analyte is hCG, hLH, hFSH, hTSH, a disease or disorder marker, e.g., a cardiac biomarker, an antigen of an infectious organism, an antibody to an infectious organism, etc.

The present methods can be used for any suitable purpose. For example, present methods can be used for clinical diagnosis, prognosis, risk assessment and prediction, stratification and treatment monitoring and adjustment. In another example, present methods can be used for various research purposes, such as basic research, drug candidate screening, animal studies, and clinical trials. In still another example, present methods can be used in tests for standard setting, quality control, illegal drug screening, food safety, environmental safety, industrial safety, pollution, detection of biowarfare agents, screening for drugs or pharmaceuticals, and monitoring the quality of manufacturing using bioreactors looking for unwanted molecules, etc. The present tests devices and methods can be used in any suitable settings, such as tests in the labs, clinics, hospitals, physician's offices, homes, natural environments, battle fields and first responder environments, e.g., environments for fire, paramedic, police actions.

D. Process for Manufacturing a Lateral Flow Device with Two Dimensional Features In still another aspect, the present disclosure provides for a process for manufacturing a test device for detecting an analyte in a liquid sample, which process comprises forming a plurality of reagent dots on a matrix to make a test device comprising at least two of said reagent dots that do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, wherein each of said two reagent dots is neither a reagent line across the entire width of said matrix in a direction perpendicular to the direction of said liquid sample flow nor a complete circle of a reagent line, and after a liquid sample flows laterally along said test device and passes said at least two reagent dots, said at least two reagent dots form a predetermined pattern to indicate presence, absence and/or amount of said analyte in said liquid sample.

The plurality of reagent dots can form any suitable predetermined pattern. In some embodiments, the plurality of reagent dots form a line, multiple lines, a symbol, a geometric shape or an alpha-numeric shape. Any suitable alpha-numeric shape can be formed. Exemplary alpha-numeric shapes include a letter, a word, a number or a combination thereof. The reagent dot line can be formed at any suitable direction. In one example, the line is substantially parallel to the liquid sample flow direction. In another example, the line is substantially perpendicular to the liquid sample flow direction. In still another example, the reagent dots form multiple lines that comprise at least one line that is substantially parallel to the liquid sample flow direction and at least one line that is substantially perpendicular to the liquid sample flow direction.

The reagent dots can be formed on the matrix by any suitable methods. In some embodiments, the plurality of reagent dots is formed by dispensing a reagent at predetermined locations on the matrix. Any suitable dispensing techniques or methods can be used. For example, the reagent can be dispensed by a drop on demand method or a printing process using a mechanical transfer of the reagent. Any suitable drop on demand methods can be used. For example, the drop on demand method can be conducted using an inkjet or solenoid valve based dispenser, a piezoelectric dispenser, screen printing, airjet or airbrush technology, hollow pin printing, or near-contact dispensing.

The reagent dots in the test device can have any suitable size(s). In one example, at least one of the reagent dots has a diameter of about 0.1-1 um, 1-10 um, 10-50 um, 51-100 um, 101-200 um, 201-300 um, 301-400 um, 401-500 um and 501-1000 um. In another example, at least a quarter, a third, half or all reagent dots have a diameter of about 0.1-1 um, 1-10 um, 10-50 um, 51-100 um, 101-200 um, 201-300 um, 301-400 um, 401-500 um or 501-1000 um. In still another example, at least one of the reagent dots has a diameter or surface area that is about 10%, 5%, 1%, 0.5%, 0.1%, 0.05%, 0.01%, 0.001% or smaller diameter or surface area of the length, width or surface area of the matrix calculated by the width and length of the membrane. In yet another example, at least a quarter, a third, half or all reagent dots have a diameter or surface area that is about 10%, 5%, 1%, 0.5%, 0.1%, 0.05%, 0.01%, 0.001% or smaller diameter or surface area of the length, width or surface of the matrix.

The reagent dots in the test device can have the same or different size(s) or diameter(s). In one example, at least a quarter, a third, half or all reagent dots have substantially the same size or diameter. In another example, at least a quarter, a third, half or all reagent dots have substantially different sizes or diameters.

The reagent dots in the test device can have any suitable shapes, e.g., any suitable regular or irregular shape. In one example, at least one of the reagent dots has a shape that is a line, a circle, a rod, a square, a triangle, a rectangle or an irregular shape. In another example, at least a quarter, a third, half or all reagent dots have a shape that is a line, a circle, a rod, a square, a triangle, a rectangle or an irregular shape. The reagent dots in the test device can have the same or different shape(s). In one example, at least a quarter, a third, half or all reagent dots have the same shape. In another example, at least a quarter, a third, half or all reagent dots have different shapes.

The reagent dots can have any suitable space(s) or distance(s) between or among the dots. In one example, the distance between or among the reagent dots is about 1-10 um, 10-50 um, 51-100 um, 101-200 um, 201-300 um, 301-400, 401-500, or 501-600 um. The space(s) or distance(s) between or among the reagent dots can be the same or different. In one example, the space or distance between or among at least a quarter, a third, half or all reagent dots is substantially the same. In another example, the space or distances between or among at least a quarter, a third, half or all reagent dots are different.

The reagent dots can be formed on any suitable places or side(s) of the matrix. In one example, the present process comprises forming a single layer or multiple layers of the plurality of reagent dots. In another example, the present process comprises forming at least a layer of the plurality of reagent dots on both sides of the matrix. In still another example, the present process comprises forming multiple layers of the plurality of reagent dots on both sides of the matrix. In yet another example, the present process further comprises a drying step between forming the multiple layers of the plurality of reagent dots.

In some embodiments, the present invention provides for a test device for detecting an analyte in a liquid sample, which is manufactured by the above process(es).

E. Exemplary Embodiments

In some embodiments, the present invention provides for a method for the dispensing of capture reagent geometries in lateral flow formats that allows for the generation of signals in non-standard formats, including dots (or "pixels") which do not perturb the flow of reagents in the test matrix with the result that multiple small signal features can be developed and may be combined to form symbols and letters. In other embodiments, the present invention provides for a new device, a lateral flow test with configurable indicia compatible with multiplexing and quantitative testing. Embodiments of novel and improved assay formats that can be generated as a result of the application of this method, unique device constructs that enable multiplex testing to be performed in a single device, and unique device constructs that enable improved quantitative and qualitative interpretation of test results are also provided.

One aspect of the invention is directed to a method for the dispensing of chemical or biological reagents ("reagents") onto porous and/or solid matrices such as plastic films in predetermined "pixilated" patterns that have low resistance to the flow of fluids and particulates through the printed reagents. These patterns have dimensional features that are spatially separated at distances on the order of the diffusion distance of the sample/conjugate flow normal to the principal direction of flow in the system. The dimensions of these features and positioning relative to one another ensures that each feature can interact with the reagents in the test system individually without occluding the reaction matrix or otherwise causing disruption in flow. These feature dimensions and relative positions will vary with material and reagent characteristics such as the surface type (solid/porous), pore size if porous, and capture reagent affinity.

The method can be used to generate complex or simple reagent patterns on a lateral flow membrane or other matrix that develop not only perpendicular to the direction of flow as in a traditional lateral flow system, but parallel to the direction of flow. This method can also be used to generate such features on a variety of matrices that can conduct fluids, including nitrocellulose membranes, glass fibers and plastics and films. This method can further be used to generate a variety of symbols, including lines, dots and geometric and alpha-numeric shapes.

In certain implementations of the invention, the method may be used for producing quantitative tests. The pixel format provides for the ability to detect concentration depletion of an analyte as it flows through a field of pixels. This is shown schematically in FIGS. 6(a) and 6(b). The same principle applies to both particulate and non-particulate (molecular) labels. The exemplary test format is as follows: 1. dispense a pixel field across the lateral test strip membrane where the pixel field consists of a series of reagent dots across the width of the membrane in patterns such as those shown. The dots may be offset or physically separated at such a distance that lateral diffusion can occur between spots. When sample flows through this field, analyte will bind to the dots and become depleted as it migrates further up the membrane. When conjugate is subsequently flowed through the system, a depletion of analyte concentration is illustrated by decreasing signal intensity from bottom to top of the matrix. This can form the basis of a test format for achieving titration or quantification of the analyte through a direct measurement of the concentration gradient either by eye or using a reader.

A further refinement on this technique can be envisaged by titrating the capture reagent in one dimension, leading to the formation of a 2-dimensional binding array when sample is run up the strip. (Shown schematically in FIG. 7). In this system, side by side lines of binding pixels are dispensed in the direction of flow, each line containing binding reagent at a different concentration. The two dimensional binding pattern thus created yields a system that can produce a quantitative measure of analyte in the system that has a broad dynamic range A further refinement involves the use of this format for multiplexed detection or quantification. An example of how the pixel format can be used for multiplexed formats is shown in FIG. 8, which shows the pixel pattern for 4 analytes using a format of 4×20 pixels with a pixel size of about 250 um with 100 um separation between pixels. The 20 pixel dimension is laid out in the sample flow direction.

This method can be used to produce alpha-numeric or graphical results since signal generation is not dependent on orienting the capture reagent perpendicular to the direction of flow. Multiple potential embodiments can be envisaged, with the generation of results in the form of words or symbols for easy interpretation, or the creation of coded numerical results or identifiers on the product.

In the present embodiment the production of the assay matrix is dispensing of individual drops. The method for dispensing of the arrays can be based on a variety of technologies, including inkjet, BioJet, hollow pin or piezoelectric. Other dispensing methods may be envisaged.

In one preferred embodiment the dispensing technique is printing. In this embodiment the method involves printing of the reagent pixels in the flow path to create individual features that are of a dimension (in all three axes) that allows each individual feature to capture analyte and signal reagent and develop completely, irrespective of the binding affinity of the reagent, as long as the reagent has some affinity for the analyte.

The three dimensional matrix arrangement of the individual features generates larger patterns which, when viewed in or on a plane produce indicia representative of the test results such as symbols (alpha-numeric, lines or dots) that can be used for test interpretation. Result interpretation can be qualitative or quantitative and may be performed by eye or by a reader. For qualitative tests, the presence or absence of such indicia will be representative of the test result. In the instances where test results are quantitative in nature the quantity, size, or intensity of indicia may be the representative measure.

In another preferred embodiment the dispensing technique is multi-layer printing. In this embodiment the method involves printing of the reagents in multiple layers in the flow path to create individual features that are of a dimension (in all three axes) that allows each individual feature to capture analyte and signal reagent and develop completely, irrespective of the binding affinity of the reagent, as long as the reagent has some affinity for the analyte. The multiple layers of printing can occur on the same side of the matrix or on opposite sides of the matrix to create features at different depths within the matrix.

The three dimensional matrix arrangement of the individual features generates larger features which, when viewed in or on a plane produce indicia representative of the test results such as symbols (alpha-numeric, lines or dots) that can be used for test interpretation. Result interpretation can be qualitative or quantitative and may be performed by eye or by a reader. For qualitative tests, the presence or absence of such indicia will be representative of the test result. In the instances where test results are quantitative in nature the quantity, size, or intensity of indicia may be the representative measure.

Examples of Potential Embodiments

In all of the described embodiments, the signal reagents used to generate the signal in the test would include visible, paramagnetic, optically excited particles or molecules. Optically excited would include fluorescence, luminescence, up converting phosphors) and also add enzymes for visual, fluorescent and electrochemical signaling. Other types of signal generation could be envisaged.

1. Alpha Numeric Symbol on a Lateral Flow Strip 1.1. Exemplary Application: Pregnancy test with a + and − indicating positive or negative. The particular application is non-limiting and is for illustration only. This example illustrates the method for generating a true + and − on a lateral flow strip.

In most pregnancy tests, two antibodies are used to bind to the hCG molecule to create a positive signal. Anti hCG alpha can be striped on the test line, and anti hCG beta is conjugated to the label used to generate the signal. These are often monoclonal antibodies. The control line on the system can therefore be an anti-mouse antibody, which will bind directly to the conjugated anti hCG beta antibody whether hCG is present or not. In a typical system, the test line and control line are two independent lines, striped perpendicular to the direction of flow. In this embodiment, one line is striped perpendicular to flow, and the other is striped in the direction of flow, crossing each other in the center of the strip. When no analyte is present, only one line will develop, creating a "−". When the analyte is present, a "+" will appear, when both lines develop. This is possible in our embodiment, while not possible in standard lateral flow systems due to the fact that it is possible to develop distinct lines in the direction of flow in our system. This format will also function when the lines are at an angle to flow, creating an "x" rather than a "+".

1.2. This embodiment will also function in the situation where the assay is a competitive assay, such as a drugs of abuse test. In this instance, the presence of the analyte prevents the second line from forming. However the positive in this system would create a "−" symbol, so an alternative symbol may be used (see Embodiment 2 below).

As well as a "+" or "−", this method can be used to create words as reporting mechanisms in lateral flow. The word "Yes" can be printed on the strips and develop in the presence of the analyte. In a biowarfare application such as an anthrax test, where interpretation of results is critical, the word "Danger" could, for example appear, removing doubt from the warfighter or technician that a likely exposure event is in progress.

2. Alpha Numeric Positive Reporting System in a Competitive Lateral Flow Assay

In competitive assay systems, the presence of the analyte results in the disappearance of the test line. This format of reporting can lead to confusion in the hands of some users, who are more used to the appearance of a line in the presence of a positive. Competitive assays are important formats for the detection of small molecules, for example drugs of abuse, or many biomolecules of importance. The system of generating symbols on a lateral flow strip can allow for the improvement of interpretation. For example, the control line could be configured as a "+" symbol, designed to develop in all cases. The test line could be printed as an alphanumeric series, for example the word "Not". Thus in the case where no analyte is present, the result "Not +" appears. When the analyte is present, the word "Not" will not develop and only the "+" symbol will develop. Other forms of this feature can be readily envisaged.

3. Quantification 3.1. One embodiment of this test format is to create a series of individual dots of capture reagent, or "Pixels" throughout the read area of the test strip. As the sample moves through the read area, analyte will be bound at all of those capture dots. The analyte will thus be depleted as the sample migrates through the system, potentially resulting in the creation of a gradient of spot intensity along the length of the strip. This could be used to create a "Thermometer" style result, wherein the height and intensity of the developed area in the system can be related to the concentration of analyte in the system. This could be used for titration of analytes (e.g., cardiac biomarkers such as TnI or pro BNP, FABP or CKMB, or antibody concentrations) in quantitative or semi quantitative systems.

3.2. In a second embodiment, individual channels of printed reagents are generated on the membrane. The "channels" are discrete areas oriented in the direction of flow, each consisting of a set of capture pixels as described in the above example. There may be two or more discrete channels side by side in the direction of flow. No physical separation is required. The capture reagents may be different reagents, in the example of a multiplexed test, such that each channel detects a different analyte in a single sample. The capture reagent may also be the same reagent, however at different concentrations. Thus, the titration effect described in 3.1 above can be performed in two dimensions, with a titration of the capture reagent in the axis perpendicular to flow, and a titration of the analyte occurring in the direction of flow as it is depleted from the sample as the sample moves through the capture and read area. This will allow for titrations and quantification of analyte over a very broad dynamic range. This may be useful in quantifying levels of an analyte in a sample that can be present over a broad range in normal and test subjects or samples (e.g. hCG where applications exist for detecting levels as low as 10 mIU/ml and as high as 250,000 mIU/ml, a dynamic range that cannot be handled by most lateral flow systems).

This format may also be useful in assessing binding kinetics and screening for antibodies or other reagents for use in lateral flow or other assay formats. For example, when screening for antibodies for lateral flow formats, it is useful to screen for antibodies with high affinity. Those antibodies will produce distinctive binding features in a pixilated assay (e.g., high affinity binding will typically develop as a strong leading edge of a dot rather than an evenly developed dot). The higher the affinity, the more of the antibody will be quickly pulled out of the sample as it migrates up the strip. A high affinity binding system could therefore be indicated by evaluating the pattern of development of individual dots, as well as observing how high up the strip the development pattern goes.

4. Test Identification

Printing of alpha numeric information on strips that will only appear when the strip is developed. This code could develop using the control line binding system, and may in fact be the control line or may be visible elsewhere on the device. This can be used for anti-counterfeiting, for QC or product identification purposes, or in applications that require verification of the strip identity (e.g., telephone or internet based diagnostics linked to prescription).

5. Non-Linear Embodiments

The pixilation concept allows for the creation of alternate assay formats, such as radial systems, where sample is added to a central well and migrates in all directions around the well. This could be used for multiplexing or for quantification as described in 3 above. The pixilation concept may also be used to create results in complex flow patterns such as in printed liquidic circuits or other microfluidic formats.

6. Flow Through or Hybrid Flow Through/Lateral Flow Systems

This pixilation concept may be applied in flow through assay formats, where there is some form of vertical movement of fluids as well as horizontal movement. Flow through assays, where reagents move vertically through an assay as against horizontally, are typically used where multiple steps are not an issue (for example in the clinical laboratory where trained staff are operating the tests and a CLIA waiver is not required). They are also used in low cost, low complexity environments, such as for HIV testing in the developing world. One of the issues typically encountered with the flow through format is interpretation of results, which involves the interpretation of individual dots by eye or occasionally by reader. This system could be used to generate patterns of dots that are easier to interpret.

7. Nonstandard Materials and Configurations

The pixilation concept or format lends itself to application in alternative assay configurations. In essence, this method of preparation of reagent patterns on membranes allows for the creation of arrays in low cost membranes such as nitrocellulose, which can then be probed using a flow of reagents laterally through the membrane. This can be applied to papers or other matrices. This methodology can also be coupled with tethering methods such as Quantiscientifics' protein tethering system to create easy to use two dimensional arrays that can be probed using a lateral flow technique, allowing for ease of use, removal of the need for complex and expensive processing units and expensive plates or slides. This may also be applicable to nucleic acid arrays.

8. Three Dimensional Pixel Arrays

In this embodiment, an array of reagents is printed on each side of a porous, hydrophilic matrix such as nitrocellulose or a solid hydrophilized matrix such as a plastic that has been plasma treated or hydrophilized in another way. Those capture reagents may be directed against the same or different analytes. When the test is run the assay develops on both sides of the matrix and can be individually analyzed.

9. Signal Readout

Any or all of these embodiments are intended to be interpreted either by eye or by a reader system.

In one aspect, the present invention provides for a diagnostic test device having an array of one or more reagents dispensed in a pixelated array on a single strip interspaced in a manner that does not impede fluidic flow across the substrate thereby allowing continuous reactions between the sample and various reagents to occur uniformly across and along the test strip. The individual pixels of reagents can react with the specific elements of the test sample to collectively or individually form signals which can be interpreted quantitatively or qualitatively. The signal can be a predetermined indicia shape.

In some embodiments, two or more differing reagent sets can be dispensed sequentially onto a single strip in order to produce detectable signals indicative of two or more agents. The two or more differing reagent sets can be dispensed concurrently in a single array onto a single strip in order to produce detectable signals indicative of two or more agents in the test sample. The two or more reagents can also be dispensed in a 3 dimensional array, having at least two layers of reagent being superimposed. In other embodiments, the reagent sets can be dispensed in a pattern allowing for the development of signals in the direction of flow of the strip, allowing for development of qualitative or quantitative, single or multiplexed results.

In another aspect, the present invention provides for a method for manufacturing a diagnostic test device having low flow resistance to liquidized test sample media (material) in the analytical matrix including the steps of: dispensing at least one reagent material in a prescribed 2 dimensional pixelated array pattern onto a hydrophilic or hydrophilized substrate material, each of the pixels having vacuous fluid flow volumes there between such that each pixel will develop without creating significant resistance in the flow path of the device.

In some embodiments, reagent can be dispensed in a manner that reactions between the sample material and specific reagent pixels produces at least one detectable signal on the substrate material such as an identifiable symbol or prescribed pattern indicative of the test result. Indicia can be alpha-numeric, geometric or other predetermined shapes. Exemplary reagents include antibodies, antigens, nucleic acid, e.g., DNA or RNA, based molecules, proteins, peptides or any other large or small molecules.

The pixel can have any suitable size. In some embodiments, the pixel can have a size or diameter at about 0.1-1 um, 1-10 um, 10-50 um, 51-100 um, 101-200 um, 201-300 um, 301-400 um, 401-500 um, or 501-1000 um. The pixels can have any suitable spacing between or among the pixels, especially the adjacent pixels. In some embodiments, the pixels or adjacent pixels can have a minimum spacing or distance of about 1-10 um, 10-50 um, 51-100 um, 101-200 um, 201-300 um, 301-400, 401-500, or 501-600 um.

Any suitable method or technique can be used to dispense the pixels. In some embodiments, the pixel dispensing method can be drop on demand using inkjet or solenoid valve based dispensers, piezoelectric dispensers, screen printing, airjet or airbrush technology, hollow pin printing, near-contact dispensing and any other commercial printing process using a mechanical transfer of reagents.

In still another aspect, the present invention provides for a method of manufacturing a 3 dimensional reaction matrix in a diagnostic test by: dispensing reagent in a prescribed pixelated pattern, drying the dispensed reagent, dispensing at least one additional layer of reagent pixels on top of the first dispensed reagent pattern layer or on the opposite side of the porous matrix, creating a three dimensional pixel structure within the matrix, drying each layer after dispensing.

In yet another aspect, the present invention provides for a method of manufacturing a diagnostic test that includes a reaction matrix that has been processed using a method that includes the steps of: dispensing or transferring of reagent in a prescribed pixelated pattern, drying the dispensed reagent, dispensing or transfer of at least one additional layer of reagent pixels on top of the first dispensed reagent pattern layer or on the opposite side of a non-porous matrix, drying each layer after dispensing, thereby creating a matrix with a pixilated flowpath on either side of the matrix allowing for two tests to be run simultaneously on the same matrix.

The present invention is further illustrated by the following exemplary embodiments:

1. A test device for detecting an analyte in a liquid sample, which device comprises a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, each of said two reagent dots is neither a reagent line across the entire width of said matrix in a direction perpendicular to the direction of said liquid sample flow nor a complete circle of a reagent line, and after a liquid sample flows laterally along said test device and passes said at least two reagent dots, said at least two reagent dots form a predetermined pattern to indicate presence, absence and/or amount of said analyte in said liquid sample.

2. The test device of embodiment 1, wherein the plurality of reagent dots comprises two reagent dots.

3. The test device of embodiment 1, wherein the plurality of reagent dots comprises more than two reagent dots.

4. The test device of embodiment 3, wherein the plurality of reagent dots comprises at least 10, 50, 100, 500, 1,000, 5,000, 10,000 or more reagent dots.

5. The test device of any of the embodiments 3-4, wherein at least a quarter, a third, half or all reagent dots do not overlap and are sufficiently spaced apart from each other so that when the liquid sample flows laterally along the matrix, flow of the liquid sample to, through and/or around one of the reagent dots does not substantially affect flow of the liquid sample to, through and/or around the other reagent dots.

6. The test device of embodiment 1, wherein the predetermined pattern is selected from the group consisting of a line, multiple lines, a symbol, a geometric shape and an alpha-numeric shape.

7. The test device of embodiment 6, wherein the alpha-numeric shape is a letter, a word, a number or a combination thereof.

8. The test device of embodiment 6, wherein the line is substantially parallel to the liquid sample flow direction.

9. The test device of embodiment 6, wherein the line is substantially perpendicular to the liquid sample flow direction.

10. The test device of embodiment 6, wherein the multiple lines comprises at least a line that is substantially parallel to the liquid sample flow direction and at least a line that is substantially perpendicular to the liquid sample flow direction.

11. The test device of any of the embodiments 1-10, wherein the plurality of reagent dots comprises different reagents and the test device is used to detect multiple analyte in the liquid sample.

12. The test device of any of the embodiments 1-10, wherein the plurality of reagent dots comprises the same reagent and the test device is used to detect the amount of the analyte in the liquid sample.

13. The test device of the embodiment 12, wherein the plurality of reagent dots comprises the same amount of the reagent.

14. The test device of the embodiment 12, wherein the plurality of reagent dots comprises the different amounts of the reagent.

15. The test device of any of the embodiments 1-14, wherein at least one of the reagent dots has a diameter of about 0.1-1 um, 1-10 um, 10-50 um, 51-100 um, 101-200 um, 201-300 um, 301-400 um, 401-500 um and 501-1000 um, or at least one of the reagent dots has a diameter or surface area that is about 10%, 5%, 1%, 0.5%, 0.1%, 0.05%, 0.01%, 0.001% or smaller diameter or surface area of the length, width or surface area of the matrix.

16. The test device of the embodiment 15, wherein at least a quarter, a third, half or all reagent dots have a diameter of about 0.1-1 um, 1-10 um, 10-50 um, 51-100 um, 101-200 um, 201-300 um, 301-400 um, 401-500 um or 501-1000 um, or at least a quarter, a third, half or all reagent dots have a diameter or surface area that is about 10%, 5%, 1%, 0.5%, 0.1%, 0.05%, 0.01%, 0.001% or smaller diameter or surface area of the length, width or surface of the matrix.

17. The test device of the embodiment 15, wherein at least a quarter, a third, half or all reagent dots have substantially the same size or diameter.

18. The test device of any of the embodiments 1-17, wherein at least one of the reagent dots has a shape selected from the group consisting of a line, a circle, a rod, a square, a triangle, a rectangle and an irregular shape.

19. The test device of the embodiment 18, wherein at least a quarter, a third, half or all reagent dots have a shape selected from the group consisting of a line, a circle, a rod, a square, a triangle, a rectangle and an irregular shape.

20. The test device of the embodiment 18, wherein at least a quarter, a third, half or all reagent dots have the same shape.

21. The test device of any of the embodiments 1-20, wherein the distance between edges of at least two of the reagent dots is about 1-10 um, 10-50 um, 51-100 um, 101-200 um, 201-300 um, 301-400, 401-500, or 501-600 um.

22. The test device of the embodiment 21, wherein the distance between at least a quarter, a third, half or all reagent dots is substantially the same.

23. The test device of any of the embodiments 1-22, wherein at least one of the reagent dots comprises a reagent that is capable of binding to an analyte or another binding reagent that is capable of binding to an analyte.

24. The test device of embodiment 23, wherein the reagent is capable of specifically binding to an analyte or another binding reagent that is capable of binding to an analyte.

25. The test device of the embodiment 23, wherein at least a quarter, a third, half or all reagent dots comprise a reagent that is capable of binding to an analyte or another binding reagent that is capable of binding to an analyte.

26. The test device of embodiment 25, wherein the reagents are capable of specifically binding to an analyte or another binding reagent that is capable of binding to an analyte.

27. The test device of any of the embodiments 1-26, which comprises multiple layers of the plurality of reagent dots.

28. The test device of any of the embodiments 1-27, which comprises at least a layer of the plurality of reagent dots on both sides of the matrix.

29. The test device of any of the embodiments 1-27, wherein the reagents are inorganic molecules, organic molecules or complexes thereof.

30. The test device of embodiment 25, wherein the organic molecules are selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

31. The test device of embodiment 30, wherein the protein is an antigen or an antibody.

32. The test device of any of the embodiments 1-31, wherein the matrix has a porous structure.

33. The test device of embodiment 32, wherein the matrix comprises nitrocellulose, glass fiber, polypropylene, polyethylene (preferably of very high molecular weight), polyvinylidene fluoride, ethylene vinylacetate, acrylonitrile and/or polytetrafluoro-ethylene.

34. The test device of any of the embodiments 1-31, wherein the matrix has a non-porous structure.

35. The test device of embodiment 32, wherein the matrix comprises a plastics, a film of a matrix having a hydrophilic surface, or a material with a controlled contact angle with the sample liquid.

36. The test device of embodiment 1, wherein the plurality of reagent dots comprises the same binding reagent that is capable of binding to an analyte or another binding reagent that is capable of binding to the analyte, the plurality of reagent dots form a line that is substantially parallel to the liquid sample flow direction, as the liquid sample flows laterally along the test device, the analyte, if present in the liquid sample, becomes sequentially bound to the binding reagent at each of the reagent dots until the analyte is depleted by binding to the upstream reagent dot(s), the binding of the analyte to the reagent dot(s) generates a dateable signal at the reagent dot(s), and the intensity and/or the number of the dateable signal at the reagent dot(s) provides a quantitation or a semi-quantitation of the analyte in the liquid sample.

37. The test device of embodiment 1, wherein the plurality of reagent dots comprises different binding reagents that are capable of binding to different analytes or other binding reagents that are capable of binding to the analytes, the plurality of reagent dots form a line that is substantially parallel to the liquid sample flow direction, as the liquid sample flows laterally along the test device, the analytes, if present in the liquid sample, become bound to the binding reagents at each of the reagent dots, the binding of the analytes to the reagent dots generates dateable signals at the reagent dots, and the presence and/or intensity of the dateable signals at the reagent dots indicates the presence and/or amount of the analytes in the liquid sample.

38. The test device of embodiment 1, wherein the plurality of reagent dots comprises different groups of binding reagents, each group of the binding reagents is capable of binding to the same analyte or another binding reagent that is capable of binding to the same analyte, and the binding reagents in different groups are capable of binding to different analytes or other binding reagents that are capable of binding to different analytes, each group of the reagent dots forms a line that is substantially parallel to the liquid sample flow direction, and the different lines formed by the different groups of the reagent dots are substantially parallel to each other, as the liquid sample flows laterally alone the test device, the analytes, if present in the liquid sample, become sequentially bound to the binding reagents at each of the reagent dots in each group of the reagent dots until the analytes are depleted by binding to the upstream reagent dots, the binding of the analytes to the reagent dots generates dateable signals at the reagent dots, and the intensity and/or the number of the dateable signals at the reagent dots provides a quantitation or a semi-quantitation of the different analytes in the liquid sample.

39. The test device of embodiment 1, wherein the plurality of reagent dots comprises the same binding reagent that is capable of binding to an analyte or another binding reagent that is capable of binding to the analyte, the plurality of reagent dots form multiple lines that are substantially parallel to the liquid sample flow direction, the reagent dots in each line comprise the same amount of the binding reagent, but the reagent dots in different lines comprise the different amounts of the binding reagent, as the liquid sample flows laterally alone the test device, the analyte, if present in the liquid sample, becomes sequentially bound to the binding reagent at each of the reagent dots in each of the lines until the analyte is depleted by binding to the upstream reagent dot(s) in each of the lines, the binding of the analyte to the reagent dot(s) generates a dateable signal at the reagent dot(s), and the intensity and/or the number of the dateable signal at the reagent dot(s) provides a quantitation or a semi-quantitation of the analyte in the liquid sample.

40. The test device of embodiment 39, wherein from one end to the other end of the test device, in the direction perpendicular to the direction of said liquid sample flow, the reagent dots in different lines comprise the sequentially different amounts of the binding reagent.

41. The test device of embodiment 1, wherein the plurality of reagent dots comprises two different groups of binding reagents, one group of the reagent dots forms a line that is at a first angle relative to the liquid sample flow direction, and the other group of the reagent dots forms a line that is at a second, different angle relative to the liquid sample flow direction, after the liquid sample flows laterally along the test device, the reagent dots in one of the lines generate a signal indicating the presence and/or amount of an analyte in the liquid sample, and the reagent dots in the other line generate a control signal indicating the test is properly conducted, and when the liquid sample comprises the analyte and the test is properly conducted, the two lines of the reagent dots generate a positive symbol, indicating the presence and/or amount of the analyte in the liquid sample, and when the liquid sample does not comprise the analyte and the test is properly conducted, only one line of the reagent dots generates a negative symbol, indicating the absence of the analyte in the liquid sample.

42. The test device of embodiment 41, wherein one group of the reagent dots forms a line that is substantially parallel to the liquid sample flow direction, and the other group of the reagent dots forms a line that is substantially perpendicular to the liquid sample flow direction, and when the liquid sample comprises the analyte and the test is properly conducted, the two lines of the reagent dots generate a "+" symbol, indicating the presence and/or amount of the analyte in the liquid sample, and when the liquid sample does not comprise the analyte and the test is properly conducted, only one line of the reagent dots generates a "−" symbol, indicating the absence of the analyte in the liquid sample.

43. The test device of embodiment 1, wherein the plurality of reagent dots comprises two different groups of binding reagents, after the liquid sample flows laterally along the test device, reagent dots in one group generate an alpha-numeric signal indicating the presence and/or amount of an analyte in the liquid sample, and the reagent dots in the other group generate a control symbol signal indicating the test is properly conducted.

44. The test device of embodiment 43, wherein the alpha-numeric signal is a word.

45. The test device of embodiment 44, wherein the word is yes, Pos, Positive, Neg, Negative, No, or OK.

46. The test device of any of the embodiments 43-45, wherein the control symbol signal is a "+" sign.

47. The test device of any of the embodiments 43-46, which is configured for a competitive test.

48. The test device of embodiment 1, wherein the plurality of reagent dots comprises a reagent that binds to an intended binder and the binding pattern between the reagent and the binder formed on the reagent dots indicates a kinetic property of the binding between the reagent and the binder.

49. The test device of embodiment 48, wherein the reagent is an antigen, the binder is an antibody to the antigen, and the binding pattern between the antigen and the antibody formed on the reagent dots indicates a kinetic property of the binding between the antigen and the antibody.

50. The test device of embodiment 49, wherein the kinetic property comprises the binding affinity of the binding between the antigen and the antibody.

51. The test device of embodiment 50, wherein the binding pattern of a leading edge on the dot(s) indicates that the antibody has a high binding affinity for the antigen.

52. The test device of any of the embodiments 1-51, which comprises at least one group of the reagent dots that generate an additional signal that is not related to the presence, absence and/or amount of the analyte in the liquid sample, or whether the test is properly conducted.

53. The test device of embodiment 52, wherein the additional signal indicates the authenticity, quality and/or identification of the test device, or identification of the liquid sample.

54. The test device of any of the embodiments 52-53, wherein the additional signal comprises an alpha-numeric signal.

55. The test device of embodiment 1, which comprises at least one group of the reagent dots that form a circle around the sample application location, and the liquid sample moves radially to pass the group of the reagent dots.

56. The test device of embodiment 1, which further comprises a flow through device portion.

57. The test device of any of the embodiments 1-56, wherein the matrix is in the form a strip or a circle.

58. The test device of any of the embodiments 1-56, wherein the matrix is a single element or comprises multiple elements.

59. The test device of any of the embodiments 1-58, which further comprises a sample application element upstream from and in fluid communication with the matrix.

60. The test device of any of the embodiments 1-59, which further comprises a liquid absorption element downstream from and in fluid communication with the matrix.

61. The test device of any of the embodiments 1-60, which further comprises a control location comprising means for indicating proper flow of the liquid sample and/or a valid test result.

62. The test device of any of the embodiments 1-61, wherein at least a portion of the matrix is supported by a solid backing.

63. The test device of any of the embodiments 1-62, wherein a portion of the matrix, upstream from the at least two of the reagent dots, comprises a dried, labeled reagent, the labeled reagent being capable of being moved by a liquid sample and/or a further liquid to the at least two of the reagent dots and/or a control location to generate a detectable signal.

64. The test device of embodiment 63, wherein the dried, labeled reagent is located downstream from a sample application place on the test device.

65. The test device of embodiment 63, wherein the dried, labeled reagent is located upstream from a sample application place on the test device.

66. The test device of any of the embodiments 1-62, which further comprises, upstream from the at least two of the reagent dots, a conjugate element that comprises a dried, labeled reagent, the labeled reagent being capable of moved by a liquid sample and/or a further liquid to the at least two of the reagent dots and/or a control location to generate a detectable signal.

67. The test device of embodiment 66, wherein the conjugate element is located downstream from a sample application place on the test device.

68. The test device of embodiment 66, wherein the conjugate element is located upstream from a sample application place on the test device.

69. The test device of any of the embodiments 63-68, wherein the labeled reagent binds to an analyte in the liquid sample.

70. The test device of any of the embodiments 63-68, wherein the labeled reagent competes with an analyte in the liquid sample for binding to a binding reagent for the analyte at the at least two of the reagent dots.

71. The test device of any of the embodiments 63-70, wherein the label is a soluble label.

72. The test device of any of the embodiments 63-70, wherein the label is a particle label.

73. The test device of any of the embodiments 63-72, wherein the labeled reagent is dried in the presence of a material that: a) stabilizes the labeled reagent; b) facilitates solubilization or resuspension of the labeled reagent in a liquid; and/or c) facilitates mobility of the labeled reagent.

74. The test device of embodiment 73, wherein the material is selected from the group consisting of a protein, a peptide, a polysaccharide, a sugar, a polymer, a gelatin and a detergent.

75. The test device of any of the embodiments 1-74, wherein a sample liquid alone is used to transport the analyte and/or the labeled reagent to the at least two of the reagent dots.

76. The test device of any of the embodiments 1-74, wherein a developing liquid is used to transport the analyte and/or the labeled reagent to the at least two of the reagent dots.

77. The test device of any of the embodiments 1-76, which further comprises a housing that covers at least a portion of the test device, wherein the housing comprises a sample application port to allow sample application upstream from or to the at least two of the reagent dots and an optic opening around the at least two of the reagent dots to allow signal detection at the two of the reagent dots.

78. The test device of embodiment 77, wherein the housing covers the entire test device.

79. The test device of embodiment 77, wherein at least a portion of the sample receiving portion of the matrix or the sample application element is not covered by the housing and a sample is applied to the portion of the sample receiving portion of the matrix or the sample application element outside the housing and then transported to the at least two of the reagent dots.

80. The test device of any of the embodiments 77-79, wherein the housing comprises a plastic material, a biodegradable material or a cellulosic material.

81. The test device of any of the embodiments 1-80, wherein the liquid sample has moved laterally along the test device to generate detectable signal(s) at the at least two of the reagent dots.

82. A method for detecting an analyte in a liquid sample, which method comprises:

a) contacting a liquid sample with the test device of any of the embodiments 1-80, wherein the liquid sample is applied to a site of the test device upstream of the at least two of the reagent dots;

b) transporting an analyte, if present in the liquid sample, and a labeled reagent to the at least two of the reagent dots; and c) assessing the presence, absence, amount and/or pattern of signal(s) generated by the labeled reagent at the at least two of the reagent dots to determining the presence, absence and/or amount of the analyte in the liquid sample.

83. The method of embodiment 82, wherein the liquid sample and the labeled reagent are premixed to form a mixture and the mixture is applied to the test device.

84. The method of embodiment 82, wherein the test device comprises a dried labeled reagent before use and the dried labeled reagent is solubilized or resuspended, and transported to the at least two of the reagent dots by the liquid sample.

85. The method of embodiment 84, wherein the dried labeled reagent is located downstream from the sample application site, and the dried labeled reagent is solubilized or resuspended, and transported to the at least two of the reagent dots by the liquid sample.

86. The method of embodiment 84, wherein the dried labeled reagent is located upstream from the sample application site, and the dried labeled reagent is solubilized or resuspended, and transported to the at least two of the reagent dots by another liquid.

87. The method of embodiment 84, wherein the labeled reagent is solubilized or resuspended, and transported to the at least two of the reagent dots by the liquid sample alone.

88. The method of embodiment 84, wherein the analyte and/or labeled reagent is solubilized or resuspended, and transported to the at least two of the reagent dots by another liquid.

89. The method of any of the embodiments 84-88, wherein the liquid sample is body fluid sample.

90. The method of embodiment 89, wherein the body fluid sample is selected from the group consisting of a whole blood, a serum, a plasma and a urine sample.

91. The method of any of the embodiments 84-88, wherein the liquid sample is a sample derived from a biological, a forensics, a food, a biowarfare, or an environmental source.

92. The method of any of the embodiments 82-91, which is used to quantify or semi-quantify the amount of an analyte in a liquid sample.

93. The method of any of the embodiments 82-91, which is used to detect multiple analytes in a liquid sample.

94. The method of embodiment 93, which is used to quantify or semi-quantify the amounts of the multiple analytes in the liquid sample.

95. The method of any of the embodiments 82-94, wherein the analyte is selected from the group consisting of a cell, a virus and a molecule.

96. The method of any of the embodiments 82-94, wherein the analyte is selected from the group consisting of hCG, hLH, hFSH, hTSH, a cardiac biomarker, an antigen of an infectious organism, an antibody to an infectious organism and disease marker.

97. A process for manufacturing a test device for detecting an analyte in a liquid sample, which process comprises forming a plurality of reagent dots on a matrix to make a test device comprising at least two of said reagent dots that do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, wherein each of said two reagent dots is neither a reagent line across the entire width of said matrix in a direction perpendicular to the direction of said liquid sample flow nor a complete circle of a reagent line, and after a liquid sample flows laterally along said test device and passes said at least two reagent dots, said at least two reagent dots form a predetermined pattern to indicate presence, absence and/or amount of said analyte in said liquid sample.

98. The process of embodiment 97, wherein the plurality of reagent dots form a predetermined pattern selected from the group consisting of a line, multiple lines, a symbol, a geometric shape and an alpha-numeric shape.

99. The process of embodiment 98, wherein the alpha-numeric shape is a letter, a word, a number or a combination thereof.

100. The process of embodiment 98, wherein the line is substantially parallel to the liquid sample flow direction.

101. The process of embodiment 98 wherein the line is substantially perpendicular to the liquid sample flow direction.

102. The process of embodiment 98, wherein the multiple lines comprise at least one line that is substantially parallel to the liquid sample flow direction and at least one line that is substantially perpendicular to the liquid sample flow direction.

103. The process of any of the embodiments 97-102, wherein the plurality of reagent dots are formed by dispensing a reagent at predetermined locations on the matrix 104. The process of embodiment 103, wherein the reagent is dispensed by a drop on demand method or a printing process using a mechanical transfer of the reagent.

105. The process of embodiment 104, wherein the drop on demand method is conducted using an inkjet or solenoid valve based dispenser, a piezoelectric dispenser, screen printing, airjet or airbrush technology, hollow pin printing, and near-contact dispensing.

106. The process of any of the embodiments 97-105, wherein at least one of the reagent dots has a diameter of about 0.1-1 um, 1-10 um, 10-50 um, 51-100 um, 101-200 um, 201-300 um, 301-400 um, 401-500 um and 501-1000 um.

107. The process of any of the embodiments 97-105, wherein at least one of the reagent dots has a diameter or surface area that is about 10%, 5%, 1%, 0.5%, 0.1%, 0.05%, 0.01%, 0.001% or smaller than the length, width or surface area of the matrix.

108. The process of any of the embodiments 97-107, wherein the distance between at least two of the reagent dots is about 1-10 um, 10-50 um, 51-100 um, 101-200 um, 201-300 um, 301-400, 401-500, or 501-600 um.

109. The process of any of the embodiments 97-108, which comprises forming multiple layers of the plurality of reagent dots.

110. The process of any of the embodiments 97-109, which comprises forming at least a layer of the plurality of reagent dots on both sides of the matrix.

111. The process of any of the embodiments 108-110, which further comprises a drying step between forming the multiple layers of the plurality of reagent dots.

112. A test device for detecting an analyte in a liquid sample, which is manufactured by a process of any of the embodiments 97-111.

The ordinarily skilled artisan can appreciate that the present invention can incorporate any number of the preferred features described above.

Further features and advantages of the present invention will become apparent to those of skill in the art in view of the detailed description of preferred embodiments which follows, when considered together with the attached drawings and claims.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

F. EXAMPLES

Example 1

This experiment was conducted to generate a data set to demonstrate aspects of the "pixel" concept for signal development in lateral flow assays. Nitrocellulose membranes (CN 95, Sartorius) were dotted with various patterns and spot sizes as shown in FIGS. 10-16 using a Scienion aspirate-and-dispense piezoelectric-valve system. Biotin—BSA at a concentration of 0.25 mg/ml (DCN) was used as the capture reagent on the membrane. A streptavidin-gold conjugate (40 nm gold, OD10, DCN) was used as the signal reagent. Strips were developed by flowing the streptavidin-gold conjugate laterally along the nitrocellulose membrane in half strip format. The programmed symbols are shown in the A part of FIGS. 10-16 and the symbols obtained from the actual tests are shown in the B part of FIGS. 10-16.

Example 2

This experiment was conducted to illustrate that signal clarity can be improved by removing background binding using a variety of membrane blocking buffers and running diluents and titration of the gold conjugate concentration. The various test strip configurations and test conditions are shown the in the following Table 1 and 2.

TABLE 2

| | Test Strip Configurations |
|---|---|
| A | 700 pL 35 × 35 200 cc 10 |
| B | spots 7 nL |
| C | 700 pL 35 × 35 200 cc |
| D | 15 spots 101.5 nL |
| E | 700 pL 35 × 35 200 cc |
| F | 5 spots 3.5 nL |
| G | 700 pL Double X 17 × 17 |
| H | 15 spots |
| I | 700 pL Double X 17 × 17 |
| J | 10 spots |
| K | 700 pL DoubleX 17 × 17 |
| L | 5 spots |
| M | 700 pL Plus Sign Zig Zag |
| N | 20 spots |
| O | 700 pL Plus Sign 17 × 17 |
| P | 20 spots |
| Q | 700 pL Plus Sign 35 × 35 |
| R | 20 spots |
| S | 700 pL Double X 17 × 17 |
|   | 20 spot |

TABLE 3

| | Test Conditions |
|---|---|
| A | 100 uL PBS(+) 25 uL Conjugate 6 mm Strip, 10 min runtime |
| B | 100 uL PBS(+) 10 uL Conjugate 6 mm Strip, 10 min runtime |
| C | 100 uL 1XPBS w/0.1% Tween-20, 25 uL Conjugate, 10 min runtime |
| D | 100 uL 1XPBS w/0.1% Tween-20 10 uL Conjugate 10 min runtime |
| E | 100 uL 1XPBS w/0.2% Tween-20, 10 uL conjugate, 10 min runtime |
| F | 100 uL 1XPBS w/0.2% Tween-20 + 0.01% BSA, 10 uL conjugate 7 min runtime |
| K | 100 uL 1XPBS w/0.2% Tween-20 + 0.05% BSA, 10 uL Conjugate, 7 min runtime |
| M | 100 uL 1XPBS w/0.3% Tween-20 + 0.05% BSA, 10 uL Conjugate, 7 min runtime |
| N | 100 uL 1XPBS w/ 0.2% Tween-20, 25 uL Conjugate, 10 min runtime, DCN membrane blocking buffer |
| O | 100 uL 1XPBS w/ 0.3% Tween-20 + 0.05% BSA, 20 uL Conjugate, 7 min runtime |
| P | 100 uL 1XPBS, 25 uL conjugate, 10 min runtime, DCN membrane + conjugate pad blocking buffers |
| Q | 100 uL 1XPBS w/ 0.3% Tween-20 + 0.05% BSA, 15 uL Conjugate, 7 min runtime |
| R | 100 uL 1XPBS w/ 0.3% Tween-20 + 0.05% BSA, 10 uL Conjugate, 7 min runtime |
| S | 100 uL 1XPBS, 25 uL conjugate, 10 min runtime, DCN membrane blocking buffer |

As shown in FIG. 17, background signal on the membrane was significantly decreased with less gold conjugate. The "X" membranes were developed completely with 10 ul conjugate, and resulted in minimal background discoloration (See Assay K). The "+" configurations required at least 25 uL, thus producing dark pink membranes. Membrane blocking did not reduce the discoloration (see Assay N). The DCN conjugate pad blocking buffer did not eliminate the background (see Assay S). In this experiment, optimal configurations appear to be K and S.

Example 3

This experiment was conducted to illustrate the use of a fluorescent label, e.g., Europium. Strips spotted with BSA-Biotin capture reagent were developed using a Europium latex-Streptavidin conjugate (100 nm particles, conjugate produced by DCN). In this experiment, 100 ul 1XPBS, 25 uL (1:10 latex diluent) Eu latex conjugate in DCN conjugate pad blocking buffer (10 mM Borate, 3% BSA, 1% PVP40, 0.25% Triton X 100, pH 8.0) laterally along the nitrocellulose membrane. Results were observed and photographed under a black light at the 10 min runtime. As shown in FIG. 18, the Eu-latex conjugate developed a clearly visible signal with minimal background. This demonstrates the utility of the system with fluorescent labels and particles larger than the gold particles.

Example 4. Optimizing Signal Development Using the "Pixel" Concept for Lateral Flow Assays Nitrocellulose membranes (CN 95, Sartorius) were dotted (5 nL) with various patterns as shown in FIGS. 19A-19E using a BioDot aspirate-and-dispense microsolenoid-valve ("BioJet Plus") system. The capture reagent on the membrane was anti-hCG antibody at a concentration of 1 mg/ml. An anti-hCG antibody/gold conjugate (40 nm gold, OD10, DCN) was used as the signal reagent. The hCG analyte was detected at a concentration of 1 UI/mL and diluted in 0.1% Tween-20 in 1XPBS. Strips were developed in half strip format using liquid gold conjugate.

As shown in FIGS. 19A-19E, the vertical alignment of the spots prevented the conjugate from moving up the strip uniformly. The outer edges of the test lines were darkest and demonstrated that the fluid flow was deflected around the dispensed spots instead of flowing through or over them. Variations in the spot pattern, such as increased length of the test line and zig-zag patterns, did not enhance the results.

Increased spacing between the drops showed significant improvements to signal development.

Example 5. Applications of the "Pixel" Concept in Multiplexed Lateral Flow Assays Nitrocellulose membranes (CN 95, Sartorius) were dotted (5 nL) with various patterns as shown in FIGS. 20A-20D using a BioDot aspirate-and-dispense microsolenoid-valve ("BioJet Plus") system. The test reagents on the membrane were anti-hCG antibody (1 mg/ml), and anti-myoglobin antibody (0.5 mg/ml). An anti-Mouse antibody capture reagent was used at a concentration of 0.5 mg/ml as a control for the system. An anti-hCG antibody/gold conjugate (40 nm gold, OD10, DCN) and an anti-Myoglobin antibody/gold conjugate (40 nm, OD10, DCN) were used as the signal reagents. Strips were developed in half strip format using liquid gold conjugate.

As shown in FIGS. 20A-20D, the assay accurately detected the various concentrations of the target analyte in the sample. The anti-Mouse, antimyoglobin and anti-hCG assays ran independently with no evidence of cross-reactivity.

Example 6. Improving Construction of Various Spot Patterns Using a Smaller Dispense Volume Nitrocellulose membranes (CN 95, Sartorius) were dotted (1 nL) with various patterns as shown in FIGS. 21A-21D using a BioDot Piezo dispense system. The test reagent on the membrane was anti-hCG antibody at a concentration of 1 mg/ml. An anti-Mouse antibody capture reagent was used at a concentration of 0.5 mg/ml as a control for the system. An anti-hCG antibody/gold conjugate (40 nm gold, OD10, DCN) was used as the signal reagent. The hCG analyte was detected at a concentration of 1 UI/mL and diluted in 0.1% Tween-20 in 1XPBS. Strips were developed in half strip format using liquid gold conjugate As shown in FIGS. 21A-21D, the configurations produced clean images with even distribution of conjugate, regardless of line placement. The signals in FIGS. 21C and 21D were generated using hCG as analyte. The flow was uninterrupted and able to produce apparent positive and negative result illustrations (although no negative sample was run in the tests shown in FIGS. 21C and 21D).

Citation of the above publications or documents is not intended as an admission that any of the foregoing is pertinent prior art, nor does it constitute any admission as to the contents or date of these publications or documents.

What is claimed is:

1. A test device for detecting an analyte in a liquid sample, which device comprises at least two adjacent reagent dots on a matrix,
    wherein said at least two adjacent reagent dots do not overlap and are sufficiently spaced apart from each other so that when said liquid sample flows laterally along said matrix, flow of said liquid sample to, through and/or around one of said at least two adjacent reagent dots does not substantially affect flow of said liquid sample to, through and/or around said other reagent dot, said at least two adjacent dots do not form a reagent line across the entire width of said matrix in a direction perpendicular to the direction of said liquid sample flow or a complete circle of a reagent line, said at least two adjacent reagent dots form a line that is substantially parallel to the liquid sample flow direction, and after a liquid sample flows laterally along said test device and passes said at least two adjacent reagent dots, said at least two adjacent reagent dots form a predetermined pattern to indicate presence, absence and/or amount of said analyte in said liquid sample, and
    1) wherein at least a quarter, a third, half or all reagent dots have a diameter of about 0.1-1 um, 1-10 μm, 10-50 μm, 51-100 μm, 101-200 μm, 201-300 μm, 301-400 μm, 401-500 μm or 501-1000 μm, or at least a quarter, a third, half or all reagent dots have a diameter or surface area that is about 10%, 5%, 1%, 0.5%, 0.1%, 0.05%, 0.01%, 0.001% or smaller diameter or surface area of the length, width or surface of the matrix, or
    2) wherein the distance between edges of said at least two adjacent dots is about 1-10 μm, 10-50 μm, 51-100 μm, 101-200 μm, 201-300 μm, 301-400 μm, 401-500 μm, or 501-600 μm.

2. The test device of claim 1, wherein the at least two adjacent reagent dots comprise at least 10, 50, 100, 500, 1,000, 5,000, 10,000 or more reagent dots.

3. The test device of claim 1, wherein at least a quarter, a third, half or all reagent dots do not overlap and are sufficiently spaced apart from each other so that when the liquid sample flows laterally along the matrix, flow of the liquid sample to, through and/or around one of the reagent dots does not substantially affect flow of the liquid sample to, through and/or around the other reagent dots.

4. The test device of claim 1, wherein the at least two adjacent reagent dots comprise different reagents and the test device is used to detect multiple analytes in the liquid sample.

5. The test device of claim 1, wherein the at least two adjacent reagent dots comprise the same reagent and the test device is used to detect the amount of the analyte in the liquid sample.

6. The test device of claim 1, wherein the distance between at least a quarter, a third, half or all reagent dots is substantially the same.

7. The test device of claim 1, wherein at least a quarter, a third, half or all reagent dots comprise a reagent that is capable of binding to an analyte or another binding reagent that is capable of binding to an analyte.

8. The test device of claim 1, which comprises multiple layers of the at least two adjacent reagent dots.

9. The test device of claim 1, which comprises at least a layer of the at least two adjacent reagent dots on both sides of the matrix.

10. The test device of claim 1, wherein the reagents are proteins.

11. The test device of claim 1, wherein the matrix has a porous structure.

12. The test device of claim 1, wherein the matrix has a non-porous structure.

13. The test device of claim 1, wherein the at least two adjacent reagent dots comprise two different groups of binding reagents, after the liquid sample flows laterally along the test device, reagent dots in one group generate an alpha-numeric signal indicating the presence and/or amount of an analyte in the liquid sample, and the reagent dots in the other group generate a control symbol signal indicating the test is properly conducted.

14. The test device of claim 1, which is configured for a competitive test.

15. The test device of claim 1, wherein the at least two adjacent reagent dots comprise a reagent that binds to an intended binder and the binding pattern between the reagent and the binder formed on the reagent dots indicates a kinetic property of the binding between the reagent and the binder.

16. The test device of claim 1, which comprises at least one group of the reagent dots that generate an additional signal that is not related to the presence, absence and/or amount of the analyte in the liquid sample, or whether the test is properly conducted.

17. The test device of claim 16, wherein the additional signal indicates the authenticity, quality and/or identification of the test device, or identification of the liquid sample.

18. The test device of claim 1, wherein a portion of the matrix, upstream from the at least two adjacent reagent dots, comprises a dried, labeled reagent, the labeled reagent being capable of being moved by a liquid sample and/or a further liquid to the at least two adjacent reagent dots and/or a control location to generate a detectable signal.

19. A method for detecting an analyte in a liquid sample, which method comprises:
 a) contacting a liquid sample with the test device of claim 1, wherein the liquid sample is applied to a site of the test device upstream of the at least two adjacent reagent dots;
 b) transporting an analyte, if present in the liquid sample, and a labeled reagent to the at least two adjacent reagent dots; and
 c) assessing the presence, absence, amount and/or pattern of signal(s) generated by the labeled reagent at the at least two adjacent reagent dots to determining the presence, absence and/or amount of the analyte in the liquid sample.

20. The method of claim 19, wherein the liquid sample and the labeled reagent are premixed to form a mixture and the mixture is applied to the test device.

21. The method of claim 19, wherein the test device comprises a dried labeled reagent before use and the dried labeled reagent is solubilized or resuspended, and transported to the at least two adjacent reagent dots by the liquid sample.

22. A process for manufacturing a test device for detecting an analyte in a liquid sample, which process comprises forming at least two adjacent reagent dots on a matrix to make a test device comprising said at least two adjacent reagent dots that do not overlap and are sufficiently spaced apart from each other so that when said liquid sample flows laterally along said matrix, flow of said liquid sample to, through and/or around one of said at least two adjacent reagent dots does not substantially affect flow of said liquid sample to, through and/or around said other reagent dot, wherein said at least two adjacent reagent dots do not form a reagent line across the entire width of said matrix in a direction perpendicular to the direction of said liquid sample flow or a complete circle of a reagent line, said at least two adjacent reagent dots form a line that is substantially parallel to the liquid sample flow direction, and after a liquid sample flows laterally along said test device and passes said at least two adjacent reagent dots, said at least two adjacent reagent dots form a predetermined pattern to indicate presence, absence and/or amount of said analyte in said liquid sample, and 3) wherein at least a quarter, a third, half or all reagent dots have a diameter of about 0.1-1 um, 1-10 μm, 10-50 μm, 51-100 μm, 101-200 μm, 201-300 μm, 301-400 μm, 401-500 μm or 501-1000 μm, or at least a quarter, a third, half or all reagent dots have a diameter or surface area that is about 10%, 5%, 1%, 0.5%, 0.1%, 0.05%, 0.01%, 0.001% or smaller diameter or surface area of the length, width or surface of the matrix, or 4) wherein the distance between edges of said at least two adjacent reagent dots is about 1-10 μm, 10-50 μm, 51-100 μm, 101-200 μm, 201-300 μm, 301-400 μm, 401-500 μm, or 501-600 μM.

\* \* \* \* \*